(12) United States Patent
Maizels et al.

(10) Patent No.: US 11,866,467 B2
(45) Date of Patent: Jan. 9, 2024

(54) MATERIALS AND METHODS FOR INDUCING REGULATORY T CELLS

(71) Applicants: THE UNIVERSITY COURT OF THE UNIVERSITY OF GLASGOW, Lanarkshire (GB); THE UNIVERSITY OF EDINBURGH, Edinburgh (GB)

(72) Inventors: Richard Maizels, Lanarkshire (GB); Danielle Smyth, Lanarkshire (GB); Henry McSorley, Lothian (GB)

(73) Assignees: THE UNIVERSITY COURT OF THE UNIVERSITY OF GLASGOW, Glasgow (GB); THE UNIVERSITY OF EDINBURGH, Edinburgh (GB)

( * ) Notice: Subject to any disclaimer, the term of this patent is extended or adjusted under 35 U.S.C. 154(b) by 263 days.

(21) Appl. No.: 16/636,215

(22) PCT Filed: Aug. 3, 2018

(86) PCT No.: PCT/EP2018/071201
§ 371 (c)(1),
(2) Date: Feb. 3, 2020

(87) PCT Pub. No.: WO2019/025621
PCT Pub. Date: Feb. 7, 2019

(65) Prior Publication Data
US 2021/0355176 A1   Nov. 18, 2021

(30) Foreign Application Priority Data

Aug. 4, 2017 (GB) ...................................... 1712556

(51) Int. Cl.
| | | |
|---|---|---|
| *C07K 14/435* | (2006.01) | |
| *A61P 37/06* | (2006.01) | |
| *A61K 35/17* | (2015.01) | |
| *C07K 14/495* | (2006.01) | |
| *C12N 5/0783* | (2010.01) | |
| *A61K 38/00* | (2006.01) | |

(52) U.S. Cl.
CPC .......... *C07K 14/4354* (2013.01); *A61K 35/17* (2013.01); *A61P 37/06* (2018.01); *C07K 14/495* (2013.01); *C12N 5/0637* (2013.01); *A61K 38/00* (2013.01); *C07K 2319/00* (2013.01); *C12N 2501/15* (2013.01)

(58) Field of Classification Search
None
See application file for complete search history.

(56) References Cited

U.S. PATENT DOCUMENTS

2013/0295559 A1* 11/2013 Holliger ............... C12N 9/1252
435/6.1

OTHER PUBLICATIONS

Whisstock, 2003, QUart. Rev. Biophys. vol. 36: 307-340.*
Wang, 2001, J. Biol. Chem. vol. 276: 49213-49220.*
Maizels R. et al., "Immune Regulation by Helminth Parasites: Cellular and Molecular Mechanisms." Nat Rev Immunol. 2003;3(9):733-744.
Elliott D.E. et al., "Helminths as Governors of Immune-Mediated Inflammation."Int J Parasitol. 2007;37(5):457-464.
McSorley H.R. et al., "Helminth Infections and Host Immune Regulation." Clin Microbiol Rev. 2012;25(4):585-608.
Taylor M.D. et al., "Removal of Regulatory T Cell Activity Reverses Hyporesponsiveness and Leads to Filarial Parasite Clearance In Vivo." J Immunol Apr. 15, 2005, 174 (8) 4924-4933.
Blankenhaus B. et al.,"Strongyloides ratti Infection Induces Expansion of Foxp3+ Regulatory T Cells That Interfere with Immune Response and Parasite Clearance in BALB/c Mice." J Immunol 2011; 186:4295-4305.
Maizels R. et al., "Regulatory T Cells in Infection."Adv Immunol. 2011;112:73-136.
Finney C.A.M. et al., "Expansion and activation of CD4+CD25+ regulatory T cells in Heligmosomoides polygyrus infection."Eur J Immunol. 2007;37(7):1874-1886.
Rausch S. et al., "Functional Analysis of Effector and Regulatory T cells in a Parasitic Nematode Infection." Infect Immun. 2008;76(5):1908-1919.
Grainger J.R. et al., "Helminth Secretions Induce de novo T cell Foxp3 expression and regulatory function through the TGF-B pathway." J Exp Med (2010) 207 (11): 2331-2341.
Smith K.A. et al., "Low-level regulatory T-cell Activity is Essential for Functional Type-2 Effector Immunity to Expel Gastrointestinal Helminths." Mucosal Immunol. 2016;9(2):428-443.
McSorley H.J. et al.,"daf-7-related TGF-B Homologues From Trichostrongyloid Nematodes Show Contrasting Lif-Cycle Expression Patterns." Parasitology. Jan. 2010;137(1):159-171.
Hewitson J.P. et al., "Proteomic Analysis of Secretory Products from the Model Gastrointestinal Nematode Heligmosomoides Polygyrus Reveals Dominance of Venom Allergen-Like (VAL) Proteins." Proteomics. 2011;74(9):1573-1594.

(Continued)

*Primary Examiner* — Amy E Juedes
(74) *Attorney, Agent, or Firm* — Kathleen D. Rigaut; Howson & Howson LLP

(57) ABSTRACT

The present invention concerns a structurally distinct immunosuppressive mimic of TGF-β that is a potent inducer of murine and human regulatory T cells and provides a therapeutic agent for the treatment of inflammatory disorders. Disclosed herein is a novel parasite TGF-β mimic which fully replicates the biological and functional properties of TGF-β, including binding to mammalian TGF-β receptors and inducing Foxp3+ Treg in both murine and human CD4+ T cells. This TGF-β mimic shares no homology to mammalian TGF-β or other members of the TGF-β family, but s distinctly related to the component control protein (CCP) superfamily.

7 Claims, 15 Drawing Sheets
Specification includes a Sequence Listing.

(56) References Cited

OTHER PUBLICATIONS

Moreno Y et al., "Proteomic Analysis of Excretory-Secretory Products of Heligmosomoides polygyrus Assessed with Next-Generation Sequencing Transcriptomic Information." PLoS Negl Trop Dis. 2011;5(10):e1370.

Wilson M.S. et al., "Suppression of Allergic Airway Inflammation by Helminth-Induced Regulatory T Cells." J Exp Med. 2005;202(9):1199-1212.

Johnston C.J.C. et al., "Cultivation of Heligmosomoides Polygyrus: An Immunomodulatory Nematode Parasite and its Secreted Products." J. Vis. Exp. (98), e52412 (2015).

Johnston C.J.C. et al., "Helminths and Immunological Tolerance." Transplantation. 2014;97(2):127-132.

Gomez-Escobar N et al., "Identification of tgh-2, a Filarial Nematode Homolog of Caenorhabditis elegans daf-7 and Human Transforming Growth Factor B, Expressed in Microfilarial and Adult Stages of Brugia malayi." Infect. Immun. 2011;68(11):6402-6410.

Beall M.J. et al., "Human Transforming Growth Factor-B Activates a Receptor Serine/Threonine Kinase From the Intravascular Parasite Schistosoma mansoi." J Biol Chem. 2001;276(34):31613-31619.

Zavala-Gongra R et al., "A Member of the Transforming Growth Factor-B receptor Family From Echinococcus Multilocularis is Activated by Human Bone Morphogenetic Protein 2." Mol & Biochem Parasitology 146(2006);265-271.

Robertson I.B. et al., "Unchaining the Beast; Insights From Structural and Evolutionary Studies of TBFB Secretion, Sequestration, and Activation." Cytokine Growth Factor Rev. 2013;24(4):355-372.

Tang Y.T. et al., "Genome of the Human Hookworm Necator Americanus." Nat Genet 46, 261-269 (2014).

International Search Report and Written Opinion, dated Oct. 30, 2018, issued in corresponding International Application No. PCT/EP2018/071201.

Hewitson J.P. et al., "Secretion of Protective Antigens by Tissue-Stage Nematode Larvae Revealed by Proteomic Analysis and Vaccination-Induced Sterile Immunity." PLoS Pathog 9(8): e1003492.

Smyth D.J. et al., "TGF-B Mimic Proteins Form an Extended Gene Family in the Murine Parasite Heligmosomoides Polygyrus." Int J Parasitol. 2018;48(5):379-385.

Johnston C.J.C. et al., "A Structurally Distinct TGF-B Mimic From an Intestinal Helminth Parasite Potently Induces Regulatory T Cells." Nat Commun 8, 1741 (2017).

EMBL AC ATO59092 (Jan. 11, 2017).

* cited by examiner

```
         10         20         30         40         50         60         70         80
MLIFVIGLL EVAATDDSG MPFSDEAATY KYVAKGPKNI EIPAQIDNSG MYPDYTHVKR FCKGLHGEDT TGMFVGICLA 90        100        110        120        130        140        150        160
SQWYYEGVQ ECDDRRCSPL PTNDTVSFEY LKATVNPGII FNITVHPDAS GKYPELTYIK RICKNFPTDS NVQGHIIGMC 170        180        190        200        210        220        230        240
YNAEWQFSST PTCPASGCPP LPDDGIVFYE YYGYAGDRHT VGPVVTKDSS GNYPSPTHAR RCRALSQEA DPGEFVAICY 250        260        270        280        290        300        310        320
KSGTTGESHW EYKNIGCGP DPRCKPLEAN ESVHYEYFTM THETDKKKGP PAKVGKSGKY PEHTCVKKVC SKMPYTCSTG 330        340        350        360        370        380        390        400
GPIFGEC IGA TWNFTALMEC INARGCSSDD LFDKLGFEKV IVRKGEGSDS YKDDFARFYA TGSKVIAECG GKTVRLECSN 410        420
GEWHEPGTKT VHRCTKDGIR TL
```

| | | | | | | | | |
|---|---|---|---|---|---|---|---|---|
| TGM-19-95 | ☐ | .GCMPFSDEAAT.YKYV..AKGPKN.IEIIPAQIDNSGMYPDYTHVKRFCKGLHGEDTT.GWFVGI.CLAS.......QWYYYEG.VQECDDR.... |
| TGM-96-176 | ☐ | .RCSPLPTNDTIVSFEYLKAITVNPGIIFNIIVHPDASGKYPELTYIKRICKNFPTDSNVQGHIIGM.CYNA....EWQFSS..TPTCPAS..... |
| TGM-177-262 | ☐ | .GCPPLPDDGIVFYEYYGYAGDRHT.VGPVVTKDSSGNYPSPTHARRCRALSQEADP.GEFVAI.CYKSGTTGESHWEYYKN..IGKCPDP.... |
| TGM-263-343 | ☐ | .RCKPLEANESVHYEYFTMTNETDKKKGPPAKVGKSGKYPEHTCVKKVCSKWPYTCSTGPPIFGE.CTGA........TWNFTA..LMECINA... |
| TGM-344-422 | ☐ | .RGCSSDDLFDKLGFEKVIVRKGEGS....DSYKDDFARFYATGSKVIAECG......GKTVRLECSNG.....EMHEPGTKTVHRCTKDGIRTL. |
| A.suum-CCP12 | | .QCFGLAP...........................PFNGQISYSQQSSASTYPSGTIATLICN..LGFTVSGG.STAST.CTNG....QWNPST.LGTCQTG.... |
| FH-CCP1 | | .DCNELP............................PRRNTEILTGSWSDQTYPEGTQAIYKCR..PGYRSL.GNVIMV.CRKG.....EWALNP.LRKCQKR.... |
| | | $C^I$ $\underbrace{\qquad\qquad\qquad\qquad}_{Atypical\ insertion}$ $C^{II}$ $C^{III}$ $C^{IV}$ |

C

| 1-18 | 19-71 | 72-95 | 96-151 | 152-176 | 177-233 | 234-262 | 263-321 | 322-343 | 344-390 | 391-422 |
|---|---|---|---|---|---|---|---|---|---|---|
| I | II | III | IV | V | VI | VII | VIII | IX | X | XI |

FIG. 1

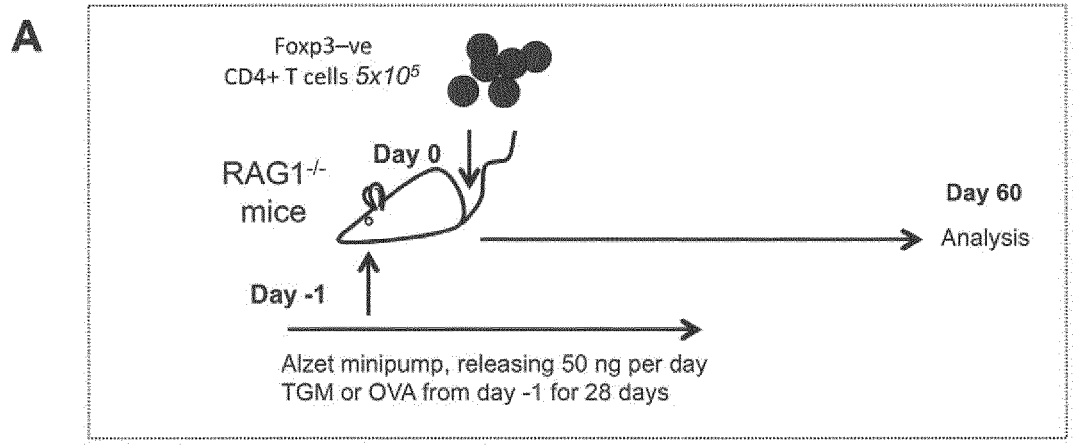
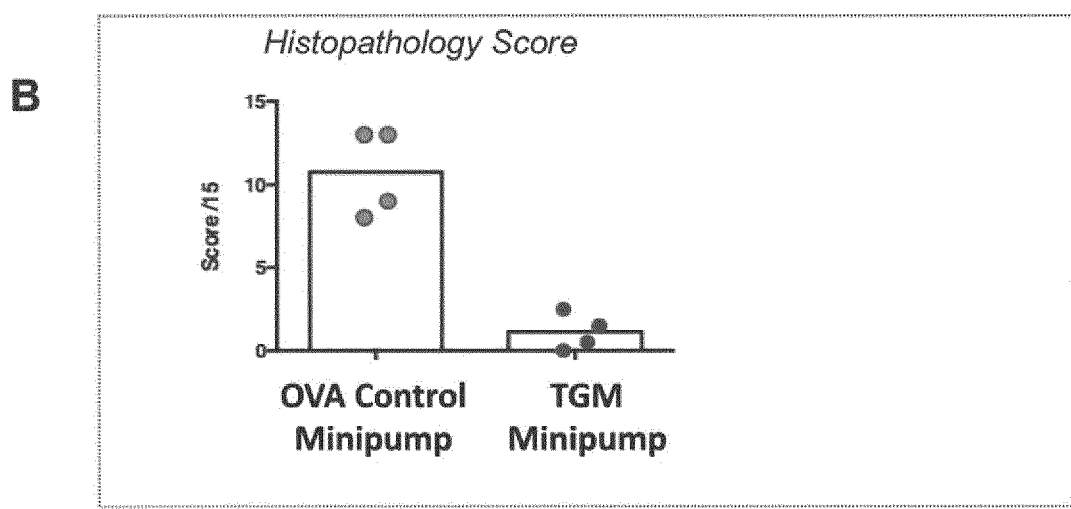
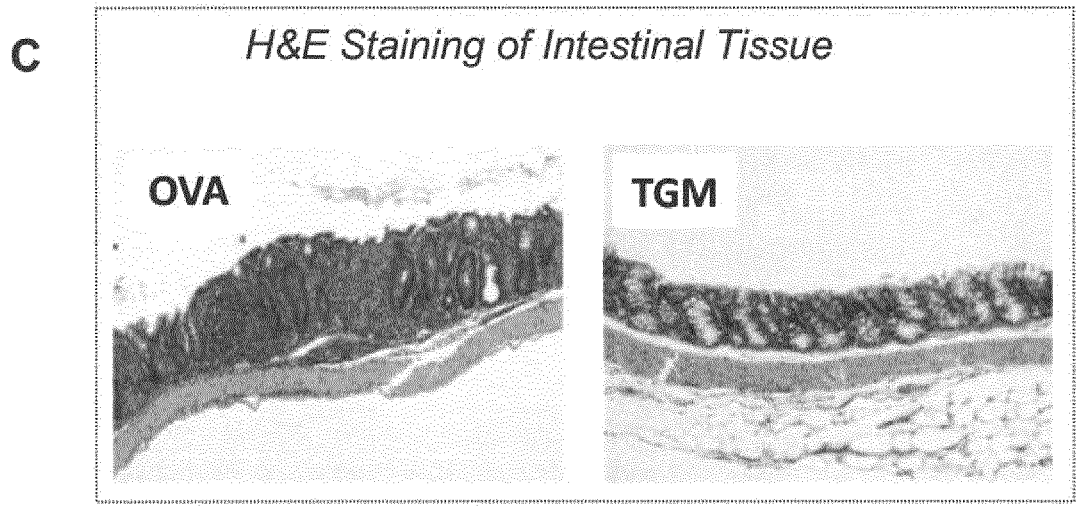
FIG. 8

FIG. 9

Signal 1-18

Domain 1 19-95

Domain 2 96-176

Domain 3 177-262

Domain 4 263-343

Domain 5 344-422

FIG. 10

SEQUENCE LISTING

<160> NUMBER OF SEQ ID NOS: 54

<210> SEQ ID NO 1
<211> LENGTH: 18
<212> TYPE: PRT
<213> ORGANISM: Artificial Sequence
<220> FEATURE:
<223> OTHER INFORMATION: Signal peptide

<400> SEQUENCE: 1

Met Leu Leu Thr Val Val Ile Gly Leu Leu Glu Val Ala Ala Thr Asp
1               5                   10                  15

Asp Ser

<210> SEQ ID NO 2
<211> LENGTH: 77
<212> TYPE: PRT
<213> ORGANISM: Artificial Sequence
<220> FEATURE:
<223> OTHER INFORMATION: TGM Domain 1

<400> SEQUENCE: 2

Gly Cys Met Pro Phe Ser Asp Glu Ala Ala Thr Tyr Lys Tyr Val Ala
1               5                   10                  15

Lys Gly Pro Lys Asn Ile Glu Ile Pro Ala Gln Ile Asp Asn Ser Gly
            20                  25                  30

Met Tyr Pro Asp Tyr Thr His Val Lys Arg Phe Cys Lys Gly Leu His
        35                  40                  45

Gly Glu Asp Thr Thr Gly Trp Phe Val Gly Ile Cys Leu Ala Ser Gln
    50                  55                  60

Trp Tyr Tyr Tyr Glu Gly Val Gln Glu Cys Asp Asp Arg
65                  70                  75

<210> SEQ ID NO 3
<211> LENGTH: 81
<212> TYPE: PRT
<213> ORGANISM: Artificial Sequence
<220> FEATURE:
<223> OTHER INFORMATION: TGM Domain 2

<400> SEQUENCE: 3

Arg Cys Ser Pro Leu Pro Thr Asn Asp Thr Val Ser Phe Glu Tyr Leu
1               5                   10                  15

Lys Ala Thr Val Asn Pro Gly Ile Ile Phe Asn Ile Thr Val His Pro
            20                  25                  30

Asp Ala Ser Gly Lys Tyr Pro Glu Leu Thr Tyr Ile Lys Arg Ile Cys
        35                  40                  45

Lys Asn Phe Pro Thr Asp Ser Asn Val Gln Gly His Ile Ile Gly Met
    50                  55                  60

Cys Tyr Asn Ala Glu Trp Gln Phe Ser Ser Thr Pro Thr Cys Pro Ala
65                  70                  75                  80

Ser

<210> SEQ ID NO 4
<211> LENGTH: 86
<212> TYPE: PRT
<213> ORGANISM: Artificial Sequence
<220> FEATURE:
<223> OTHER INFORMATION: TGM Domain 3

<400> SEQUENCE: 4

```
Gly Cys Pro Pro Leu Pro Asp Asp Gly Ile Val Phe Tyr Glu Tyr Tyr
1               5                   10                  15

Gly Tyr Ala Gly Asp Arg His Thr Val Gly Pro Val Val Thr Lys Asp
            20                  25                  30

Ser Ser Gly Asn Tyr Pro Ser Pro Thr His Ala Arg Arg Cys Arg
        35                  40                  45

Ala Leu Ser Gln Glu Ala Asp Pro Gly Glu Phe Val Ala Ile Cys Tyr
    50                  55                  60

Lys Ser Gly Thr Thr Gly Glu Ser His Trp Glu Tyr Tyr Lys Asn Ile
65                  70                  75                  80

Gly Lys Cys Pro Asp Pro
                85
```

<210> SEQ ID NO 5
<211> LENGTH: 81
<212> TYPE: PRT
<213> ORGANISM: Artificial Sequence
<220> FEATURE:
<223> OTHER INFORMATION: TGM Domain 4

<400> SEQUENCE: 5

```
Arg Cys Lys Pro Leu Glu Ala Asn Glu Ser Val His Tyr Glu Tyr Phe
1               5                   10                  15

Thr Met Thr Asn Glu Thr Asp Lys Lys Lys Gly Pro Pro Ala Lys Val
            20                  25                  30

Gly Lys Ser Gly Lys Tyr Pro Glu His Thr Cys Val Lys Lys Val Cys
        35                  40                  45

Ser Lys Trp Pro Tyr Thr Cys Ser Thr Gly Gly Pro Ile Phe Gly Glu
    50                  55                  60

Cys Ile Gly Ala Thr Trp Asn Phe Thr Ala Leu Met Glu Cys Ile Asn
65                  70                  75                  80

Ala
```

<210> SEQ ID NO 6
<211> LENGTH: 79
<212> TYPE: PRT
<213> ORGANISM: Artificial Sequence
<220> FEATURE:
<223> OTHER INFORMATION: TGM Domain 5

<400> SEQUENCE: 6

```
Arg Gly Cys Ser Ser Asp Asp Leu Phe Asp Lys Leu Gly Phe Glu Lys
1               5                   10                  15

Val Ile Val Arg Lys Gly Glu Gly Ser Asp Ser Tyr Lys Asp Asp Phe
            20                  25                  30

Ala Arg Phe Tyr Ala Thr Gly Ser Lys Val Ile Ala Glu Cys Gly Gly
        35                  40                  45

Lys Thr Val Arg Leu Glu Cys Ser Asn Gly Glu Trp His Glu Pro Gly
    50                  55                  60

Thr Lys Thr Val His Arg Cys Thr Lys Asp Gly Ile Arg Thr Leu
65                  70                  75
```

<210> SEQ ID NO 7
<211> LENGTH: 20
<212> TYPE: PRT
<213> ORGANISM: Artificial Sequence
<220> FEATURE:
<223> OTHER INFORMATION: Polypeptide residue

<400> SEQUENCE: 7

```
Cys Ser Thr Pro Ala Gly Asn Asp Glu Gln His Arg Lys Met Ile Leu
1               5                   10                  15

Val Phe Tyr Trp
            20

<210> SEQ ID NO 8
<211> LENGTH: 32
<212> TYPE: DNA
<213> ORGANISM: Artificial Sequence
<220> FEATURE:
<223> OTHER INFORMATION: coTGM_domain1F

<400> SEQUENCE: 8
gcgcgcggcg cgccgatgat agcggctgca tg                                    32

<210> SEQ ID NO 9
<211> LENGTH: 32
<212> TYPE: DNA
<213> ORGANISM: Artificial Sequence
<220> FEATURE:
<223> OTHER INFORMATION: coTGM_domain2F

<400> SEQUENCE: 9
gcgcgcggcg cgccagatgc agcccctgc cc                                     32

<210> SEQ ID NO 10
<211> LENGTH: 33
<212> TYPE: DNA
<213> ORGANISM: Artificial Sequence
<220> FEATURE:
<223> OTHER INFORMATION: coTGM_domain3F

<400> SEQUENCE: 10
gcgcgcggcg cgccggctgt cctcccctgc ctg                                   33

<210> SEQ ID NO 11
<211> LENGTH: 33
<212> TYPE: DNA
<213> ORGANISM: Artificial Sequence
<220> FEATURE:
<223> OTHER INFORMATION: coTGM_domain4F

<400> SEQUENCE: 11
gcgcgcggcg cgcccggtgc aagcctctgg aag                                   33

<210> SEQ ID NO 12
<211> LENGTH: 33
<212> TYPE: DNA
<213> ORGANISM: Artificial Sequence
<220> FEATURE:
<223> OTHER INFORMATION: coTGM_domain5F

<400> SEQUENCE: 12
gcgcgcggcg cgccagaggc tgcagcagcg acg                                   33

<210> SEQ ID NO 13
<211> LENGTH: 33
<212> TYPE: DNA
<213> ORGANISM: Artificial Sequence
<220> FEATURE:
<223> OTHER INFORMATION: coTGM_domain1R

<400> SEQUENCE: 13
gcgcgcgggc cctctgtcgt cgcattcctg cac                                   33
```

<210> SEQ ID NO 14
<211> LENGTH: 29
<212> TYPE: DNA
<213> ORGANISM: Artificial Sequence
<220> FEATURE:
<223> OTHER INFORMATION: coTGM_domain2R

<400> SEQUENCE: 14
gcgcgcgggc ccgctggcag gacaggtag                                  29

<210> SEQ ID NO 15
<211> LENGTH: 30
<212> TYPE: DNA
<213> ORGANISM: Artificial Sequence
<220> FEATURE:
<223> OTHER INFORMATION: coTGM_domain3R

<400> SEQUENCE: 15
gcgcgcgggc ccggggtcgg ggcacttgcc                                 30

<210> SEQ ID NO 16
<211> LENGTH: 33
<212> TYPE: DNA
<213> ORGANISM: Artificial Sequence
<220> FEATURE:
<223> OTHER INFORMATION: coTGM_domain4R

<400> SEQUENCE: 16
gcgcgcgggc ccggcgttga tgcattccat cag                             33

<210> SEQ ID NO 17
<211> LENGTH: 27
<212> TYPE: DNA
<213> ORGANISM: Artificial Sequence
<220> FEATURE:
<223> OTHER INFORMATION: coTGM_domain5R

<400> SEQUENCE: 17
gcgcgcgggc cccagggtcc ggatgcc                                    27

<210> SEQ ID NO 18
<211> LENGTH: 1408
<212> TYPE: DNA
<213> ORGANISM: Artificial Sequence
<220> FEATURE:
<223> OTHER INFORMATION: TGM

<400> SEQUENCE: 18
acaaccgcat ttatttcatt ccgcgctcag aaaatatcct tcatagtgtg cgaattccgt     60
cctttgtgca ccgatgtaca gttttagttc cgggttcatg ccattcgccg ttagagcact    120
ccagccgcac cgttttacct ccacattctg caatcacttt tgagccggtt gcgtagaacc    180
tggcgaagtc gtccttataa ctatcactgc cttctccttt cctaacaata accttttcga    240
aaccaagttt atcaaacaag tcgtctgagc tacaacctct tgcgttaatg cattccataa    300
gcgcagtaaa attccacgtg cgccaatgc attctccgaa atcggccct ccagtggaac     360
atgtatacgg ccacttgctg caaacctttt tgacgcaggt gtgttcaggg tactttccac    420
tcttgcctac tttcgcgggt gggcctttct ttttgtctgt ctcgttggtc atggtgaagt    480
attcgtagtg aacagactcg ttagcttcca gtggcttgca tctaggatct gggcactttc    540
cgatattctt atagtactcc cagtgacttt ctccagtggt accactttg tagcaaatgg     600
cgacaaattc ccctggatca gcttcttggc tgagtgccct acaacgcctt cttgcatgcg    660

```
tcggtgaagg gtaatttcca gaactgtcct tagttactac tggtccgacg gtatgtcggt        720
cgccagcgta tccgtagtat tcgtagaaga caattccatc gtctggcagc ggtgggcaac        780
cactggctgg gcatgttggt gtgctggaaa attgccactc agcattgtag cacataccga        840
taatatgacc ttgaacattg ctgtctgtag gaaagttttt gcagattctt ttaatgtatg        900
ttagttcagg atattttcca gaggcatctg gatggaccgt tatattaaaa atgattcctg        960
gatttacagt ggctttaaga tactcgaagc tgacagtatc gttagtcggc aacggcgagc       1020
acctacgatc atcgcattct tgtactcctt catagtagta ccattgtgat gcaaggcaga       1080
tgccaacgaa ccaacctgtc gtgtcttctc catgcaatcc tttacagaac cgtttaacat       1140
gtgtataatc aggatacatt ccagaattgt cgatttgcgc aggaatttct atgttcttag       1200
gaccttttgc aacgtatttg taggtggcag cttcatcaga aaacggcatg cagccgctgt       1260
catctgtagc tgcaacctcg agtaggccaa tcactactgt cagcagcatt tcaatgtttt       1320
actaggagca gttccatagg acttggctga tacaactcct gacggaagaa ctgaccgaaa       1380
atcactcacg ctaacgataa aggaccccc                                        1408

<210> SEQ ID NO 19
<211> LENGTH: 1269
<212> TYPE: DNA
<213> ORGANISM: Artificial Sequence
<220> FEATURE:
<223> OTHER INFORMATION: TGM

<400> SEQUENCE: 19
atgctgctga cagtagtgat tggcctactc gaggttgcag ctacagatga cagcggctgc         60
atgccgtttt ctgatgaagc tgccacctac aaatacgttg caaaaggtcc taagaacata        120
gaaattcctg cgcaaatcga caattctgga atgtatcctg attatacaca tgttaaacgg        180
ttctgtaaag gattgcatgg agaagacacg acaggttggt tcgttggcat ctgccttgca        240
tcacaatggt actactatga aggagtacaa gaatgcgatg atcgtaggtg ctcgccgttg        300
ccgactaacg atactgtcag cttcgagtat cttaaagcca ctgtaaatcc aggaatcatt        360
tttaatataa cggtccatcc agatgcctct ggaaaatatc ctgaactaac atacattaaa        420
agaatctgca aaaactttcc tacagacagc aatgttcaag gtcatattat cggtatgtgc        480
tacaatgctg agtggcaatt tccagcaca ccaacatgcc cagccagtgg ttgcccaccg        540
ctgccagacg atggaattgt cttctacgaa tactacggat acgctggcga ccgacatacc        600
gtcggaccag tagtaactaa ggacagttct ggaaattacc cttcaccgac gcatgcaaga        660
aggcgttgta gggcactcag ccaagaagct gatccagggg aatttgtcgc catttgctac        720
aaaagtggta ccactggaga aagtcactgg gagtactata agaatatcgg aaagtgccca        780
gatcctagat gcaagccact ggaagctaac gagtctgttc actacgaata cttcaccatg        840
accaacgaga cagacaaaaa gaaaggccca cccgcgaaag taggcaagag tggaaagtac        900
cctgaacaca cctgcgtcaa aaaggtttgc agcaagtggc cgtatacatg ttccactgga        960
gggccgattt tcggagaatg cattggcgcc acgtggaatt ttactgcgct tatggaatgc       1020
attaacgcaa gaggttgtag ctcagacgac ttgtttgata aacttggttt cgaaaaggtt       1080
attgttagga aggagaagg cagtgatagt tataaggacg acttcgccag gttctacgca       1140
accggctcaa aagtgattgc agaatgtgga ggtaaaacgg tgcggctgga gtgctctaac       1200
ggcgaatggc atgaacccgg aactaaaact gtacatcggt gcacaaagga cggaattcgc       1260
```

-continued

```
acactatga                                                        1269
```

<210> SEQ ID NO 20
<211> LENGTH: 422
<212> TYPE: PRT
<213> ORGANISM: Artificial Sequence
<220> FEATURE:
<223> OTHER INFORMATION: TGM

<400> SEQUENCE: 20

```
Met Leu Leu Thr Val Val Ile Gly Leu Leu Glu Val Ala Ala Thr Asp
1               5                   10                  15

Asp Ser Gly Cys Met Pro Phe Ser Asp Glu Ala Ala Thr Tyr Lys Tyr
            20                  25                  30

Val Ala Lys Gly Pro Lys Asn Ile Glu Ile Pro Ala Gln Ile Asp Asn
        35                  40                  45

Ser Gly Met Tyr Pro Asp Tyr Thr His Val Lys Arg Phe Cys Lys Gly
    50                  55                  60

Leu His Gly Glu Asp Thr Thr Gly Trp Phe Val Gly Ile Cys Leu Ala
65                  70                  75                  80

Ser Gln Trp Tyr Tyr Tyr Glu Gly Val Gln Glu Cys Asp Asp Arg Arg
                85                  90                  95

Cys Ser Pro Leu Pro Thr Asn Asp Thr Val Ser Phe Glu Tyr Leu Lys
            100                 105                 110

Ala Thr Val Asn Pro Gly Ile Ile Phe Asn Ile Thr Val His Pro Asp
        115                 120                 125

Ala Ser Gly Lys Tyr Pro Glu Leu Thr Tyr Ile Lys Arg Ile Cys Lys
    130                 135                 140

Asn Phe Pro Thr Asp Ser Asn Val Gln Gly His Ile Ile Gly Met Cys
145                 150                 155                 160

Tyr Asn Ala Glu Trp Gln Phe Ser Ser Thr Pro Thr Cys Pro Ala Ser
                165                 170                 175

Gly Cys Pro Pro Leu Pro Asp Asp Gly Ile Val Phe Tyr Glu Tyr Tyr
            180                 185                 190

Gly Tyr Ala Gly Asp Arg His Thr Val Gly Pro Val Val Thr Lys Asp
        195                 200                 205

Ser Ser Gly Asn Tyr Pro Ser Pro Thr His Ala Arg Arg Arg Cys Arg
    210                 215                 220

Ala Leu Ser Gln Glu Ala Asp Pro Gly Glu Phe Val Ala Ile Cys Tyr
225                 230                 235                 240

Lys Ser Gly Thr Thr Gly Glu Ser His Trp Glu Tyr Tyr Lys Asn Ile
                245                 250                 255

Gly Lys Cys Pro Asp Pro Arg Cys Lys Pro Leu Glu Ala Asn Glu Ser
            260                 265                 270

Val His Tyr Glu Tyr Phe Thr Met Thr Asn Glu Thr Asp Lys Lys Lys
        275                 280                 285

Gly Pro Pro Ala Lys Val Gly Lys Ser Gly Lys Tyr Pro Glu His Thr
    290                 295                 300

Cys Val Lys Lys Val Cys Ser Lys Trp Pro Tyr Thr Cys Ser Thr Gly
305                 310                 315                 320

Gly Pro Ile Phe Gly Glu Cys Ile Gly Ala Thr Trp Asn Phe Thr Ala
                325                 330                 335

Leu Met Glu Cys Ile Asn Ala Arg Gly Cys Ser Ser Asp Asp Leu Phe
            340                 345                 350

Asp Lys Leu Gly Phe Glu Lys Val Ile Val Arg Lys Gly Glu Gly Ser
```

Asp Ser Tyr Lys Asp Asp Phe Ala Arg Phe Tyr Ala Thr Gly Ser Lys
370                 375                 380

Val Ile Ala Glu Cys Gly Gly Lys Thr Val Arg Leu Glu Cys Ser Asn
385                 390                 395                 400

Gly Glu Trp His Glu Pro Gly Thr Lys Thr Val His Arg Cys Thr Lys
                405                 410                 415

Asp Gly Ile Arg Thr Leu
        420

<210> SEQ ID NO 21
<211> LENGTH: 1408
<212> TYPE: DNA
<213> ORGANISM: Artificial Sequence
<220> FEATURE:
<223> OTHER INFORMATION: TGM-a

<400> SEQUENCE: 21
acaaccacat ttatttcatt ccaagataag agaatatcct tcatagtgcc taattccttc      60
gcttgtgcac cgatgcacag ttcttgtttc gaatcatgc cattcgccgt tagagcactc     120
cagtcgcacc gttttacctt tacattctgc attcactttc gaaccggttg tgtagaacct    180
gacgtagtcg tctttataac tatcgctgcc ttctccttcc ctaaccataa ctatttcaaa    240
gcccaattta ttaaacaagt cgcctccgtc acaaccccct tgcgtttaagc attcgtcaag    300 tgcagtaaaa ttccactggc cgtcaaggca ttctccgaaa atcggccctt taaccgaaca    360
tgtatacggt gacttgtcgc aaaattttct gacacacgtg tgttgagagt attttccacc    420
cttatctact tgcgcgggcg tgccttcctt tttgcctgtc tcgttggcca tggtgaagta    480
ttcgtagcga acagactcgt cagctttcag tggcttgcat ctaggatctg ggcaattctt    540
tatatactta tagtactgcc agtgactttc tccagtggta caacttttgt agcaaatggc    600
gacaaattcc cctgtatcag cttttttggct gagtgcccta caacgccttc ttgcatgcgt    660
cggtgaaggg taatttccag aactgtcctt agttactact ggtccgacgg tatgtcggtc    720
gccagcgtat ccgtagtatt cgtagaagac aattccatcg tctggcagcg gtgggcaacc    780
actggctggg catgttgggt gtgctggaaa attgccactc agcattgtag cacataccga    840
taatatgacc ttgaacattg ctgtctgtag gaaagttttt gcagattctt ttaatgtatg    900
ttagttcagg atattttcca gaggcatctg gatggaccgt tatattaaaa atgattcctg    960
gatttacagt ggctttaaga tactcgaagc tgacagtatc gttagtcggc aacggcgagc    1020
acctacgatc atcgcattct tgtactcctt catagtagta ccattgtgat gcaaggcaga    1080
tgccaacgaa ccaacctgtc gtgtcttctc catgcaatcc tttacagaac cgtttaacat    1140
gtgtataatc aggatacatt ccagaattgt cgatttgcgc aggaatttct atgttcttag    1200
gaccttttgc aacgtatttg taggtggcag cttcatcaga aaacggcatg cagccgctgt    1260
catctgtagc tgcaacctcg agtaggccaa tcactactgt cagcagcatt tcaatgttt    1320 actaggagca gttccatagg acttggctga tacaactcct gacggaagaa ctgaccgaaa    1380
atcactcacg ctaacgataa aggacccc                                       1408

<210> SEQ ID NO 22
<211> LENGTH: 1294
<212> TYPE: DNA
<213> ORGANISM: Artificial Sequence
<220> FEATURE:
<223> OTHER INFORMATION: TGM-a

<400> SEQUENCE: 22

```
atgctgctga cagtagtgat tggcctactc gaggttgcag ctacagatga cagcggctgc      60
atgccgtttt ctgatgaagc tgccacctac aaatacgttg caaaaggtcc taagaacata     120
gaaattcctg cgcaaatcga caattctgga atgtatcctg attatacaca tgttaaacgg     180
ttctgtaaag gattgcatgg agaagacacg acaggttggt tcgttggcat ctgccttgca     240
tcacaatggt actactatga aggagtacaa gaatgcgatg atcgtaggtg ctcgccgttg     300
ccgactaacg atactgtcag cttcgagtat cttaaagcca ctgtaaatcc aggaatcatt     360
tttaatataa cggtccatcc agatgcctct ggaaaatatc tgaactaac atacattaaa      420
agaatctgca aaactttcc tacagacagc aatgttcaag tcatattat cggtatgtgc       480
tacaatgctg agtggcaatt ttccagcaca cccaacatgc ccagccagtg gttgcccacc     540
gctgccagac gatggaattg tcttctacga atactacgga tacgctggcg accgacatac     600
cgtcggacca gtagtaacta aggacagttc tggaaattac ccttcaccga cgcatgcaag     660
aaggcgttgt agggcactca gccaaaaagc tgatacaggg gaatttgtcg ccatttgcta     720
caaaagttgt accactggag aaagtcactg gcagtactat aagtatataa agaattgccc     780
agatcctaga tgcaagccac tgaaagctga cgagtctgtt cgctacgaat acttcaccat     840
ggccaacgag acaggcaaaa aggaaggcac gcccgcgcaa gtagataagg gtggaaaata     900
ctctcaacac acgtgtgtca gaaaattttg cgacaagtca ccgtatacat gttcggttaa     960
agggccgatt tcggagaat gccttgacgg ccagtggaat tttactgcac ttgacgaatg    1020
cttaaacgca aggggttgtg acggaggcga cttgtttaat aaattgggct ttgaaatagt    1080
tatggttagg gaaggagaag gcagcgatag ttataaagac gactacgtca ggttctacac    1140
aaccggttcg aaagtgaatg cagaatgtaa aggtaaaacg gtgcgactgg agtgctctaa    1200
cggcgaatgg catgattcgg aaacaagaac tgtgcatcgg tgcacaagcg aaggaattag    1260
gcactatgaa ggatattctc ttatcttgga atga                                1294
```

<210> SEQ ID NO 23
<211> LENGTH: 430
<212> TYPE: PRT
<213> ORGANISM: Artificial Sequence
<220> FEATURE:
<223> OTHER INFORMATION: TGM-a

<400> SEQUENCE: 23

```
Met Leu Leu Thr Val Val Ile Gly Leu Leu Glu Val Ala Ala Thr Asp
1               5                   10                  15

Asp Ser Gly Cys Met Pro Phe Ser Asp Glu Ala Ala Thr Tyr Lys Tyr
            20                  25                  30

Val Ala Lys Gly Pro Lys Asn Ile Glu Ile Pro Ala Gln Ile Asp Asn
        35                  40                  45

Ser Gly Met Tyr Pro Asp Tyr Thr His Val Lys Arg Phe Cys Lys Gly
    50                  55                  60

Leu His Gly Glu Asp Thr Thr Gly Trp Phe Val Gly Ile Cys Leu Ala
65                  70                  75                  80

Ser Gln Trp Tyr Tyr Tyr Glu Gly Val Gln Glu Cys Asp Asp Arg Arg
                85                  90                  95

Cys Ser Pro Leu Pro Thr Asn Asp Thr Val Ser Phe Glu Tyr Leu Lys
            100                 105                 110

Ala Thr Val Asn Pro Gly Ile Ile Phe Asn Ile Thr Val His Pro Asp
```

115                 120                 125
Ala Ser Gly Lys Tyr Pro Glu Leu Thr Tyr Ile Lys Arg Ile Cys Lys
130                 135                 140

Asn Phe Pro Thr Asp Ser Asn Val Gln Gly His Ile Ile Gly Met Cys
145                 150                 155                 160

Tyr Asn Ala Glu Trp Gln Phe Ser Ser Thr Pro Thr Cys Pro Ala Ser
                165                 170                 175

Gly Cys Pro Pro Leu Pro Asp Asp Gly Ile Val Phe Tyr Glu Tyr Tyr
                180                 185                 190

Gly Tyr Ala Gly Asp Arg His Thr Val Gly Pro Val Val Thr Lys Asp
                195                 200                 205

Ser Ser Gly Asn Tyr Pro Ser Pro Thr His Ala Arg Arg Cys Arg
210                 215                 220

Ala Leu Ser Gln Lys Ala Asp Thr Gly Glu Phe Val Ala Ile Cys Tyr
225                 230                 235                 240

Lys Ser Cys Thr Thr Gly Glu Ser His Trp Gln Tyr Tyr Lys Tyr Ile
                245                 250                 255

Lys Asn Cys Pro Asp Pro Arg Cys Lys Pro Leu Lys Ala Asp Glu Ser
                260                 265                 270

Val Arg Tyr Glu Tyr Phe Thr Met Ala Asn Glu Thr Gly Lys Lys Glu
                275                 280                 285

Gly Thr Pro Ala Gln Val Asp Lys Gly Lys Tyr Ser Gln His Thr
290                 295                 300

Cys Val Arg Lys Phe Cys Asp Lys Ser Pro Tyr Thr Cys Ser Val Lys
305                 310                 315                 320

Gly Pro Ile Phe Gly Glu Cys Leu Asp Gly Gln Trp Asn Phe Thr Ala
                325                 330                 335

Leu Asp Glu Cys Leu Asn Ala Arg Gly Cys Asp Gly Gly Asp Leu Phe
                340                 345                 350

Asn Lys Leu Gly Phe Glu Ile Val Met Val Arg Glu Gly Glu Gly Ser
                355                 360                 365

Asp Ser Tyr Lys Asp Asp Tyr Val Arg Phe Tyr Thr Thr Gly Ser Lys
                370                 375                 380

Val Asn Ala Glu Cys Lys Gly Lys Thr Val Arg Leu Glu Cys Ser Asn
385                 390                 395                 400

Gly Glu Trp His Asp Ser Glu Thr Arg Thr Val His Arg Cys Thr Ser
                405                 410                 415

Glu Gly Ile Arg His Tyr Glu Gly Tyr Ser Leu Ile Leu Glu
                420                 425                 430

<210> SEQ ID NO 24
<211> LENGTH: 1163
<212> TYPE: DNA
<213> ORGANISM: Artificial Sequence
<220> FEATURE:
<223> OTHER INFORMATION: TGM-b

<400> SEQUENCE: 24
aaccacattt atttcactcc aagatgagaa atattcttc atggtgcgcg aagtccttcc      60
tttgtgcacc ggtgcacagt tttagttccg ggatcatgcc attaccgtt agagcactcc     120 agccgcaccg tgttaccttt acattcggca ttcactttcg aaccggttgc gtagaaccgg    180
gcaaagtcgt cctataact atcactgcct tcttcttctc taaccataac tccttcaaag    240
cccagtttat caaacaagtc gtcactgtta caaccccta gatctgggca cttccttata    300

| | |
|---|---|
| tgactgtagt aatcccaatg actttcgcca gtggtaccac atctgtagca aatgccaaca | 360 |
| aattcccctg gatcagcttt ttggctgagt gccctacaac gccttcttgc atgcgtcggt | 420 |
| gaagggtaat ttccagaact gtccttagtt actgctggtc cgacggtatg tcgatcgcca | 480 |
| gcgtatccgt agtattcgtg gaagacgatt ccatcgtctg gcagcggtgg gcaaccaatt | 540 |
| gaagggcttg ttggtgtgct ggaaaaccgc cattcagcat tgtagcacat gccgataata | 600 |
| tgaccttgaa ctttgctgtc agtaggaaaa tttttgcaga ttcttttaat gtatgttagt | 660 |
| tcaggatatt ttccagtggc atctggatgg accgttatat taaaaatgat tcctggattt | 720 |
| acagtggctt taagatactc gaaggtgaca gtatcgtccg tcgacaacgg caagcaccca | 780 |
| cgacctccgc attcttgtac tccttgatag tagacccatt ctgatccagg gcctatgcca | 840 |
| acgaaccaac ctgtcgtgtc ttctccatgc aatcctttac aaaaccgttt aacatgtgta | 900 |
| taatcaggat acattccaga attgtcgatt tgcgcaggaa tttctatgtt cttaggacct | 960 |
| tttgcaacgt atttgtaggt ggcagcttca tcagaaaacg gcatgcagcc gctgtcatct | 1020 |
| gtagctgcaa cctcgagtag gccaatcact actgtcagca gcatttcaat gtttactag | 1080 |
| gagcagttcc ataggacttg gctgatacaa ctcctgacgg aagaactgac cgaaaatcac | 1140 |
| tcacgctaac gataaaggac ccc | 1163 |

<210> SEQ ID NO 25
<211> LENGTH: 1026
<212> TYPE: DNA
<213> ORGANISM: Artificial Sequence
<220> FEATURE:
<223> OTHER INFORMATION: TGM-b

<400> SEQUENCE: 25

| | |
|---|---|
| atgctgctga cagtagtgat tggcctactc gaggttgcag ctacagatga cagcggctgc | 60 |
| atgccgtttt ctgatgaagc tgccacctac aaatacgttg caaaaggtcc taagaacata | 120 |
| gaaattcctg cgcaaatcga caattctgga atgtatcctg attatacaca tgttaaacgg | 180 |
| ttttgtaaag gattgcatgg agaagacacg acaggttggt tcgttggcat aggccctgga | 240 |
| tcagaatggg tctactatca aggagtacaa gaatgcggag tcgtgggtg cttgccgttg | 300 |
| tcgacggacg atactgtcac cttcgagtat cttaaagcca ctgtaaatcc aggaatcatt | 360 |
| tttaatataa cggtccatcc agatgccact ggaaaatatc ctgaactaac atacattaaa | 420 |
| agaatctgca aaattttcc tactgacagc aaagttcaag gtcatattat cggcatgtgc | 480 |
| tacaatgctg aatggcggtt ttccagcaca ccaacaagcc cttcaattgg ttgcccaccg | 540 |
| ctgccagacg atggaatcgt cttccacgaa tactacggat acgctggcga tcgacatacc | 600 |
| gtcggaccag cagtaactaa ggacagttct ggaaattacc cttcaccgac gcatgcaaga | 660 |
| aggcgttgta gggcactcag ccaaaaagct gatccagggg aatttgttgg catttgctac | 720 |
| agatgtggta ccactggcga aagtcattgg gattactaca gtcatataag gaagtgccca | 780 |
| gatcctaggg gttgtaacag tgacgacttg tttgataaac tgggctttga aggagttatg | 840 |
| gttagagaag aagaaggcag tgatagttat aaggacgact ttgcccggtt ctacgcaacc | 900 |
| ggttcgaaag tgaatgccga atgtaaaggt aacacggtgc ggctgagtg ctctaacggt | 960 |
| gaatggcatg atcccggaac taaaactgtg caccggtgca caaggaagg acttcgcgca | 1020 |
| ccatga | 1026 |

<210> SEQ ID NO 26
<211> LENGTH: 341

<212> TYPE: PRT
<213> ORGANISM: Artificial Sequence
<220> FEATURE:
<223> OTHER INFORMATION: TGM-b

<400> SEQUENCE: 26

Met Leu Leu Thr Val Val Ile Gly Leu Leu Glu Val Ala Ala Thr Asp
1               5                   10                  15

Asp Ser Gly Cys Met Pro Phe Ser Asp Glu Ala Ala Thr Tyr Lys Tyr
            20                  25                  30

Val Ala Lys Gly Pro Lys Asn Ile Glu Ile Pro Ala Gln Ile Asp Asn
        35                  40                  45

Ser Gly Met Tyr Pro Asp Tyr Thr His Val Lys Arg Phe Cys Lys Gly
50                  55                  60

Leu His Gly Glu Asp Thr Thr Gly Trp Phe Val Gly Ile Gly Pro Gly
65                  70                  75                  80

Ser Glu Trp Val Tyr Tyr Gln Gly Val Gln Glu Cys Gly Gly Arg Gly
                85                  90                  95

Cys Leu Pro Leu Ser Thr Asp Asp Thr Val Thr Phe Glu Tyr Leu Lys
            100                 105                 110

Ala Thr Val Asn Pro Gly Ile Ile Phe Asn Ile Thr Val His Pro Asp
        115                 120                 125

Ala Thr Gly Lys Tyr Pro Glu Leu Thr Tyr Ile Lys Arg Ile Cys Lys
130                 135                 140

Asn Phe Pro Thr Asp Ser Lys Val Gln Gly His Ile Ile Gly Met Cys
145                 150                 155                 160

Tyr Asn Ala Glu Trp Arg Phe Ser Ser Thr Pro Thr Ser Pro Ser Ile
                165                 170                 175

Gly Cys Pro Pro Leu Pro Asp Asp Gly Ile Val Phe His Glu Tyr Tyr
            180                 185                 190

Gly Tyr Ala Gly Asp Arg His Thr Val Gly Pro Ala Val Thr Lys Asp
        195                 200                 205

Ser Ser Gly Asn Tyr Pro Ser Pro Thr His Ala Arg Arg Cys Arg
210                 215                 220

Ala Leu Ser Gln Lys Ala Asp Pro Gly Glu Phe Val Gly Ile Cys Tyr
225                 230                 235                 240

Arg Cys Gly Thr Thr Gly Glu Ser His Trp Asp Tyr Tyr Ser His Ile
                245                 250                 255

Arg Lys Cys Pro Asp Pro Arg Gly Cys Asn Ser Asp Asp Leu Phe Asp
            260                 265                 270

Lys Leu Gly Phe Glu Gly Val Met Val Arg Glu Glu Gly Ser Asp
        275                 280                 285

Ser Tyr Lys Asp Asp Phe Ala Arg Phe Tyr Ala Thr Gly Ser Lys Val
290                 295                 300

Asn Ala Glu Cys Lys Gly Asn Thr Val Arg Leu Glu Cys Ser Asn Gly
305                 310                 315                 320

Glu Trp His Asp Pro Gly Thr Lys Thr Val His Arg Cys Thr Lys Glu
                325                 330                 335

Gly Leu Arg Ala Pro
            340

<210> SEQ ID NO 27
<211> LENGTH: 856
<212> TYPE: DNA
<213> ORGANISM: Artificial Sequence
<220> FEATURE:

<223> OTHER INFORMATION: TGM-c

<400> SEQUENCE: 27

| tggtttaatt | acccaagttt | tgaggggatc | attgcggaac | tcgacgctcc | accaagatgc | 60 |
| tatcattatt | cattgccatc | ggattgcttg | aggctgctgg | atcaagttgt | ccacccgtgg | 120 |
| gcgatgcagc | aattaaggac | agtctcgaaa | attatcctcc | gaatacgcat | gcaagaagac | 180 |
| attgcaaagc | actcagcaaa | aaagctgacc | caggagaatt | tgtcgccatt | tgctaccaaa | 240 |
| gaagaggcac | tagtgaaagt | caatggcagt | attatcctag | aatagcatca | tgtccagacc | 300 |
| ctaggtgcaa | gcctctcgaa | aaaacgatt | ctgttagcta | tgaatatttc | acaaacccca | 360 |
| ctaaaggact | gaagatgggt | tcaatcacaa | agccggacaa | aagtggaaag | taccctgaag | 420 |
| aaacttttgt | tagaaggtat | tgcaatgacc | ttccaaggaa | cagcctagcg | caaggaaaaa | 480 |
| cctacgcaga | gtgcttggat | tcagagtgga | agcttaaaaa | tttgccagac | tgtcgattcg | 540 |
| cagcaggatg | tgacgaagaa | tatctgcttg | agaagttaat | gttcgttgat | atttcgtact | 600 |
| ggggaaaaga | tgcagcgaaa | ttttccgatg | acaaaacata | taggtattat | cggcccggtt | 660 |
| cgaaagttac | tgcgaagtgc | aaaggtaaat | ctgtgaagtt | aacatgtgtt | gacggcggct | 720 |
| actgggttac | agtggacggc | agaaaggcgc | tctgcacatg | agacggtcct | cacagttgaa | 780 |
| gtgcaataaa | tattttcgct | accagatgat | gaaactgtct | ggtacgaata | ctacggatac | 840 |
| gttgacggtc | gacata | | | | | 856 |

<210> SEQ ID NO 28
<211> LENGTH: 765
<212> TYPE: DNA
<213> ORGANISM: Artificial Sequence
<220> FEATURE:
<223> OTHER INFORMATION: TGM-c

<400> SEQUENCE: 28

| atgctatcat | tattcattgc | catcggattg | cttgaggctg | ctggatcaag | ttgtccaccg | 60 |
| ctaccagatg | atgaaactgt | ctggtacgaa | tactacggat | acgttgacgg | tcgacatacc | 120 |
| gtgggcgatg | cagcaattaa | ggacagtctc | gaaaattatc | ctccgaatac | gcatgcaaga | 180 |
| agacattgca | aagcactcag | caaaaaagct | gacccaggag | aatttgtcgc | catttgctac | 240 |
| caaagaagag | gcactagtga | aagtcaatgg | cagtattatc | ctagaatagc | atcatgtcca | 300 |
| gaccctaggt | gcaagcctct | cgaaaaaaac | gattctgtta | gctatgaata | tttcacaaaa | 360 |
| cccactaaag | gactgaagat | gggttcaatc | acaaagccgg | acaaaagtgg | aaagtaccct | 420 |
| gaagaaactt | ttgttagaag | gtattgcaat | gaccttccaa | ggaacagcct | agcgcaagga | 480 |
| aaaacctacg | cagagtgctt | ggattcagag | tggaagctta | aaaatttgcc | agactgtcga | 540 |
| ttcgcagcag | gatgtgacga | agaatatctg | cttgagaagt | taatgttcgt | tgatatttcg | 600 |
| tactggggaa | aagatgcagc | gaaattttcc | gatgacaaaa | catataggta | ttatcggccc | 660 |
| ggttcgaaag | ttactgcgaa | gtgcaaaggt | aaatctgtga | agttaacatg | tgttgacggc | 720 |
| ggctactggg | ttacagtgga | cggcagaaag | gcgctctgca | catga | | 765 |

<210> SEQ ID NO 29
<211> LENGTH: 254
<212> TYPE: PRT
<213> ORGANISM: Artificial Sequence
<220> FEATURE:
<223> OTHER INFORMATION: TGM-c

<400> SEQUENCE: 29

Met Leu Ser Leu Phe Ile Ala Ile Gly Leu Leu Glu Ala Ala Gly Ser
1               5                   10                  15

Ser Cys Pro Pro Leu Pro Asp Asp Glu Thr Val Trp Tyr Glu Tyr Tyr
            20                  25                  30

Gly Tyr Val Asp Gly Arg His Thr Val Gly Asp Ala Ala Ile Lys Asp
            35                  40                  45

Ser Leu Glu Asn Tyr Pro Pro Asn Thr His Ala Arg Arg His Cys Lys
50                      55                  60

Ala Leu Ser Lys Lys Ala Asp Pro Gly Glu Phe Val Ala Ile Cys Tyr
65                  70                  75                  80

Gln Arg Arg Gly Thr Ser Glu Ser Gln Trp Gln Tyr Tyr Pro Arg Ile
                85                  90                  95

Ala Ser Cys Pro Asp Pro Arg Cys Lys Pro Leu Glu Lys Asn Asp Ser
            100                 105                 110

Val Ser Tyr Glu Tyr Phe Thr Lys Pro Thr Lys Gly Leu Lys Met Gly
            115                 120                 125

Ser Ile Thr Lys Pro Asp Lys Ser Gly Lys Tyr Pro Glu Glu Thr Phe
130                 135                 140

Val Arg Arg Tyr Cys Asn Asp Leu Pro Arg Asn Ser Leu Ala Gln Gly
145                 150                 155                 160

Lys Thr Tyr Ala Glu Cys Leu Asp Ser Glu Trp Lys Leu Lys Asn Leu
                165                 170                 175

Pro Asp Cys Arg Phe Ala Ala Gly Cys Asp Glu Glu Tyr Leu Leu Glu
            180                 185                 190

Lys Leu Met Phe Val Asp Ile Ser Tyr Trp Gly Lys Asp Ala Ala Lys
            195                 200                 205

Phe Ser Asp Asp Lys Thr Tyr Arg Tyr Arg Pro Gly Ser Lys Val
210                 215                 220

Thr Ala Lys Cys Lys Gly Lys Ser Val Lys Leu Thr Cys Val Asp Gly
225                 230                 235                 240

Gly Tyr Trp Val Thr Val Asp Gly Arg Lys Ala Leu Cys Thr
                245                 250

<210> SEQ ID NO 30
<211> LENGTH: 1402
<212> TYPE: DNA
<213> ORGANISM: Artificial Sequence
<220> FEATURE:
<223> OTHER INFORMATION: TGM-d

<400> SEQUENCE: 30
aaccacattt atttcactcc aagatgagaa atattcttc atggtgcgcg aagtccttcc      60
tttgtgcacg atgcacagtt ttagctccca aatcatgcca ttcgccgtta gagcactcca    120
gccgcgccgt ttcacctcga cattgtgcac tgactttaga accggttgcg tagaacaaga    180
cgtaggcgtc cctataacta tcactgaatt ctccttccct aaccattatt ctttgaagc     240 ccagctcaaa caagtcgttt cgtcacaac ctcttgcgtt aatgcattcc ataagcgcag     300
taaaattcca cgtggcgcca atgcattctc cgaaaatcgg ccctccagcg aacatgtat    360 acggccactt gctgcaaacc ttttttgacgc aggtgtgttc agggtacttt ccactcttgc    420
ctactttcgc gggtgggcct ttcttttgt ctgtctcgtt ggtcatggtg aagtattcgt      480
agtgaacaga ctcgttagct tccagtggct tgcatctagg atctgggcac tttccgatat    540
tcttatagta ctcccagtga ctttctccag tggtaccact tttgtagcaa atggcgacaa    600

| | |
|---|---|
| attccctgg atcagcttct tggctgagtg ccctacaacg ccttcttgca tgcgtcggtg | 660 |
| aagggtaatt ccagaactg tccttagtta ctactggtcc gacggtatgt cggtcgccag | 720 |
| cgtatccgta gtattcgtag aagacaattc catcgtctgg cagcggtggg caaccactgg | 780 |
| ctgggcatgt tggtgtgctg gaaaattgcc actcagcatt gtagcacata ccgataatat | 840 |
| gaccttgaac attgctgtct gtaggaaagt ttttgcagat tcttttaatg tatgttagtt | 900 |
| caggatattt tccagaggca tctggatgga ccgttatatt aaaaatgatt cctggattta | 960 |
| cagtggcttt aagatactcg aagctgacag tatcgttagt cggcaacggc gagcacctac | 1020 |
| gatcatcgca ttcttgtact ccttcatagt agtaccattg tgatgcaagg cagatgccaa | 1080 |
| cgaaccaacc tgtcgtgtct tctccatgca atccttaca gaaccgttta acatgtgtat | 1140 |
| aatcaggata cattccagaa ttgtcgattt gcgcaggaat ttctatgttc ttaggacctt | 1200 |
| ttgcaacgta tttgtaggtg gcagcttcat cagaaacgg catgcagccg ctgtcatctg | 1260 |
| tagctgcaac ctcgagtagg ccaatcacta ctgtcagcag catttcaatg ttttactagg | 1320 |
| agcagttcca taggacttgg ctgatacaac tcctgacgga agaactgacc gaaaatcact | 1380 |
| cacgctaacg ataaaggacc cc | 1402 |

<210> SEQ ID NO 31
<211> LENGTH: 1290
<212> TYPE: DNA
<213> ORGANISM: Artificial Sequence
<220> FEATURE:
<223> OTHER INFORMATION: TGM-d

<400> SEQUENCE: 31

| | |
|---|---|
| atgctgctga cagtagtgat tggcctactc gaggttgcag ctacagatga cagcggctgc | 60 |
| atgccgtttt ctgatgaagc tgccacctac aaatacgttg caaaaggtcc taagaacata | 120 |
| gaaattcctg cgcaaatcga caattctgga atgtatcctg attatacaca tgttaaacgg | 180 |
| ttctgtaaag gattgcatgg agaagacacg acaggttggt tcgttggcat ctgccttgca | 240 |
| tcacaatggt actactatga aggagtacaa gaatgcgatg atcgtaggtg ctcgccgttg | 300 |
| ccgactaacg atactgtcag cttcgagtat cttaaagcca ctgtaaatcc aggaatcatt | 360 |
| tttaatataa cggtccatcc agatgcctct ggaaaatatc ctgaactaac atacattaaa | 420 |
| agaatctgca aaactttcc tacagacagc aatgttcaag gtcatattat cggtatgtgc | 480 |
| tacaatgctg agtggcaatt ttccagcaca ccaacatgcc cagccagtgg ttgcccaccg | 540 |
| ctgccagacg atggaattgt cttctacgaa tactacggat acgctggcga ccgacatacc | 600 |
| gtcggaccag tagtaactaa ggacagttct ggaaattacc cttcaccgac gcatgcaaga | 660 |
| aggcgttgta gggcactcag ccaagaagct gatccagggg aatttgtcgc catttgctac | 720 |
| aaaagtggta ccactggaga agtcactgg gagtactata gaatatcgg aaagtgccca | 780 |
| gatcctagat gcaagccact ggaagctaac gagtctgttc actacgaata cttcaccatg | 840 |
| accaacgaga cagacaaaaa gaaaggccca cccgcgaaag taggcaagag tggaaagtac | 900 |
| cctgaacaca cctgcgtcaa aaaggtttgc agcaagtggc cgtatacatg ttccgctgga | 960 |
| gggccgattt tcggagaatg cattggcgcc acgtggaatt ttactgcgct tatgaatgc | 1020 |
| attaacgcaa gaggttgtga cgaaaacgac ttgtttgagc tgggcttcaa agaaataatg | 1080 |
| gttagggaag gagaattcag tgatagttat agggacgcct acgtcttgtt ctacgcaacc | 1140 |
| ggttctaaag tcagtgcaca atgtcgaggt gaaacgcgc ggctgagtg ctctaacggc | 1200 |
| gaatggcatg atttgggagc taaaactgtg catcgtgcac aaaggaagga cttcgcgcac | 1260 | catgaagaat attttctcat cttggagtga 1290

<210> SEQ ID NO 32
<211> LENGTH: 429
<212> TYPE: PRT
<213> ORGANISM: Artificial Sequence
<220> FEATURE:
<223> OTHER INFORMATION: TGM-d

<400> SEQUENCE: 32

Met Leu Leu Thr Val Ile Gly Leu Leu Glu Val Ala Ala Thr Asp
1               5                   10                  15

Asp Ser Gly Cys Met Pro Phe Ser Asp Glu Ala Ala Thr Tyr Lys Tyr
            20                  25                  30

Val Ala Lys Gly Pro Lys Asn Ile Glu Ile Pro Ala Gln Ile Asp Asn
        35                  40                  45

Ser Gly Met Tyr Pro Asp Tyr Thr His Val Lys Arg Phe Cys Lys Gly
    50                  55                  60

Leu His Gly Glu Asp Thr Thr Gly Trp Phe Val Gly Ile Cys Leu Ala
65                  70                  75                  80

Ser Gln Trp Tyr Tyr Tyr Glu Gly Val Gln Glu Cys Asp Asp Arg Arg
                85                  90                  95

Cys Ser Pro Leu Pro Thr Asn Asp Thr Val Ser Phe Glu Tyr Leu Lys
            100                 105                 110

Ala Thr Val Asn Pro Gly Ile Ile Phe Asn Ile Thr Val His Pro Asp
        115                 120                 125

Ala Ser Gly Lys Tyr Pro Glu Leu Thr Tyr Ile Lys Arg Ile Cys Lys
    130                 135                 140

Asn Phe Pro Thr Asp Ser Asn Val Gln Gly His Ile Ile Gly Met Cys
145                 150                 155                 160

Tyr Asn Ala Glu Trp Gln Phe Ser Ser Thr Pro Thr Cys Pro Ala Ser
                165                 170                 175

Gly Cys Pro Pro Leu Pro Asp Asp Gly Ile Val Phe Tyr Glu Tyr Tyr
            180                 185                 190

Gly Tyr Ala Gly Asp Arg His Thr Val Gly Pro Val Val Thr Lys Asp
        195                 200                 205

Ser Ser Gly Asn Tyr Pro Ser Pro Thr His Ala Arg Arg Arg Cys Arg
    210                 215                 220

Ala Leu Ser Gln Glu Ala Asp Pro Gly Glu Phe Val Ala Ile Cys Tyr
225                 230                 235                 240

Lys Ser Gly Thr Thr Gly Glu Ser His Trp Glu Tyr Lys Asn Ile
                245                 250                 255

Gly Lys Cys Pro Asp Pro Arg Cys Lys Pro Leu Glu Ala Asn Glu Ser
            260                 265                 270

Val His Tyr Glu Tyr Phe Thr Met Thr Asn Glu Thr Asp Lys Lys Lys
        275                 280                 285

Gly Pro Pro Ala Lys Val Gly Lys Ser Gly Lys Tyr Pro Glu His Thr
    290                 295                 300

Cys Val Lys Lys Val Cys Ser Lys Trp Pro Tyr Thr Cys Ser Ala Gly
305                 310                 315                 320

Gly Pro Ile Phe Gly Glu Cys Ile Gly Ala Thr Trp Asn Phe Thr Ala
                325                 330                 335

Leu Met Glu Cys Ile Asn Ala Arg Gly Cys Asp Glu Asn Asp Leu Phe
            340                 345                 350

```
Glu Leu Gly Phe Lys Glu Ile Met Val Arg Glu Gly Phe Ser Asp
            355                 360                 365

Ser Tyr Arg Asp Ala Tyr Val Leu Phe Tyr Ala Thr Gly Ser Lys Val
    370                 375                 380

Ser Ala Gln Cys Arg Gly Glu Thr Ala Arg Leu Glu Cys Ser Asn Gly
385                 390                 395                 400

Glu Trp His Asp Leu Gly Ala Lys Thr Val His Arg Ala Gln Arg Lys
                405                 410                 415

Asp Phe Ala His His Glu Glu Tyr Phe Leu Ile Leu Glu
            420                 425
```

<210> SEQ ID NO 33
<211> LENGTH: 1339
<212> TYPE: DNA
<213> ORGANISM: Artificial Sequence
<220> FEATURE:
<223> OTHER INFORMATION: TGM-e

<400> SEQUENCE: 33

```
acaaccacat ttatttcatt ccaagctgat gaaatatcct tcatagtgcg cggattcctt      60
cctttgtgca ccgatgcaca gttttagttc cgggatcatg ccattcaccg tcagagcact     120
ccagctgcac cgtttttacct ttacattccg cattcacttt cgaaccggtt gcgtagaacc    180
tgacgaagtc gtccttataa ctatcactgc cttcttcttc tctaaccata actccttcaa    240
agcccagttt atcaaacaag tcgtcactgt tgcaacccct tgcgtttaag cattcgtcaa    300
gtgcagtaaa attccactgg ccgtcaaggc attctccgaa aatcggccct ttaaccgaac    360
atgtatacgg tgacttgtcg caaaattttc tgacacacgt gtgttgaggg tactttccac    420
ccttgtctac ttccgcgggc gtgccttcct ttctgcccgt ctcgttggtc atggtgaagt    480
attcgtagtg aacagacacg ttagtttcca gtggcttgca tctaggatct gggcatttcc    540
ttatatgact gtagtaatcc caatgacttt cgccagtcgt accgcttttg tagcaaatgc    600
caacaaattc tcctggatca gcttttttggc tgagtgccct acaacgcctt cttgcatgcg    660
tttgtggagg gtaatttcca gaactgtcct tagatactgc tcgtccgacg gtatgtcgat    720
tgccagcgta tccgtagtat tcgtagaaga caattccatc atctggtagc ggtgggcaac    780
cactgggtgg gcatgttggt gtgctagaaa accgccattc agcattgtag cacatgccga    840
taatatggcc ttgaactttg ctgtcagcag gaaaattttt gcagattctt ttaatgtatg    900
ttagttcagg atattttcca gaagcatctg gatgaaccgt tatattaaaa ttgattcctg    960
catttactgt ggctttaaga tactcgtagg tgacagtatc gttcgtcggc aacggcgagc   1020
acctacggtc ttggcattct tgtactcctt gatagtagac ccattctgat ccaaggcaaa   1080
tgccgacgta cctacctgtc ttttcttctc catgcaatcc tttacaaaac cgtttaacat   1140
gtgtatgatc aggatacgct ccagagctgt cattttgtgc aggagtttcg tcgtttctag   1200
aacgttctgt taaatattta taggaggcgg tttcatcaga aaatggcata cagccgctgg   1260
cgtctgtagc tgcaacctcg agtaggccaa ttaatacaat cagcagcatt tcatcacgct   1320
aacgataaag ggccgttcc                                                 1339
```

<210> SEQ ID NO 34
<211> LENGTH: 1269
<212> TYPE: DNA
<213> ORGANISM: Artificial Sequence
<220> FEATURE:
<223> OTHER INFORMATION: TGM-e

<400> SEQUENCE: 34

```
atgctgctga ttgtattaat tggcctactc gaggttgcag ctacagacgc cagcggctgt    60
atgccatttt ctgatgaaac cgcctcctat aaatatttaa cagaacgttc tagaaacgac   120
gaaactcctg cacaaaatga cagctctgga gcgtatcctg atcatacaca tgttaaacgg   180
ttttgtaaag gattgcatgg agaagaaaag acaggtaggt acgtcggcat ttgccttgga   240
tcagaatggg tctactatca aggagtacaa gaatgccaag accgtaggtg ctcgccgttg   300
ccgacgaacg atactgtcac ctacgagtat cttaaagcca cagtaaatgc aggaatcaat   360
tttaatataa cggttcatcc agatgcttct ggaaaatatc ctgaactaac atacattaaa   420
agaatctgca aaaattttcc tgctgacagc aaagttcaag gccatattat cggcatgtgc   480
tacaatgctg aatggcggtt ttctagcaca ccaacatgcc cacccagtgg ttgcccaccg   540
ctaccagatg atggaattgt cttctacgaa tactacggat acgctggcaa tcgacatacc   600
gtcggacgag cagtatctaa ggacagttct ggaaattacc ctccacaaac gcatgcaaga   660
aggcgttgta gggcactcag ccaaaaagct gatccaggag aatttgttgg catttgctac   720
aaaagcggta cgactggcga agtcattgg gattactaca gtcatataag gaaatgccca   780
gatcctagat gcaagccact ggaaactaac gtgtctgttc actacgaata cttcaccatg   840
accaacgaga cgggcagaaa ggaaggcacg cccgcggaag tagacaaggg tggaaagtac   900
cctcaacaca cgtgtgtcag aaaattttgc gacaagtcac cgtatacatg ttcggttaaa   960
gggccgattt tcggagaatg ccttgacggc cagtggaatt ttactgcact tgacgaatgc  1020
ttaaacgcaa ggggttgcaa cagtgacgac ttgtttgata aactgggctt tgaaggagtt  1080
atggttagag aagaagaagg cagtgatagt tataaggacg acttcgtcag gttctacgca  1140
accggttcga aagtgaatgc ggaatgtaaa ggtaaaacgg tgcagctgga gtgctctgac  1200
ggtgaatggc atgatcccgg aactaaaact gtgcatcggt gcacaaagga aggaatccgc  1260
gcactatga                                                          1269
```

<210> SEQ ID NO 35
<211> LENGTH: 422
<212> TYPE: PRT
<213> ORGANISM: Artificial Sequence
<220> FEATURE:
<223> OTHER INFORMATION: TGM-e

<400> SEQUENCE: 35

```
Met Leu Leu Ile Val Leu Ile Gly Leu Leu Glu Val Ala Ala Thr Asp
1               5                   10                  15

Ala Ser Gly Cys Met Pro Phe Ser Asp Glu Thr Ala Ser Tyr Lys Tyr
            20                  25                  30

Leu Thr Glu Arg Ser Arg Asn Asp Glu Thr Pro Ala Gln Asn Asp Ser
        35                  40                  45

Ser Gly Ala Tyr Pro Asp His Thr His Val Lys Arg Phe Cys Lys Gly
    50                  55                  60

Leu His Gly Glu Glu Lys Thr Gly Arg Tyr Val Gly Ile Cys Leu Gly
65                  70                  75                  80

Ser Glu Trp Val Tyr Tyr Gln Gly Val Gln Glu Cys Gln Asp Arg Arg
                85                  90                  95

Cys Ser Pro Leu Pro Thr Asn Asp Thr Val Thr Tyr Glu Tyr Leu Lys
            100                 105                 110

Ala Thr Val Asn Ala Gly Ile Asn Phe Asn Ile Thr Val His Pro Asp
        115                 120                 125
```

Ala Ser Gly Lys Tyr Pro Glu Leu Thr Tyr Ile Lys Arg Ile Cys Lys
            130                 135                 140

Asn Phe Pro Ala Asp Ser Lys Val Gln Gly His Ile Ile Gly Met Cys
145                 150                 155                 160

Tyr Asn Ala Glu Trp Arg Phe Ser Ser Thr Pro Thr Cys Pro Pro Ser
                165                 170                 175

Gly Cys Pro Pro Leu Pro Asp Asp Gly Ile Val Phe Tyr Glu Tyr Tyr
            180                 185                 190

Gly Tyr Ala Gly Asn Arg His Thr Val Gly Arg Ala Val Ser Lys Asp
        195                 200                 205

Ser Ser Gly Asn Tyr Pro Pro Gln Thr His Ala Arg Arg Cys Arg
210                 215                 220

Ala Leu Ser Gln Lys Ala Asp Pro Gly Glu Phe Val Gly Ile Cys Tyr
225                 230                 235                 240

Lys Ser Gly Thr Thr Gly Glu Ser His Trp Asp Tyr Tyr Ser His Ile
                245                 250                 255

Arg Lys Cys Pro Asp Pro Arg Cys Lys Pro Leu Glu Thr Asn Val Ser
            260                 265                 270

Val His Tyr Glu Tyr Phe Thr Met Thr Asn Glu Thr Gly Arg Lys Glu
        275                 280                 285

Gly Thr Pro Ala Glu Val Asp Lys Gly Lys Tyr Pro Gln His Thr
290                 295                 300

Cys Val Arg Lys Phe Cys Asp Lys Ser Pro Tyr Thr Cys Ser Val Lys
305                 310                 315                 320

Gly Pro Ile Phe Gly Glu Cys Leu Asp Gly Gln Trp Asn Phe Thr Ala
                325                 330                 335

Leu Asp Glu Cys Leu Asn Ala Arg Gly Cys Asn Ser Asp Leu Phe
            340                 345                 350

Asp Lys Leu Gly Phe Glu Gly Val Met Val Arg Glu Glu Gly Ser
        355                 360                 365

Asp Ser Tyr Lys Asp Asp Phe Val Arg Phe Tyr Ala Thr Gly Ser Lys
370                 375                 380

Val Asn Ala Glu Cys Lys Gly Lys Thr Val Gln Leu Glu Cys Ser Asp
385                 390                 395                 400

Gly Glu Trp His Asp Pro Gly Thr Lys Thr Val His Arg Cys Thr Lys
                405                 410                 415

Glu Gly Ile Arg Ala Leu
            420

<210> SEQ ID NO 36
<211> LENGTH: 1870
<212> TYPE: DNA
<213> ORGANISM: Artificial Sequence
<220> FEATURE:
<223> OTHER INFORMATION: TGM-f

<400> SEQUENCE: 36
ttttgtccaa agaatcgttt attcaactgt ggcaaacact gagtttattc gtcataggtg      60
actccgctat cagtgcatcg tattttagcg aattttctct cattctcggc atgacgacgt     120
ccttgccatc caccttcaaa gcattcaaga tctgccgggt tacctttgca aagtgcttgt     180
attttcgaac caggtccgta aaatgtagaa acagtatcag gtttcttgta tactgccacc    240
gcaagacgtg tatcgactat agttgaggtg aatttcagat ccaaataaac ctcgtttata    300
ttgcagctcc cctgtggtgg acatggccat gtgttgcggt gcacccatcc gttcgcgccg    360

| | | |
|---|---|---|
| catttggaga tatccccttg agccctgctg tttacgtcta gtttcttgca aatcctccga | 420 | |
| gcatacgagc ccacagcgaa tttcccactc cagtctagta cggcaatatt tgcgaaatcg | 480 | |
| ttacttgttt gctcactttt aaagtacttg tattccacgg tgtcgttctc ggccaacggt | 540 | |
| aagcatccaa gaataggaca ttgtagcacc gtcgcttcat tctccttcac ccattcgcct | 600 | |
| ttgctgcatc ttccagcgat ttctcctaag ttttttgttat cgccagttgc cttcttacaa | 660 | |
| aacatctttg cagacgtgcg ttcggggtat tttccagacc gtggctttac agtggaggtg | 720 | |
| cttagtgtat agtagcctgt gcgtgatata ttgagatact catatcttac ggtgtcgttg | 780 | |
| tccgtaagag gggcgcattc acgcccaggg cattccggta tgatttggta cttttctggc | 840 | |
| ttccattggc gattgctgca ttgtgcaata attgtccctg ttttttcgcc tattctagtc | 900 | |
| ggtatcttac agatgactat cgcaaacgtg ccgtcagggt attctccgct ctgcggtgtc | 960 | |
| gcttcctttg cgacgacagt ttggtcagga gacattgtgt attggagata cttatacgta | 1020 | |
| acggtactgt tggctttata tgttatggta cagccaggaa ctgggcactg ttttatatta | 1080 | |
| tgatagtaca cccaccgact ttcaccagta tcacttcttt cgtggcaaat ggcgacaagt | 1140 | |
| tccccttgat caacctttac gctccgtgct tggcaatgcc ttcttgcatg cgtctgtgga | 1200 | |
| gggtaatttc cagaactgtc cttagttact gcttgtccga cgacatctcg actcccagcg | 1260 | |
| tattcatagt attcgtgccg gaatttgtca ttgtcttgta tcggtgggca accatagggt | 1320 | |
| gggcatactg gtgcgctgga gaacctccat tcagcattgt agcacatgcc gacaataaca | 1380 | |
| cctcgaactt gctgtttgc aggaaaattt ttgcatattc ttcttatgta tgttagttca | 1440 | |
| ggatattttc cgctgtcatc tggattggca cttgtatcat aactgattct cgaagaattt | 1500 | |
| agagtagctt tacgatactc gtagctgaca gtatcgctct cagacaacgg cgagcatcta | 1560 | |
| cggtctcggc attcttgtac tcccatataa tagacccatt ccgatcgatg gcacaggccg | 1620 | |
| atgaactcac ctgtcttatc ttctccatgc aatcctttac aaaaccgttt cacgtgcgta | 1680 | |
| tactcaggat acattccaga actgtccttt cgcgcaggtg tttcctcttt attagaagtt | 1740 | |
| tgtgcaaaat attggtaggt gtcagtttct tcagataatg gcatgcagct gttgtcgcct | 1800 | |
| gcagccgaag cctcgagaag gccaattact acaatcagca gcatttcact caaacttggg | 1860 | |
| taattaaacc | 1870 | |

<210> SEQ ID NO 37
<211> LENGTH: 1800
<212> TYPE: DNA
<213> ORGANISM: Artificial Sequence
<220> FEATURE:
<223> OTHER INFORMATION: TGM-f

<400> SEQUENCE: 37

| | | |
|---|---|---|
| atgctgctga ttgtagtaat tggccttctc gaggcttcgg ctgcaggcga caacagctgc | 60 | |
| atgccattat ctgaagaaac tgacacctac caatattttg cacaaacttc taataaagag | 120 | |
| gaaacacctg cgcgaaagga cagttctgga atgtatcctg agtatacgca cgtgaaacgg | 180 | |
| ttttgtaaag gattgcatgg agaagataag acaggtgagt tcatcggcct gtgccatcga | 240 | |
| tcggaatggg tctattatat gggagtacaa gaatgccgag accgtagatg ctcgccgttg | 300 | |
| tctgagagcg atactgtcag ctacgagtat cgtaaagcta ctctaaattc ttcgagaatc | 360 | |
| agttatgata caagtgccaa tccagatgac agcggaaaat atcctgaact aacatacata | 420 | |
| agaagaatat gcaaaaattt tcctgcaaac agcaaagttc gaggtgttat tgtcggcatg | 480 | |

-continued

```
tgctacaatg ctgaatggag gttctccagc gcaccagtat gcccacccta tggttgccca    540
ccgatacaag acaatgacaa attccggcac gaatactatg aatacgctgg gagtcgagat    600
gtcgtcggac aagcagtaac taaggacagt tctggaaatt accctccaca gacgcatgca    660
agaaggcatt gccaagcacg gagcgtaaag gttgatcaag gggaacttgt cgccatttgc    720
cacgaaagaa gtgatactgg tgaaagtcgg tgggtgtact atcataatat aaaacagtgc    780
ccagttcctg gctgtaccat aacatataaa gccaacagta ccgttacgta taagtatctc    840
caatacacaa tgtctcctga ccaaactgtc gtcgcaaagg aagcgacacc gcagagcgga    900
gaatccctg acggcacgtt tgcgatagtc atctgtaaga taccgactag aataggcgaa    960
aaaacaggga caattattgc acaatgcagc aatcgccaat ggaagccaga aaagtaccaa   1020
atcataccgg aatgccctgg gcgtgaatgc gcccctctta cggacaacga caccgtaaga   1080
tatgagtatc tcaatatatc acgcacaggc tactatacac taagcacctc cactgtaaag   1140
ccacggtctg gaaataccc cgaacgcacg tctgcaaaga tgttttgtaa gaaggcaact   1200
ggcgataaca aaaacttagg agaaatcgct ggaagatgca gcaaaggcga atgggtgaag   1260
gagaatgaag cgacggtgct acaatgtcct attcttggat gcttaccgtt ggccgagaac   1320
gacaccgtgg aatacaagta ctttaaaagt gagcaaacaa gtaacgattt cgcaaatatt   1380
gccgtactag actggagtgg gaaattcgct gtgggctcgt atgctcggag gatttgcaag   1440
aaactagacg taaacagcag ggctcaaggg gatatctcca aatgcggcgc gaacggatgg   1500
gtgcaccgca acacatggcc atgtccacca caggggagct gcaatataaa cgaggtttat   1560
ttggatctga aattcaccctc aactatagtc gatacacgtc ttgcggtggc agtatacaag   1620
aaacctgata ctgtttctac attttacgga cctggttcga aaatacaagc actttgcaaa   1680
ggtaacccgg cagatcttga atgctttgaa ggtggatggc aaggacgtcg tcatgccgag   1740
aatgagagaa aattcgctaa aatacgatgc actgatagcg gagtcaccta tgacgaataa   1800
```

<210> SEQ ID NO 38
<211> LENGTH: 599
<212> TYPE: PRT
<213> ORGANISM: Artificial Sequence
<220> FEATURE:
<223> OTHER INFORMATION: TGM-f

<400> SEQUENCE: 38

```
Met Leu Leu Ile Val Ile Gly Leu Leu Glu Ala Ser Ala Ala Gly
1               5                   10                  15

Asp Asn Ser Cys Met Pro Leu Ser Glu Glu Thr Asp Thr Tyr Gln Tyr
            20                  25                  30

Phe Ala Gln Thr Ser Asn Lys Glu Glu Thr Pro Ala Arg Lys Asp Ser
        35                  40                  45

Ser Gly Met Tyr Pro Glu Tyr Thr His Val Lys Arg Phe Cys Lys Gly
    50                  55                  60

Leu His Gly Glu Asp Lys Thr Gly Glu Phe Ile Gly Leu Cys His Arg
65                  70                  75                  80

Ser Glu Trp Val Tyr Tyr Met Gly Val Gln Glu Cys Arg Asp Arg
                85                  90                  95

Cys Ser Pro Leu Ser Glu Ser Asp Thr Val Ser Tyr Glu Tyr Arg Lys
                100                 105                 110

Ala Thr Leu Asn Ser Ser Arg Ile Ser Tyr Asp Thr Ser Ala Asn Pro
            115                 120                 125

Asp Asp Ser Gly Lys Tyr Pro Glu Leu Thr Tyr Ile Arg Arg Ile Cys
```

```
                130                 135                 140
Lys Asn Phe Pro Ala Asn Ser Lys Val Arg Gly Val Ile Val Gly Met
145                 150                 155                 160

Cys Tyr Asn Ala Glu Trp Arg Phe Ser Ser Ala Pro Val Cys Pro Pro
                165                 170                 175

Tyr Gly Cys Pro Pro Ile Gln Asp Asn Asp Lys Phe Arg His Glu Tyr
                180                 185                 190

Tyr Glu Tyr Ala Gly Ser Arg Asp Val Val Gly Gln Ala Val Thr Lys
                195                 200                 205

Asp Ser Ser Gly Asn Tyr Pro Pro Gln Thr His Ala Arg Arg His Cys
                210                 215                 220

Gln Ala Arg Ser Val Lys Val Asp Gln Gly Glu Leu Val Ala Ile Cys
225                 230                 235                 240

His Glu Arg Ser Asp Thr Gly Glu Ser Arg Trp Val Tyr Tyr His Asn
                245                 250                 255

Ile Lys Gln Cys Pro Val Pro Gly Cys Thr Ile Thr Tyr Lys Ala Asn
                260                 265                 270

Ser Thr Val Thr Tyr Lys Tyr Leu Gln Tyr Thr Met Ser Pro Asp Gln
                275                 280                 285

Thr Val Val Ala Lys Glu Ala Thr Pro Gln Ser Gly Glu Tyr Pro Asp
                290                 295                 300

Gly Thr Phe Ala Ile Val Ile Cys Lys Ile Pro Thr Arg Ile Gly Glu
305                 310                 315                 320

Lys Thr Gly Thr Ile Ile Ala Gln Cys Ser Asn Arg Gln Trp Lys Pro
                325                 330                 335

Glu Lys Tyr Gln Ile Ile Pro Glu Cys Pro Gly Arg Glu Cys Ala Pro
                340                 345                 350

Leu Thr Asp Asn Asp Thr Val Arg Tyr Glu Tyr Leu Asn Ile Ser Arg
                355                 360                 365

Thr Gly Tyr Tyr Thr Leu Ser Thr Ser Thr Val Lys Pro Arg Ser Gly
                370                 375                 380

Lys Tyr Pro Glu Arg Thr Ser Ala Lys Met Phe Cys Lys Lys Ala Thr
385                 390                 395                 400

Gly Asp Asn Lys Asn Leu Gly Glu Ile Ala Gly Arg Cys Ser Lys Gly
                405                 410                 415

Glu Trp Val Lys Glu Asn Glu Ala Thr Val Leu Gln Cys Pro Ile Leu
                420                 425                 430

Gly Cys Leu Pro Leu Ala Glu Asn Asp Thr Val Glu Tyr Lys Tyr Phe
                435                 440                 445

Lys Ser Glu Gln Thr Ser Asn Asp Phe Ala Asn Ile Ala Val Leu Asp
                450                 455                 460

Trp Ser Gly Lys Phe Ala Val Gly Ser Tyr Ala Arg Arg Ile Cys Lys
465                 470                 475                 480

Lys Leu Asp Val Asn Ser Arg Ala Gln Gly Asp Ile Ser Lys Cys Gly
                485                 490                 495

Ala Asn Gly Trp Val His Arg Asn Thr Trp Pro Cys Pro Pro Gln Gly
                500                 505                 510

Ser Cys Asn Ile Asn Glu Val Tyr Leu Asp Leu Lys Phe Thr Ser Thr
                515                 520                 525

Ile Val Asp Thr Arg Leu Ala Val Ala Val Tyr Lys Lys Pro Asp Thr
                530                 535                 540

Val Ser Thr Phe Tyr Gly Pro Gly Ser Lys Ile Gln Ala Leu Cys Lys
545                 550                 555                 560
```

```
Gly Asn Pro Ala Asp Leu Glu Cys Phe Glu Gly Gly Trp Gln Gly Arg
                565                 570                 575
Arg His Ala Glu Asn Glu Arg Lys Phe Ala Lys Ile Arg Cys Thr Asp
        580                 585                 590
Ser Gly Val Thr Tyr Asp Glu
        595
```

<210> SEQ ID NO 39
<211> LENGTH: 1870
<212> TYPE: DNA
<213> ORGANISM: Artificial Sequence
<220> FEATURE:
<223> OTHER INFORMATION: TGM-g

<400> SEQUENCE: 39

| | | | | | |
|---|---|---|---|---|---|
| ttttgtccaa | agaatcgttt | attcaactgt | ggcaaacact | gagtttattc | gtcataggtg | 60 |
| actccgctat | cagtgcatcg | tattttagcg | aattttctct | cattctcggc | atgacgacgt | 120 |
| ccttgccatc | caccttcaaa | gcattcaaga | tctgccgggt | tacctttgca | aagtgcttgt | 180 |
| attttcgaac | caggtccgta | atatggtgaa | acagtaccag | gtttctggta | tactgccacc | 240 |
| gcaagacttg | tatggactat | agttgaggtg | aattctcgat | ccagaaaaac | atcgcttata | 300 |
| tcgcaactcc | cgcgtggggg | gcatggccat | gtgttgctgt | gctcccatcc | gttctccccg | 360 |
| catttggaga | tatccccttg | agcctcgctt | ttttcgtcca | gttccttgca | aatcctccaa | 420 |
| gcatacgagc | ccacagcgaa | ctttccactc | caatctagtg | gggcaatatt | tcgtgcgcg | 480 |
| atatttggat | gttcactttt | gaagtacttg | tattccacgg | tgtcgttctc | gtgcaacggt | 540 |
| aggcatccaa | gaataggaca | ttgtagcacc | gtcgcttcat | tctccttcac | ccattcgcct | 600 |
| tgctgcatc | ttccagcgat | ttcccctaag | ttttgttat | cgtcagttgc | cttcttacaa | 660 |
| aacatctttg | cagacgtgcc | ttcggggtat | tttccagacc | gtggctttac | cttggaggtg | 720 |
| cttagtgtat | agtagcctgt | gcgtgatata | ttgagatact | catatcttac | ggtgtcgttg | 780 |
| tccgtaagag | gggcgcattc | acgcccaggg | cattccggta | cgatttggta | cttttccggc | 840 |
| ttccatttgc | gattgctgca | ttgtgcaaaa | attgtccctg | ttttttcgcc | tattctagtc | 900 |
| ggtatcttac | agatgactat | cgcaaacgtg | ccgtcagggt | attctccgcc | ctgcggtgtc | 960 |
| gcttcctttg | cgacgacagt | ttggtcagga | gatattgtgt | attggagata | cttatacgta | 1020 |
| acggtactgt | tgtcttcata | tgctgtggta | cagccaggat | ctgggcattg | ttttatatta | 1080 |
| agatagtaca | cccaccgact | ttcaccagta | ctatctcttt | cgaggcaaat | ggcgacaaat | 1140 |
| tccccttgac | catcctttcc | gctccctgcg | ctgcaacgcc | ttcttgcatg | cgtctgtgga | 1200 |
| gggtaatttc | cagaactgtc | cttagttgct | gctggtccga | gttttctcg | actcccagcg | 1260 |
| tatttatagt | attcgtgccg | gaaattgtca | ttgtcttgta | tcggtgggca | accgtagggt | 1320 |
| gggcattctg | gtgtgctgga | aaacctccac | tcagcattgt | agcacatgcc | gacaatgaga | 1380 |
| cctcgaattt | tgctgtctac | agaaaaattt | ttgcaggttc | ttctaatgta | tgttagttca | 1440 |
| ggatattttc | cgctgctatc | tggattggca | tttgtatcat | aactgattct | cgaagaattt | 1500 |
| agagtagctt | tacgatactc | gtagctgaca | gtatcgctct | cagacaacgg | cgagcatcta | 1560 |
| cggtctcggc | attcttttac | tcccatataa | tagacccatt | ctgatcgatg | gcacaggccg | 1620 |
| atgaactcac | ctgtcttatc | ttctccatgc | aatcctttac | aaaaccgttt | cacgtgcgta | 1680 |
| tactcaggat | acattccaga | actgtccttt | cgcgcaggtg | tttcctcttt | attagaagtt | 1740 |
| tgtgcaaaat | attggtaggt | gtcagttttct | tcagataatg | gcatgcagct | gttgtcgcct | 1800 |

```
gcagccgaag cctcgagaag gccaattact acaatcagca gcatttcact caaacttggg    1860
taattaaacc                                                            1870

<210> SEQ ID NO 40
<211> LENGTH: 1800
<212> TYPE: DNA
<213> ORGANISM: Artificial Sequence
<220> FEATURE:
<223> OTHER INFORMATION: TGM-g

<400> SEQUENCE: 40
atgctgctga ttgtagtaat tggccttctc gaggcttcgg ctgcaggcga caacagctgc      60
atgccattat ctgaagaaac tgacacctac caatattttg cacaaacttc taataaagag     120
gaaacacctg cgcgaaagga cagttctgga atgtatcctg agtatacgca cgtgaaacgg     180
ttttgtaaag gattgcatgg agaagataag acaggtgagt catcggcct gtgccatcga     240 tcagaatggg tctattatat gggagtaaaa gaatgccgag accgtagatg ctcgccgttg     300
tctgagagcg atactgtcag ctacgagtat cgtaaagcta ctctaaattc ttcgagaatc     360
agttatgata caaatgccaa tccagatagc agcggaaaat atcctgaact aacatacatt     420
agaagaacct gcaaaaattt ttctgtagac agcaaaattc gaggtctcat tgtcggcatg     480
tgctacaatg ctgagtggag gttttccagc acaccagaat gcccacccta cggttgccca     540
ccgatacaag acaatgacaa tttccggcac gaatactata aatacgctgg gagtcgagaa     600
aaactcggac cagcagcaac taaggacagt tctggaaatt accctccaca gacgcatgca     660
agaaggcgtt gcagcgcagg gagcggaaag gatggtcaag gggaatttgt cgccatttgc     720
ctcgaaagag atagtactgg tgaaagtcgg tgggtgtact atcttaatat aaaacaatgc     780
ccagatcctg gctgtaccac agcatatgaa gacaacagta ccgttacgta taagtatctc     840
caatacacaa tatctcctga ccaaactgtc gtcgcaaagg aagcgacacc gcagggcgga     900 gaatacctg acggcacgtt tgcgatagtc atctgtaaga taccgactag aataggcgaa     960
aaaacaggga caatttttgc acaatgcagc aatcgcaaat ggaagccgga aaagtaccaa    1020
atcgtaccgg aatgccctgg gcgtgaatgc gcccctctta cggacaacga caccgtaaga    1080
tatgagtatc tcaatatatc acgcacaggc tactatacac taagcacctc caaggtaaag    1140
ccacggtctg gaaatacccc gaaggcacg tctgcaaaga tgtttttgtaa gaaggcaact    1200 gacgataaca aaaacttagg ggaaatcgct ggaagatgca gcaaaggcga atgggtgaag    1260
gagaatgaag cgacggtgct acaatgtcct attcttggat gcctaccgtt gcacgagaac    1320
gacaccgtgg aatacaagta cttcaaaagt gaacatccaa atatcgcgca cgaaaatatt    1380
gccccactag attggagtgg aaagttcgct gtgggctcgt atgcttggag gatttgcaag    1440
gaactggacg aaaaaagcga ggctcaaggg gatatctcca atgcgggga gaacggatgg    1500 gagcacagca acatggcc atgcccccca cgcgggagtt gcgatataag cgatgttttt    1560
ctggatcaga aattcacctc aactatagtc catacaagtc ttgcggtggc agtataccag    1620
aaacctggta ctgtttcacc atattacgga cctggttcga aaatacaagc actttgcaaa    1680
ggtaacccgg cagatcttga atgctttgaa ggtggatggc aaggacgtcg tcatgccgag    1740
aatgagagaa aattcgctaa aatacgatgc actgatagcg gagtcaccta tgacgaataa    1800

<210> SEQ ID NO 41
<211> LENGTH: 599
<212> TYPE: PRT
```

<213> ORGANISM: Artificial Sequence
<220> FEATURE:
<223> OTHER INFORMATION: TGM-g

<400> SEQUENCE: 41

```
Met Leu Leu Ile Val Val Ile Gly Leu Leu Glu Ala Ser Ala Ala Gly
1               5                   10                  15

Asp Asn Ser Cys Met Pro Leu Ser Glu Glu Thr Asp Thr Tyr Gln Tyr
            20                  25                  30

Phe Ala Gln Thr Ser Asn Lys Glu Thr Pro Ala Arg Lys Asp Ser
        35                  40                  45

Ser Gly Met Tyr Pro Glu Tyr Thr His Val Lys Arg Phe Cys Lys Gly
    50                  55                  60

Leu His Gly Glu Asp Lys Thr Gly Glu Phe Ile Gly Leu Cys His Arg
65                  70                  75                  80

Ser Glu Trp Val Tyr Tyr Met Gly Val Lys Glu Cys Arg Asp Arg Arg
                85                  90                  95

Cys Ser Pro Leu Ser Glu Ser Asp Thr Val Ser Tyr Gly Tyr Arg Lys
                100                 105                 110

Ala Thr Leu Asn Ser Ser Arg Ile Ser Tyr Asp Thr Asn Ala Asn Pro
            115                 120                 125

Asp Ser Ser Gly Lys Tyr Pro Glu Leu Thr Tyr Ile Arg Arg Thr Cys
    130                 135                 140

Lys Asn Phe Ser Val Asp Ser Lys Ile Arg Gly Leu Ile Val Gly Met
145                 150                 155                 160

Cys Tyr Asn Ala Glu Trp Arg Phe Ser Ser Thr Pro Glu Cys Pro Pro
                165                 170                 175

Tyr Gly Cys Pro Pro Ile Gln Asp Asn Asp Asn Phe Arg His Glu Tyr
                180                 185                 190

Tyr Lys Tyr Ala Gly Ser Arg Glu Lys Leu Gly Pro Ala Ala Thr Lys
            195                 200                 205

Asp Ser Ser Gly Asn Tyr Pro Pro Gln Thr His Ala Arg Arg Arg Cys
    210                 215                 220

Ser Ala Gly Ser Gly Lys Asp Gly Gln Gly Glu Phe Val Ala Ile Cys
225                 230                 235                 240

Leu Glu Arg Asp Ser Thr Gly Glu Ser Arg Trp Val Tyr Tyr Leu Asn
                245                 250                 255

Ile Lys Gln Cys Pro Asp Pro Gly Cys Thr Thr Ala Tyr Glu Asp Asn
                260                 265                 270

Ser Thr Val Thr Tyr Lys Tyr Leu Gln Tyr Thr Ile Ser Pro Asp Gln
            275                 280                 285

Thr Val Val Ala Lys Glu Ala Thr Pro Gln Gly Gly Glu Tyr Pro Asp
    290                 295                 300

Gly Thr Phe Ala Ile Val Ile Cys Lys Ile Pro Thr Arg Ile Gly Glu
305                 310                 315                 320

Lys Thr Gly Thr Ile Phe Ala Gln Cys Ser Asn Arg Lys Trp Lys Pro
                325                 330                 335

Glu Lys Tyr Gln Ile Val Pro Glu Cys Pro Gly Arg Glu Cys Ala Pro
                340                 345                 350

Leu Thr Asp Asn Asp Thr Val Arg Tyr Glu Tyr Leu Asn Ile Ser Arg
            355                 360                 365

Thr Gly Tyr Tyr Thr Leu Ser Thr Ser Lys Val Lys Pro Arg Ser Gly
    370                 375                 380

Lys Tyr Pro Glu Gly Thr Ser Ala Lys Met Phe Cys Lys Lys Ala Thr
```

```
                385                 390                 395                 400
Asp Asp Asn Lys Asn Leu Gly Glu Ile Ala Gly Arg Cys Ser Lys Gly
                405                 410                 415

Glu Trp Val Lys Glu Asn Glu Ala Thr Val Leu Gln Cys Pro Ile Leu
            420                 425                 430

Gly Cys Leu Pro Leu His Glu Asn Asp Thr Val Glu Tyr Lys Tyr Phe
        435                 440                 445

Lys Ser Glu His Pro Asn Ile Ala His Glu Asn Ile Ala Pro Leu Asp
    450                 455                 460

Trp Ser Gly Lys Phe Ala Val Gly Ser Tyr Ala Trp Arg Ile Cys Lys
465                 470                 475                 480

Glu Leu Asp Glu Lys Ser Glu Ala Gln Gly Asp Ile Ser Lys Cys Gly
                485                 490                 495

Glu Asn Gly Trp Glu His Ser Asn Thr Trp Pro Cys Pro Pro Arg Gly
            500                 505                 510

Ser Cys Asp Ile Ser Asp Val Phe Leu Asp Gln Lys Phe Thr Ser Thr
        515                 520                 525

Ile Val His Thr Ser Leu Ala Val Ala Val Tyr Gln Lys Pro Gly Thr
    530                 535                 540

Val Ser Pro Tyr Tyr Gly Pro Gly Ser Lys Ile Gln Ala Leu Cys Lys
545                 550                 555                 560

Gly Asn Pro Ala Asp Leu Glu Cys Phe Glu Gly Gly Trp Gln Gly Arg
                565                 570                 575

Arg His Ala Glu Asn Glu Arg Lys Phe Ala Lys Ile Arg Cys Thr Asp
            580                 585                 590

Ser Gly Val Thr Tyr Asp Glu
        595

<210> SEQ ID NO 42
<211> LENGTH: 851
<212> TYPE: DNA
<213> ORGANISM: Artificial Sequence
<220> FEATURE:
<223> OTHER INFORMATION: TGM-h

<400> SEQUENCE: 42
tttatattca aaatatttta tgcacttcag ctgtgaagac tgtctcattc gcaaagcgct      60
tttctgccgt ccgctgtaac ccaatggccg ccgtcagcac atgttaactt cacagattca    120
cctttgcact cgcagtgac tctcgaaccg ggacgataat gcctgtatgt attgtcttcg     180
gaaaattttg ctggctgatt tacccagtat gaaatatcac tgaacattag cttctcaagc    240
agatattctt cgtcacatcc tgctgcgaat cgacagtctg gcaaatttt aagcttccac     300 tctgaatcca agcactctgc gtaggtctcc gcttgagcta gactattcct tggaagctca    360
ttgcaatacc ttctaactag tgtttgttcg ggatactttc gcttccgtc cgggtttgta     420 agtgtaccca tgccctttcc ttcagccgct tttgtgtaat attcatagct cacagaaaca    480 ctcttttca gaggctcgca ccgagggtcc gggcatgccg ttatattacg atagtacatc     540
cattgacttc cacgtctttg gtagcaaatg gcgacaaata ccctgggtc agcttttta     600 ctgagagcct acaatgcgc tcttgcatgc gtctgcggag ataatttcc agaagtgtcc     660 ttagttgctg cttccccgac ggtgtgacga ttttcaacgt attcgtaata ttcgtaccac    720
acagtttcat tgtccggaag aggtaggcaa cttgatccaa cagcttcaac cagtccgata    780
gcaacgaata ataggagcat cttgatggag cgtcgatgag cacaatggtc tcaaacttgg    840
```
gtaattaaac c 851

<210> SEQ ID NO 43
<211> LENGTH: 756
<212> TYPE: DNA
<213> ORGANISM: Artificial Sequence
<220> FEATURE:
<223> OTHER INFORMATION: TGM-h

<400> SEQUENCE: 43

```
atgctcctat tattcgttgc tatcggactg gttgaagctg ttggatcaag ttgcctacct      60
cttccggaca tgaaactgt gtggtacgaa tattacgaat acgttgaaaa tcgtcacacc     120
gtcggggaag cagcaactaa ggacacttct ggaaattatc ctccgcagac gcatgcaaga    180
gcgcattgta aggctctcag taaaaaagct gacccagggg tatttgtcgc catttgctac    240
caaagacgtg gaagtcaatg gatgtactat cgtaatataa cggcatgccc ggaccctcgg    300
tgcgagcctc tgaaaaagag tgtttctgtg agctatgaat attacacaaa agcggctgaa    360
ggaaagggca tgggtacact tacaaacccg gacggaagcg gaaagtatcc cgaacaaaca    420
ctagttagaa ggtattgcaa tgagcttcca aggaatagtc tagctcaagc ggagacctac    480
gcagagtgct tggattcaga gtggaagctt aaaaatttgc cagactgtcg attcgcagca    540
ggatgtgacg aagaatatct gcttgagaag ctaatgttca gtgatatttc atactgggta    600
aatcagccag caaatttttc gaagacaat acatacaggc attatcgtcc cggttcgaga     660
gtcactgcga agtgcaaagg tgaatctgtg aagttaacat gtgctgacgg cggccattgg    720
gttacagcgg acggcagaaa agcgctttgc gaatga                              756
```

<210> SEQ ID NO 44
<211> LENGTH: 251
<212> TYPE: PRT
<213> ORGANISM: Artificial Sequence
<220> FEATURE:
<223> OTHER INFORMATION: TGM-h

<400> SEQUENCE: 44

```
Met Leu Leu Leu Phe Val Ala Ile Gly Leu Val Glu Ala Val Gly Ser
1               5                   10                  15

Ser Cys Leu Pro Leu Pro Asp Asn Glu Thr Val Trp Tyr Glu Tyr Tyr
            20                  25                  30

Glu Tyr Val Glu Asn Arg His Thr Val Gly Glu Ala Ala Thr Lys Asp
        35                  40                  45

Thr Ser Gly Asn Tyr Pro Pro Gln Thr His Ala Arg Ala His Cys Lys
    50                  55                  60

Ala Leu Ser Lys Lys Ala Asp Pro Gly Val Phe Val Ala Ile Cys Tyr
65                  70                  75                  80

Gln Arg Arg Gly Ser Gln Trp Met Tyr Tyr Arg Asn Ile Thr Ala Cys
                85                  90                  95

Pro Asp Pro Arg Cys Glu Pro Leu Lys Lys Ser Val Ser Val Ser Tyr
            100                 105                 110

Glu Tyr Tyr Thr Lys Ala Ala Glu Gly Lys Gly Met Gly Thr Leu Thr
        115                 120                 125

Asn Pro Asp Gly Ser Gly Lys Tyr Pro Glu Gln Thr Leu Val Arg Arg
    130                 135                 140

Tyr Cys Asn Glu Leu Pro Arg Asn Ser Leu Ala Gln Ala Glu Thr Tyr
145                 150                 155                 160

Ala Glu Cys Leu Asp Ser Glu Trp Lys Leu Lys Asn Leu Pro Asp Cys
```

```
            165                 170                 175
Arg Phe Ala Ala Gly Cys Asp Glu Glu Tyr Leu Leu Glu Lys Leu Met
                180                 185                 190
Phe Ser Asp Ile Ser Tyr Trp Val Asn Gln Pro Ala Lys Phe Ser Glu
            195                 200                 205
Asp Asn Thr Tyr Arg His Tyr Arg Pro Gly Ser Arg Val Thr Ala Lys
        210                 215                 220
Cys Lys Gly Glu Ser Val Lys Leu Thr Cys Ala Asp Gly Gly His Trp
225                 230                 235                 240
Val Thr Ala Asp Gly Arg Lys Ala Leu Cys Glu
                245                 250
```

<210> SEQ ID NO 45
<211> LENGTH: 844
<212> TYPE: DNA
<213> ORGANISM: Artificial Sequence
<220> FEATURE:
<223> OTHER INFORMATION: TGM-i

<400> SEQUENCE: 45

```
gtttaattac ccaagtttga gaactaacgc atttaagtta aatgtggttc tccctaattg      60
cagtcgcagt tttcaacgtt gcaggagcaa gtgatggttg cctgccacta tctgaggaaa     120
cggccactta tgaatattat gcatacagcg ggagtcggta tgttgacggt aaccccacag     180
aaaaggacag ttccggaagg tatcctcatg gcacacatgc aagcgatttt gcaaaggct     240
cagatgaaga ggcagggttg ttcgtagcca tgcgttaaa atatagatgg gtgtactaca     300
aggacgtaaa gccgtgtcca gactttaggt gtcaaccgct gacgccaaat gaaactatca     360
gcaattacca gtacctcaaa gaaaccacca attctggagg agaaagcttt gaagtcgtcc     420
aaccggatgc cgacggaaaa tatcctgagc tgacgtacat aaggagaacg tgcaatgagt     480
ttcccacaga cagaaagcta caaagagata tcgccggcct ttgctacaaa gccgaatggt     540
ttctacgaac ctgtccgact cccggaaatt gctacgacga cgatatacgc acaaagttga     600
agtaccaagg atattcattt gactatgaaa ctgccgaagt gacttactca ttcggtaatg     660
acggagcgca ttatttcata gagggctctc aggtcacagg aatttgtaac ggttatcaag     720
taccctatg gtgccaggat ggtgaatgga tcggagaggt aaagaacatt tcctgcgata     780
tgatgaacgc acagtagcat cgtacagcca gtgtctgcgg acacaataa atattttatt     840
tctt                                                                 844
```

<210> SEQ ID NO 46
<211> LENGTH: 756
<212> TYPE: DNA
<213> ORGANISM: Artificial Sequence
<220> FEATURE:
<223> OTHER INFORMATION: TGM-i

<400> SEQUENCE: 46

```
atgtggttct ccctaattgc agtcgcagtt ttcaacgttg caggagcaag tgatggttgc      60
ctgccactat ctgaggaaac ggccacttat gaatattatg catacagcgg gagtcggtat     120
gttgacggta accccacaga aaaggacagt tccggaaggt atcctcatgg cacacatgcc     180
aagcgatttt gcaaaggctc agatgaagag gcagggttgt tcgtagccat gcgttaaaa     240
tatagatggg tgtactacaa ggacgtaaag ccgtgtccag actttaggtg tcaaccgctg     300
acgccaaatg aaactatcag caattaccag tacctcaaag aaaccaccaa ttctggagga     360
```

-continued

```
gaaagctttg aagtcgtcca accggatgcc gacggaaaat atcctgagct gacgtacata      420
aggagaacgt gcaatgagtt tcccacagac agaaagctac aaagagatat cgccggcctt      480
tgctacaaag ccgaatggtt tctacgaacc tgtccgactc ccggaaattg ctacgacgac      540
gatatacgca caaagttgaa gtaccaagga tattcatttg actatgaaac tgccgaagtg      600
acttactcat tcggtaatga cggagcgcat tatttcatag agggctctca ggtcacagga      660
atttgtaacg gttatcaagt accctatgg tgccaggatg gtgaatggat cggagaggta       720
aagaacattt cctgcgatat gatgaacgca cagtag                                756
```

<210> SEQ ID NO 47
<211> LENGTH: 251
<212> TYPE: PRT
<213> ORGANISM: Artificial Sequence
<220> FEATURE:
<223> OTHER INFORMATION: TGM-i

<400> SEQUENCE: 47

Met Trp Phe Ser Leu Ile Ala Val Ala Val Phe Asn Val Ala Gly Ala
1               5                   10                  15

Ser Asp Gly Cys Leu Pro Leu Ser Glu Glu Thr Ala Thr Tyr Glu Tyr
            20                  25                  30

Tyr Ala Tyr Ser Gly Ser Arg Tyr Val Asp Gly Asn Pro Thr Glu Lys
        35                  40                  45

Asp Ser Ser Gly Arg Tyr Pro His Gly Thr His Ala Lys Arg Phe Cys
    50                  55                  60

Lys Gly Ser Asp Glu Glu Ala Gly Leu Phe Val Ala Ile Cys Val Lys
65                  70                  75                  80

Tyr Arg Trp Val Tyr Tyr Lys Asp Val Lys Pro Cys Pro Asp Phe Arg
                85                  90                  95

Cys Gln Pro Leu Thr Pro Asn Glu Thr Ile Ser Asn Tyr Gln Tyr Leu
            100                 105                 110

Lys Glu Thr Thr Asn Ser Gly Gly Glu Ser Phe Glu Val Val Gln Pro
        115                 120                 125

Asp Ala Asp Gly Lys Tyr Pro Glu Leu Thr Tyr Ile Arg Arg Thr Cys
    130                 135                 140

Asn Glu Phe Pro Thr Asp Arg Lys Leu Gln Arg Asp Ile Ala Gly Leu
145                 150                 155                 160

Cys Tyr Lys Ala Glu Trp Phe Leu Arg Thr Cys Pro Thr Pro Gly Asn
                165                 170                 175

Cys Tyr Asp Asp Ile Arg Thr Lys Leu Lys Tyr Gln Gly Tyr Ser
            180                 185                 190

Phe Asp Tyr Glu Thr Ala Glu Val Thr Tyr Ser Phe Gly Asn Asp Gly
        195                 200                 205

Ala His Tyr Phe Ile Glu Gly Ser Gln Val Thr Gly Ile Cys Asn Gly
    210                 215                 220

Tyr Gln Val Pro Leu Trp Cys Gln Asp Gly Glu Trp Ile Gly Glu Val
225                 230                 235                 240

Lys Asn Ile Ser Cys Asp Met Met Asn Ala Gln
                245                 250

<210> SEQ ID NO 48
<211> LENGTH: 65
<212> TYPE: PRT
<213> ORGANISM: Artificial Sequence
<220> FEATURE:
<223> OTHER INFORMATION: A. suum-CCP12

-continued

<400> SEQUENCE: 48

Gln Cys Phe Gly Leu Ala Pro Pro Phe Asn Gly Gln Ile Ser Tyr Ser
1               5                   10                  15

Gln Gln Ser Ser Ala Ser Thr Tyr Pro Ser Gly Thr Ile Ala Thr Leu
            20                  25                  30

Ile Cys Asn Leu Gly Phe Thr Val Ser Gly Gly Ser Thr Ala Ser Thr
        35                  40                  45

Cys Ile Asn Gly Gln Trp Asn Pro Ser Thr Leu Gly Thr Cys Gln Thr
    50                  55                  60

Gly
65

<210> SEQ ID NO 49
<211> LENGTH: 64
<212> TYPE: PRT
<213> ORGANISM: Artificial Sequence
<220> FEATURE:
<223> OTHER INFORMATION: FH-CCP1

<400> SEQUENCE: 49

Asp Cys Asn Glu Leu Pro Pro Arg Arg Asn Thr Glu Ile Leu Thr Gly
1               5                   10                  15

Ser Trp Ser Asp Gln Thr Tyr Pro Glu Gly Thr Gln Ala Ile Tyr Lys
            20                  25                  30

Cys Arg Pro Gly Tyr Arg Ser Leu Gly Asn Val Ile Met Val Cys Arg
        35                  40                  45

Lys Gly Glu Trp Val Ala Leu Asn Pro Leu Arg Lys Cys Gln Lys Arg
    50                  55                  60

<210> SEQ ID NO 50
<211> LENGTH: 244
<212> TYPE: PRT
<213> ORGANISM: Artificial Sequence
<220> FEATURE:
<223> OTHER INFORMATION: TGM domains 1-3

<400> SEQUENCE: 50

Gly Cys Met Pro Phe Ser Asp Glu Ala Ala Thr Tyr Lys Tyr Val Ala
1               5                   10                  15

Lys Gly Pro Lys Asn Ile Glu Ile Pro Ala Gln Ile Asp Asn Ser Gly
            20                  25                  30

Met Tyr Pro Asp Tyr Thr His Val Lys Arg Phe Cys Lys Gly Leu His
        35                  40                  45

Gly Glu Asp Thr Thr Gly Trp Phe Val Gly Ile Cys Leu Ala Ser Gln
    50                  55                  60

Trp Tyr Tyr Tyr Glu Gly Val Gln Glu Cys Asp Asp Arg Arg Cys Ser
65                  70                  75                  80

Pro Leu Pro Thr Asn Asp Thr Val Ser Phe Glu Tyr Leu Lys Ala Thr
                85                  90                  95

Val Asn Pro Gly Ile Ile Phe Asn Ile Thr Val His Pro Asp Ala Ser
                100                 105                 110

Gly Lys Tyr Pro Glu Leu Thr Tyr Ile Lys Arg Ile Cys Lys Asn Phe
            115                 120                 125

Pro Thr Asp Ser Asn Val Gln Gly His Ile Ile Gly Met Cys Tyr Asn
        130                 135                 140

Ala Glu Trp Gln Phe Ser Ser Thr Pro Thr Cys Pro Ala Ser Gly Cys
145                 150                 155                 160

```
Pro Pro Leu Pro Asp Asp Gly Ile Val Phe Tyr Glu Tyr Tyr Gly Tyr
                165                 170                 175

Ala Gly Asp Arg His Thr Val Gly Pro Val Val Thr Lys Asp Ser Ser
            180                 185                 190

Gly Asn Tyr Pro Ser Pro Thr His Ala Arg Arg Cys Arg Ala Leu
        195                 200                 205

Ser Gln Glu Ala Asp Pro Gly Glu Phe Val Ala Ile Cys Tyr Lys Ser
    210                 215                 220

Gly Thr Thr Gly Glu Ser His Trp Glu Tyr Tyr Lys Asn Ile Gly Lys
225                 230                 235                 240

Cys Pro Asp Pro

<210> SEQ ID NO 51
<211> LENGTH: 244
<212> TYPE: PRT
<213> ORGANISM: Artificial Sequence
<220> FEATURE:
<223> OTHER INFORMATION: TGM-a domains 1-3

<400> SEQUENCE: 51

Gly Cys Met Pro Phe Ser Asp Glu Ala Ala Thr Tyr Lys Tyr Val Ala
1               5                   10                  15

Lys Gly Pro Lys Asn Ile Glu Ile Pro Ala Gln Ile Asp Asn Ser Gly
            20                  25                  30

Met Tyr Pro Asp Tyr Thr His Val Lys Arg Phe Cys Lys Gly Leu His
        35                  40                  45

Gly Glu Asp Thr Thr Gly Trp Phe Val Gly Ile Cys Leu Ala Ser Gln
    50                  55                  60

Trp Tyr Tyr Tyr Glu Gly Val Gln Glu Cys Asp Asp Arg Arg Cys Ser
65                  70                  75                  80

Pro Leu Pro Thr Asn Asp Thr Val Ser Phe Glu Tyr Leu Lys Ala Thr
                85                  90                  95

Val Asn Pro Gly Ile Ile Phe Asn Ile Thr Val His Pro Asp Ala Ser
            100                 105                 110

Gly Lys Tyr Pro Glu Leu Thr Tyr Ile Lys Arg Ile Cys Lys Asn Phe
        115                 120                 125

Pro Thr Asp Ser Asn Val Gln Gly His Ile Ile Gly Met Cys Tyr Asn
    130                 135                 140

Ala Glu Trp Gln Phe Ser Ser Thr Pro Thr Cys Pro Ala Ser Gly Cys
145                 150                 155                 160

Pro Pro Leu Pro Asp Asp Gly Ile Val Phe Tyr Glu Tyr Tyr Gly Tyr
                165                 170                 175

Ala Gly Asp Arg His Thr Val Gly Pro Val Val Thr Lys Asp Ser Ser
            180                 185                 190

Gly Asn Tyr Pro Ser Pro Thr His Ala Arg Arg Cys Arg Ala Leu
        195                 200                 205

Ser Gln Lys Ala Asp Thr Gly Glu Phe Val Ala Ile Cys Tyr Lys Ser
    210                 215                 220

Cys Thr Thr Gly Glu Ser His Trp Gln Tyr Tyr Lys Tyr Ile Lys Asn
225                 230                 235                 240

Cys Pro Asp Pro

<210> SEQ ID NO 52
<211> LENGTH: 244
<212> TYPE: PRT
```

<213> ORGANISM: Artificial Sequence
<220> FEATURE:
<223> OTHER INFORMATION: TGM-d domains 1-3

<400> SEQUENCE: 52

Gly Cys Met Pro Phe Ser Asp Glu Ala Ala Thr Tyr Lys Tyr Val Ala
1               5                   10                  15

Lys Gly Pro Lys Asn Ile Glu Ile Pro Ala Gln Ile Asp Asn Ser Gly
            20                  25                  30

Met Tyr Pro Asp Tyr Thr His Val Lys Arg Phe Cys Lys Gly Leu His
        35                  40                  45

Gly Glu Asp Thr Thr Gly Trp Phe Val Gly Ile Cys Leu Ala Ser Gln
    50                  55                  60

Trp Tyr Tyr Glu Gly Val Gln Glu Cys Asp Asp Arg Arg Cys Ser
65                  70                  75                  80

Pro Leu Pro Thr Asn Asp Thr Val Ser Phe Glu Tyr Leu Lys Ala Thr
                85                  90                  95

Val Asn Pro Gly Ile Ile Phe Asn Ile Thr Val His Pro Asp Ala Ser
            100                 105                 110

Gly Lys Tyr Pro Glu Leu Thr Tyr Ile Lys Arg Ile Cys Lys Asn Phe
        115                 120                 125

Pro Thr Asp Ser Asn Val Gln Gly His Ile Ile Gly Met Cys Tyr Asn
    130                 135                 140

Ala Glu Trp Gln Phe Ser Ser Thr Pro Thr Cys Pro Ala Ser Gly Cys
145                 150                 155                 160

Pro Pro Leu Pro Asp Asp Gly Ile Val Phe Tyr Glu Tyr Tyr Gly Tyr
                165                 170                 175

Ala Gly Asp Arg His Thr Val Gly Pro Val Val Thr Lys Asp Ser Ser
            180                 185                 190

Gly Asn Tyr Pro Ser Pro Thr His Ala Arg Arg Cys Arg Ala Leu
        195                 200                 205

Ser Gln Glu Ala Asp Pro Gly Glu Phe Val Ala Ile Cys Tyr Lys Ser
    210                 215                 220

Gly Thr Thr Gly Glu Ser His Trp Glu Tyr Tyr Lys Asn Ile Gly Lys
225                 230                 235                 240

Cys Pro Asp Pro

<210> SEQ ID NO 53
<211> LENGTH: 244
<212> TYPE: PRT
<213> ORGANISM: Artificial Sequence
<220> FEATURE:
<223> OTHER INFORMATION: TGM-e Domains 1-3

<400> SEQUENCE: 53

Gly Cys Met Pro Phe Ser Asp Glu Thr Ala Ser Tyr Lys Tyr Leu Thr
1               5                   10                  15

Glu Arg Ser Arg Asn Asp Glu Pro Ala Gln Asn Asp Ser Ser Gly
            20                  25                  30

Ala Tyr Pro Asp His Thr His Val Lys Arg Phe Cys Lys Gly Leu His
        35                  40                  45

Gly Glu Glu Lys Thr Gly Arg Tyr Val Gly Ile Cys Leu Gly Ser Glu
    50                  55                  60

Trp Val Tyr Tyr Gln Gly Val Gln Glu Cys Gln Asp Arg Arg Cys Ser
65                  70                  75                  80

Pro Leu Pro Thr Asn Asp Thr Val Thr Tyr Glu Tyr Leu Lys Ala Thr

```
                    85                  90                  95
Val Asn Ala Gly Ile Asn Phe Asn Ile Thr Val His Pro Asp Ala Ser
                100                 105                 110

Gly Lys Tyr Pro Glu Leu Thr Tyr Ile Lys Arg Ile Cys Lys Asn Phe
            115                 120                 125

Pro Ala Asp Ser Lys Val Gln Gly His Ile Ile Gly Met Cys Tyr Asn
        130                 135                 140

Ala Glu Trp Arg Phe Ser Ser Thr Pro Thr Cys Pro Pro Ser Gly Cys
145                 150                 155                 160

Pro Pro Leu Pro Asp Asp Gly Ile Val Phe Glu Tyr Tyr Gly Tyr
                165                 170                 175

Ala Gly Asn Arg His Thr Val Gly Arg Ala Val Ser Lys Asp Ser Ser
                180                 185                 190

Gly Asn Tyr Pro Pro Gln Thr His Ala Arg Arg Cys Arg Ala Leu
            195                 200                 205

Ser Gln Lys Ala Asp Pro Gly Glu Phe Val Gly Ile Cys Tyr Lys Ser
        210                 215                 220

Gly Thr Thr Gly Glu Ser His Trp Asp Tyr Tyr Ser His Ile Arg Lys
225                 230                 235                 240

Cys Pro Asp Pro

<210> SEQ ID NO 54
<211> LENGTH: 244
<212> TYPE: PRT
<213> ORGANISM: Artificial Sequence
<220> FEATURE:
<223> OTHER INFORMATION: TGM-f Domains 1-3

<400> SEQUENCE: 54

Ser Cys Met Pro Leu Ser Glu Glu Thr Asp Thr Tyr Gln Tyr Phe Ala
1               5                   10                  15

Gln Thr Ser Asn Lys Glu Glu Thr Pro Ala Arg Lys Asp Ser Ser Gly
            20                  25                  30

Met Tyr Pro Glu Tyr Thr His Val Lys Arg Phe Cys Lys Gly Leu His
        35                  40                  45

Gly Glu Asp Lys Thr Gly Glu Phe Ile Gly Leu Cys His Arg Ser Glu
    50                  55                  60

Trp Val Tyr Tyr Met Gly Val Gln Glu Cys Arg Asp Arg Arg Cys Ser
65                  70                  75                  80

Pro Leu Ser Glu Ser Asp Thr Val Ser Tyr Glu Tyr Arg Lys Ala Thr
                85                  90                  95

Leu Asn Ser Ser Arg Ile Ser Tyr Asp Thr Ser Ala Asn Pro Asp Asp
                100                 105                 110

Ser Gly Lys Tyr Pro Glu Leu Thr Tyr Ile Arg Arg Ile Cys Lys Asn
            115                 120                 125

Phe Pro Ala Asn Ser Lys Val Arg Gly Val Ile Val Gly Met Cys Tyr
        130                 135                 140

Asn Ala Glu Trp Arg Phe Ser Ser Ala Pro Val Cys Pro Pro Tyr Gly
145                 150                 155                 160

Cys Pro Pro Ile Gln Asp Asn Asp Lys Phe Arg His Glu Tyr Tyr Glu
                165                 170                 175

Tyr Ala Gly Ser Arg Asp Val Val Gly Gln Ala Val Thr Lys Asp Ser
                180                 185                 190

Ser Gly Asn Tyr Pro Pro Gln Thr His Ala Arg Arg His Cys Gln Ala
            195                 200                 205
```

-continued

```
Arg Ser Val Lys Val Asp Gln Gly Glu Leu Val Ala Ile Cys His Glu
    210                 215                 220

Arg Ser Asp Thr Gly Glu Ser Arg Trp Val Tyr Tyr His Asn Ile Lys
225                 230                 235                 240

Gln Cys Pro Val
```

MATERIALS AND METHODS FOR INDUCING REGULATORY T CELLS

CROSS-REFERENCE TO RELATED APPLICATIONS

The present application is a § 371 of International Patent Application No. PCT/EP2018/071201, filed Aug. 3, 2018, which claims priority from GB Application No. 1712556.8, filed Aug. 4, 2017. The entire disclosure of each of the aforesaid applications is incorporated by reference in the present application.

Incorporation by Reference of Material Submitted in Electronic Form

Incorporated herein by reference in its entirety is the sequence listing submitted via EFS-Web as a text file named SEQLIST.txt, created Jul. 1, 2022, and having a size of 90,112 bytes.

FIELD OF THE INVENTION

The present invention relates to materials and methods for inducing regulatory T cells. Particularly, but not exclusively, the invention concerns a structurally distinct immunosuppressive mimic of TGF-β that is a potent inducer of murine and human regulatory T cells and provides a therapeutic agent for the treatment of inflammatory disorders.

BACKGROUND OF THE INVENTION

Parasitic helminths are able to establish a state of immune hypo-responsiveness or tolerance in their host which attenuates both host immunity and reactivity to third-party specificities, such as allergens and autoantigens[1-3]. While a wide range of molecular and cellular mechanisms of parasite immune suppression have been described, a prominent feature of many helminth infections is expansion of the regulatory T cell (Treg) population, an immune subset that controls immunity in infection, allergy, and autoimmunity[4-6]. Activation of Tregs is particularly marked in mice infected with the gastrointestinal nematode Heligmosomoides polygyrus, with Tregs controlling both susceptibility to infection and propensity to allergic reactivity[7-10]. In particular, antibody-mediated depletion of Tregs promotes resistance in genetically-susceptible mice, while Treg expansion (with IL-2:anti-IL-2 complex) renders genetically-resistant mice susceptible[10].

In the mature peripheral immune system, induction of Tregs to exogenous antigen specificities, for example from the microbiota or innocuous environmental substances, is promoted by the cytokine TGF-β[11-14]. Mice deficient in either the TGF-β1 ligand or TGF-β receptors suffer a dearth of inducible Tregs and succumb to disseminated inflammatory disease in the weeks following birth[15]. TGF-β is a member of a highly diversified signalling family, which includes many essential developmental and morphogenetic proteins, and indeed mice lacking the TGF-β2 and TGF-β3 isoforms suffer lethal congenital deformities[16, 17]. TGF-β family members carry out developmental roles in invertebrates including helminths such as *Caenorhabditis elegans*[18] and *H. polygyrus*[19], indicating that the immunological function of mammalian TGF-βs emerged at a relatively recent point in evolution[20].

It has been previously reported that *H. polygyrus* elaborates a soluble secreted product which acts like TGF-β to induce expression of the Treg-specific transcription factor, Foxp3, in naïve peripheral T cells[9]; however, the identity of the active protein among the more than 370 different products released by the parasite[21, 22] remained elusive.

*H. polygyrus* infection prevents the development of asthma in mice, and the protective effect can be conferred on uninfected mice by the transfer of Tregs from infected mice[23]. As the parasite population remains alive and stable in the host, it was hypothesised that Treg activation was due to the release of soluble products from the parasite. These soluble products have been collected by culturing adult parasites in serum-free medium and collecting, purifying and concentrating the molecules they release[24]. These products (termed the excretory/secretory products of *H. polygyrus*, HES) can replicate the suppressive effects of *H. polygyrus* infection in mouse models of asthma. They can signal through the mammalian TGF-β receptor, inducing functionally suppressive CD4+Foxp3+ regulatory T cells (Tregs) in vitro[9]. Tregs are crucial for tolerance to self, commensal and dietary antigens, and in their absence the immune system is prone to hyperactivity, with much increased incidence of autoimmunity, colitis and allergy.

SUMMARY OF THE INVENTION

The inventors have identified a novel parasite TGF-β mimic which fully replicates the biological and functional properties of TGF-β, including binding to mammalian TGF-β receptors and inducing Foxp3+ Treg in both murine and human CD4+ T cells. This TGF-β mimic (hereinafter TGM) shares no homology to mammalian TGF-β or other members of the TGF-β family, but is distantly related to the complement control protein (CCP) superfamily. Thus, through convergent evolution, the parasite has acquired a cytokine-like function able to exploit the endogenous pathway of immunoregulation in the host. The inventors have recognised that this protein will provide improved therapeutics for the treatment of inflammatory diseases, particularly of the immune system.

The inventors have shown that the TGM polypeptide is a secreted, functionally active 404 amino acid protein (See FIG. 1 A), which although highly cysteine-rich, and bearing no sequence similarity to mammalian TGF-β, acts as a fully functional mimic of the mammalian cytokine. Further, they have shown that it is able, in a parallel fashion, to bind and activate the TGF-β receptor (a TGF-β receptor agonist) and its signalling pathway; as a result the mimic potently induces expression of Foxp3 in murine and human T cells. They have deduced that the TGM sequence comprises 5 homologous but non-identical domains (See FIG. 1 B) with similar positioning of cysteine residues and likely disulphide bonds, and each encoded by 2 exons in the parasite genome (See FIG. 1 C).

Accordingly, at its most general, the invention provides polypeptides derived from this novel and distinct TGF-β mimic (TGM) protein which are TGF-β receptor agonists and therefore have utility as new therapeutics for the treatment of inflammatory disorders, such as asthma, colitis and allograft rejection. The invention further provides pharmaceutical compositions comprising said polypeptides and methods for their use in treating such inflammatory disorders.

In a first aspect, there is provided a polypeptide comprising TGM domain 1 and TGM domain 3, wherein said polypeptide has TGF-β receptor agonist activity.

In one embodiment, the polypeptide comprises an additional amino acid sequence linking TGM domain 1 and TGM domain 2. This linker amino acid sequence may be between 10 and 150 amino acids in length, between 30 and 100 amino acids in length, between 50 and 80 amino acids in length or between 70 and 90 amino acids in length. In one embodiment, the linker sequence is TGM domain 2, or a variant thereof.

In some embodiments, the polypeptide comprises TGM domain 1, TGM domain 2 and TGM domain 3.

In some embodiments, the polypeptide comprises TGM domain 1, TGM domain 2, TGM domain 3 and TGM domain 4.

In some embodiments, the polypeptide comprises TGM domain 1, TGM domain 2, TGM domain 3, TGM domain 4 and TGM domain 5.

The TGM protein comprises 422 amino acids of which the first 18 are a signal peptide and encoded by a single exon. The remaining 404 amino acids form the mature protein. The mature protein comprises 5 homologous but non-identical CCP-like domains of approximately 80 amino acids in length (See FIGS. 1 B and C).

```
Signal Peptide
MLLTVVIGLLEVAATDDS

TGM Domain 1 (19 to 95)
GCMPFSDEAATYKYVAKGPKNIEIPAQIDNSGMYPDYTHVKRFCKGLHGE

DTTGWFVGICLASQWYYYEGVQECDDR
```

By "TGM Domain 1" is meant a polypeptide sequence comprising at least amino acids 19 to 95 of TGM protein shown above (see also FIG. 1), a fragment thereof, or a variant of either having at least 70%, at least 80%, at least 90%, at least 95% or at least 99% sequence identity with the corresponding TGM sequence. The TGM Domain 1 may be at least 50, at least 60, at least 70, or at least 75 amino acids in length.

Cysteine residues are identified by underline. In some embodiments, these residues are maintained, i.e. not mutated, in the TGM Domain 1 polypeptide sequence of the invention.

```
TGM Domain 2 (96 to 176)
RCSPLPTNDTVSFEYLKATVNPGIIFNITVHPDASGKYPELTYIKRICKN

FPTDSNVQGHIIGMCYNAEWQFSSTPTCPAS
```

By "TGM Domain 2" is meant a polypeptide sequence comprising at least amino acids 96 to 176 of TGM protein shown above (see also FIG. 1), a fragment thereof, or a variant of either having at least 20%, at least 40%, at least 50%, at least 60%, at least 70%, at least 80% at least 90%, at least 95% or at least 99% sequence identity with the corresponding TGM sequence. The TGM Domain 2 may be at least 50, at least 60, at least 70, or at least 75 amino acids in length.

Cysteine residues are identified by underline. In some embodiments, these residues are maintained, i.e. not mutated, in the TGM Domain 2 polypeptide sequence of the invention.

```
TGM Domain 3 (177-262)
GCPPLPDDGIVFYEYYGYAGDRHTVGPVVTKDSSGNYPSPTHARRRCRAL

SQEADPGEFVAICYKSGTTGESHWEYYKNIGKCPDP
```

By "TGM Domain 3" is meant a polypeptide sequence comprising at least amino acids 177 to 262 of TGM protein shown above (see also FIG. 1), a fragment thereof, or a variant of either having at least 70%, at least 80% at least 90%, at least 95% or at least 99% sequence identity with the corresponding TGM sequence. The TGM Domain 3 may be at least 50, at least 60, at least 70, at least 75, or at least 80 amino acids in length.

Cysteine residues are identified by underline. In some embodiments, these residues are maintained, i.e. not mutated, in the TGM Domain 3 polypeptide sequence of the invention.

```
TGM Domain 4 (263-343)
RCKPLEANESVHYEYFTMTNETDKKKGPPAKVGKSGKYPEHTCVKKVCSK

WPYTCSTGGPIFGECIGATWNFTALMECINA
```

By "TGM Domain 4" is meant a polypeptide sequence comprising at least amino acids 263 to 343 of TGM protein shown above (see also FIG. 1), a fragment thereof, or a variant of either having at least 20%, at least 40%, at least 50%, at least 60%, at least 70%, at least 80% at least 90%, at least 95% or at least 99% sequence identity with the corresponding TGM sequence. The TGM Domain 4 may be at least 50, at least 60, at least 70, or at least 75 amino acids in length.

Cysteine residues are identified by underline. In some embodiments, these residues are maintained, i.e. not mutated, in the TGM Domain 4 polypeptide sequence of the invention.

```
TGM Domain 5 (344-422)
RGCSSDDLFDKLGFEKVIVRKGEGSDSYKDDFARFYATGSKVIAECGGKI

VRLECSNGEWHEPGTKTVHRCTKDGIRTL*
```

By "TGM Domain 5" is meant a polypeptide sequence comprising at least amino acids 344 to 422 of TGM protein shown above (see also FIG. 1), a fragment thereof, or a variant of either having at least 20%, at least 40%, at least 50%, at least 60%, at least 70%, at least 80% at least 90%, at least 95% or at least 99% sequence identity with the corresponding TGM sequence. The TGM Domain 5 may be at least 50, at least 60, at least 70, or at least 75 amino acids in length.

Cysteine residues are identified by underline. In some embodiments, these residues are maintained, i.e. not mutated, in the TGM Domain 5 polypeptide sequence of the invention.

Variants of the TGM domains or fragments thereof, may have an addition, deletion or a substitution of one or more amino acids compared to the corresponding TGM sequence as depicted in FIG. 1 A and Table 1.

Table 1 provides a number of variants of TGM polypeptide, named: TGM-a to TGM-i. Of these variants, TGM-a and TGM-d (along with TGM) were shown to have TGF-β receptor agonist activity. TGM-a has identical amino acid sequence to TGM for positions 1 to 228. The remaining sequence (position 229-422) comprises 49 changes in sequence with 8 additional residues.

TGM-d has identical amino acid sequence to TGM for positions 1 to 318. The remaining sequence (position 319-422) comprises 63% sequence identity with TGM with 8 additional residues. Thus, each of the active proteins share identical N-terminal domains at least up to amino acid position 228.

Accordingly, it is clear that the N-terminal domains are important for TGF-β receptor agonist activity. In one embodiment, the polypeptide of the invention comprises an amino acid sequence 19 to 228 of the TGM protein (see FIG. 1 A) and has TGF-β receptor agonist activity. The polypeptide may further comprise amino acid sequence 229 to 422 of the TGM protein or a variant thereof having at least 50% sequence identity, at least 60% sequence identity, at least 70% sequence identity at least 80% sequence identity, at least 90% sequence identity or at least 95% sequence identity with positions 229 to 422 of TGM protein (see FIG. 1 A).

The polypeptide of the invention has TGF-β receptor agonist activity. In one embodiment TGF-β receptor agonist activity may be shown by the ability of the polypeptide to induce reporter cell function in a TGF-β bioassay, e.g. MFB-F11 as developed by Tesseur et al[25]. In some embodiments, the polypeptide of the invention will have an activity at least equal to hTGF-β1 in said TGF-β bio-assay. Further, in some embodiments, the polypeptide of the invention will have an activity of greater than 1.5 ($OD_{405}$ at 100 ng/ml); greater than 1.7 ($OD_{405}$ at 100 ng/ml); or greater than 2.0 ($OD_{405}$ at 100 ng/ml) in said MFB-F11 hTGF-β bioassay; in each case as compared to (or equal or greater than) the maximum level stimulated by recombinant TGF-β.

In a second aspect of the invention, there is provided a nucleic acid sequence which encodes the polypeptide according to the first aspect of the invention.

The invention also provides expression vectors (e.g. bacterial, eukaryotic or viral vectors and plasmids, cosmids and phages) comprising said nucleic acid sequence of the second aspect. These vectors may be used to express the nucleic acid sequence in vitro or in vivo, in a range of prokaryotic and eukaryotic expression systems as well as by in vitro translation in a cell-free system.

Also provided is a host cell comprising the nucleic acid sequence or the expression vector according to the second aspect. The host cell may comprise the nucleic acid sequence integrated into its genome such that it can express the polypeptide of the invention under the control of exogenous or endogenous regulatory elements such as promotors. Alternatively, the host cell may comprise an expression vector of the invention capable of expressing the polypeptide of the invention or a virion comprising an expression construct capable of expressing the polypeptide of the invention.

The invention includes a method of culturing the host cell under condition suitable for it to express the polypeptide and harvesting said polypeptide. The invention further includes a polypeptide obtained or obtainable from said host cell Table 1 provides the nucleic acid sequence for TGM and variants thereof TGM-a to TGM-i. In one embodiment, the nucleic acid sequence of the second aspect has a sequence identity of at least 70% with the TGM nucleic acid sequence in Table 1. In some embodiments, this sequence identity is at least 80%, at least 90%, or at least 95% with the TGM nucleic acid sequence in Table 1. In one embodiment, the nucleic acid sequence of the invention comprises the sequence for TGM, TGM-a or TGM-d as shown in Table 1.

In some embodiments, the nucleic acid sequence of the second aspect encodes a domain of the TGM polypeptide, or a fragment or variant thereof. The nucleic acid sequence may encode a polypeptide sequence comprising TGM domain 1 and TGM domain 3. In one embodiment, the nucleic acid sequence encodes a polypeptide comprising at least TGM domain 1, TGM domain 2 and TGM domain 3, variants thereof. In a further embodiment, the nucleic acid sequence of this second aspect encodes a polypeptide comprising or consisting of amino acid sequence 19 to 262 of FIG. 1 A).

In a third aspect, there is provided a pharmaceutical composition comprising a TGM polypeptide of the invention, a nucleic acid sequence encoding a TGM polypeptide of the invention, a host cell, an expression vector and/or virions of the invention.

The inventors have shown that the TGM polypeptides of the invention can be used in the treatment of a range of inflammatory disorders in a subject. Accordingly, in a fourth aspect of the invention there is provided a TGM polypeptide, nucleic acid sequence encoding a TGM polypeptide, an expression vector, and/or virions of the invention for use in a method of medical treatment. In one embodiment the medical treatment is for an inflammatory disease or disorder.

The invention also provide the use of said TGM polypeptide, nucleic acid sequence encoding a TGM polypeptide, an expression vector, and/or virions of the invention in the preparation of a medicament for treating an inflammatory disease or disorder.

In accordance with all aspects of the invention, said inflammatory disease or disorder is preferably selected from the group consisting of allergic or hypersensitivity diseases such as hay fever, food allergies, atopic dermatitis, asthma, anaphylaxis, allergic rhinitis, urticaria, eczema, Celiac disease; and/or immune-mediated inflammatory diseases such as Ankylosing spondylitis, Vasculitis, Arthritis, Hepatitis, Chronic inflammatory demyelinating polyneuropathy, Rheumatoid arthritis, Colitis (Crohn's disease, and/or ulcerative colitis), Erythema, Rheumatism, inflammatory bowel disease, Pelvic inflammatory disease, Thyroiditis, myopathy, myositis, Behcet's disease, psoriasis, psoriatic arthritis, multiple sclerosis, type 1 diabetes, and/or allograft reactivity leading to rejection of skin or organ transplants, or graft-versus-host disease following bone marrow transplantation.

In a sixth aspect, the invention provides a method of treating an inflammatory disease or disorder in a subject, said method comprising administering an immunosuppressive agent to said subject, wherein said immunosuppressive agent is selected from the group consisting of a TGM polypeptide of the invention, a nucleic acid sequence encoding a TGM polypeptide of the invention, an expression vector comprising a nucleic acid sequence of the invention, a host cell and a virion of the invention.

The invention provides therapeutic immunosuppressive agents that can be used in the treatment of inflammatory diseases or disorders. The immunosuppressive agents include the polypeptides nucleic acid sequences, expression vectors, and host cells of the invention. The polypeptides can be administered directly to the subject, whereas the nucleic acid sequences, expression vectors and/or host cells can be used to express and, optionally deliver the TGM polypeptides in vivo. This may be preferable to not only ensure localised expression and therefore concentration of the TGM polypeptide, but to extend the circulatory half-life of the polypeptide by preventing degradation. Accordingly, the invention provides method of treatment using these immunosuppressive agents and the use of the immunosuppressive agents in those treatments.

In one embodiment, the invention further provides the use of the immunosuppressive agents of the invention in the preparation of a medicament to treat an inflammatory disease or disorder.

A further therapeutic use of the polypeptides of the invention is the ex vivo conversion of peripheral T cells obtained from an individual, through in vitro co-culture with the polypeptide of the invention, into Treg cells which may be returned to the same individual in order to dampen inflammatory disease. This approach has the merit of not exposing the individual to the polypeptides of the invention directly in case this elicits an antibody response in that individual that neutralises its efficacy in vivo.

Accordingly, in a seventh aspect of the invention there is provided an in vitro method of converting peripheral T cells into regulatory T cells (Treg cells) for use in treating inflammatory diseases, said method comprising contacting a sample of peripheral T cells with a polypeptide of the invention, culturing said cells with said polypeptide in culture medium, and collecting converted Treg cells from said culture medium. The peripheral T cells may be collected from, or previously obtained from, an individual. The method may further comprise administering said converted Treg cells to said patient in order to treat an inflammatory disease.

Thus the methods of this aspect of the invention can equally be referred to as methods of inhibiting or suppressing an immune response against an antigen.

In practice, these methods of the invention may be used therapeutically or prophylactically to inhibit or suppress an undesirable immune response against a particular antigen, even in a subject with pre-existing immunity or an on-going immune response to that antigen. This may be particularly useful (for example) in the treatment of autoimmune disease.

In accordance with this aspect of the invention, there is also provided Treg cells and pharmaceutical compositions comprising said Treg cells, wherein said Treg cells have been obtained through the conversion of peripheral T cells following culture with a polypeptide of the invention.

TGM Polypeptides

In the context of the invention, the term "polypeptide" refers to a polymer formed from amino acids covalently linked by peptide bonds, without regard to the length of the polymer. Accordingly, peptides, oligopeptides, and proteins are included within the term "polypeptide".

The polypeptides of the invention may also include post-expression modifications, for example covalent attachment of glycosyl groups, acetyl groups, phosphate groups, non-peptidyl polymers, and/or lipid groups. For example, the polypeptides may be modified by pegylation.

The polypeptides of the invention may be modified to improve biological function such as activity, stability etc. Accordingly, the invention includes salts, amides, esters, (e.g. C-terminal esters), and N-acyl derivatives of the polypeptides of the invention.

Polypeptides of the invention may form complexes with one or more other polypeptides to create a dimer or other multimer, a fusion protein, a protein variant, or derivative thereof.

The polypeptides of the invention comprise a TGM domain 1 and a TGM domain 3 and have TGF-β receptor agonist activity. The inventors have shown that these two domains are required for TGF-β receptor agonist activity.

In a preferred embodiment, the polypeptides of the invention have TGF-β receptor agonist activity substantially the same or greater than that of Hp-TGM protein. Alternatively, the polypeptides of the invention have TGF-β receptor agonist activity substantially the same or greater than that of hTGF-β1. The TGF-β receptor agonist activity may be determined in a TGF-β bio-assay, for example, MFB-F11 as developed by Tesseur et al[25] and as described herein.

In some embodiments, the amino acid sequence of TGM domain 1 has at least 70%, at least 80%, at least 90%, at least 95% or at least 98% sequence identity with the corresponding TGM sequence provided in FIG. 1 A and/or Table 1.

In some embodiments, the amino acid sequence of TGM domain 3 has at least 70% at least 80%, at least 90%, at least 95% or at least 98% sequence identity with the corresponding TGM sequence provided in FIG. 1 A and/or Table 1 (TGM, TGM-a or TGM-d).

In one embodiment the polypeptides of the invention further comprise TGM domain 2 and/or TGM domain 4, and/or TGM domain 5, having at least 70%, 75%, 80%, 85%, 88%, 90%, 92%, 94%, 95%, 96%, 97%, 98% or 99% sequence identity with the corresponding TGM sequence provide in FIG. 1 A and/or Table 1.

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Reference to "corresponding TGM sequence" should be taken to mean the portion of TGM sequence which aligns with a query sequence when that query sequence is optimally aligned with the full length TGM sequence or with the relevant TGM domain. Thus, for example, a 40 amino acid sequence which is identical to a contiguous 40 amino acid stretch of a TGM sequence would be considered to have 100% identity to that stretch of corresponding TGM sequence.

Variants of the TGM domains of the invention as described above can be either natural or synthetic variants, and may contain variations in the amino acid sequence due to deletions, substitutions, insertions, inversions or additions of one or more amino acids in said sequence. Variants may comprise one or more non-natural amino acids (i.e. an amino acid not encoded by the standard genetic code). As described above, variants may also include covalent modifications to amino acids within the sequence, such as addition of a non-peptidyl polymer such as polyethylene glycol (PEG), addition of a carbohydrate group, or modification of a naturally-occurring carbohydrate.

In one embodiment, variants of the TGM domains of the invention may contain variations in the amino acid sequence due to deletions, substitutions, insertions, inversions or additions of one or more amino acids in said sequence, other than structurally important residues, such as cysteine residues. Accordingly, it may be preferable that variants of the TGM domains of the invention comprise at least the cysteine residues as identified in FIG. 1.

Further, the variant TGM domains of the invention may maintain one or more glycosylation sites of the TGM sequence of FIG. 1.

However, in some embodiments, the glycosylation sites of the TGM sequence of FIG. 1 may be mutated so that the variant TGM polypeptide is a non-glycosylated form. This may improve properties of the polypeptide such as solubility.

The domains or polypeptides of the invention may contain one or more conservative substitutions relative to the corresponding TGM sequence of FIG. 1. A conservative substitution may be defined as a substitution within an amino acid class and/or a substitution that scores positive in the BLOSUM62 matrix.

According to one classification, the amino acid classes are acidic, basic, uncharged polar and nonpolar, wherein acidic amino acids are Asp and Glu; basic amino acids are Arg, Lys and His; uncharged polar amino acids are Asn, Gln, Ser, Thr and Tyr; and non-polar amino acids are Ala, Gly, Val, Leu, lie, Pro, Phe, Met, Trp and Cys.

According to another classification, the amino acid classes are small hydrophilic, acid/acid amide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, lie, Leu and Val; and aromatic amino acids are Phe, Tyr and Trp Substitutions which score positive in the BLOSUM62 matrix are as follows:

| Original Residue | C | S | T | P | A | G | N | D | E | Q | H | R | K | M | I | L | V | F | Y | W |
|---|---|---|---|---|---|---|---|---|---|---|---|---|---|---|---|---|---|---|---|---|
| Substitution | — | T | S — | S — | | | S | N | D | E | N | Q | E | I | M | M | M | Y | H | F |
| | | A | | | | | D | E | Q | R | Y | K | Q | L | L | I | I | W | F | Y |
| | | N | | | | | | H | | K | K | | R | V | V | V | L | | W | |

Typically, a conservative substitution is one which does not affect function of the polypeptide or domain, or which has only little effect on function. For example, a conservative substitution in the context of the present invention will have little or no impact on the ability of the domain or polypeptide to bind the TGF-β receptor and/or to exert TGF-β agonist activity. Receptor binding and activity may be determined using the assays described herein.

It may be desirable that each domain comprises 10 or fewer conservative substitutions compared to the corresponding native TGM sequence. Each domain may therefore include 1, 2, 3, 4, 5, 6, 7, 8, 9 or 10 conservative substitutions. In some embodiments, the polypeptide of the invention contains 10 or fewer conservative substitutions compared to the corresponding native TGM sequence, e.g. 1, 2, 3, 4, 5, 6, 7, 8, 9 or 10 conservative substitutions.

It may be desirable that each domain independently differs from the corresponding TGM sequence only by conservative substitutions, or that the polypeptide of the invention differs from the corresponding TGM sequence only by conservative substitutions.

The TGM polypeptides of the invention may also be conjugated to further peptides such complementary therapeutic peptides or peptides which prevent degradation in vivo and increase half-life of the TGM polypeptides, or to assist in the delivery of the TGM polypeptides in vivo. For example, the inhibitory Fc receptor Fc(gamma)RIIb could stabilise the therapeutic polypeptides of the invention and extend their in vivo efficacy. Further, the polypeptide of the invention may be dimerised to enhance avidity for cell surface receptors for TGF-β.

Nucleic Acids

The invention provides nucleic acids encoding a polypeptide of the invention, and expression vectors comprising a nucleic acid encoding a polypeptide of the invention. The term "expression vector" and "expression construct" are used interchangeably.

The nucleic acid sequences of the invention include RNA, DNA, or RNA/DNA hybrid sequences of one or more nucleotides in either single stranded or duplex form.

Nucleic acids encoding polypeptides of the invention may be provided as part of a suitable vector, such as an expression vector, in order to achieve expression of the polypeptide. The vectors can, depending on purpose and type of application, be in the form of plasmids, phages, cosmids, mini-chromosomes, or virus, but may also be delivered as naked DNA. Preferred vectors are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression from the nucleic acid encoding the polypeptide, optionally a nucleic acid sequence encoding a leader peptide enabling secretion (to the extracellular phase or, where applicable, into the periplasm), the nucleic acid encoding the polypeptide, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The nucleic acids and vectors of the invention may be used to transform host cells. Such transformed cells can be cultured cells or cell lines used for propagation of the nucleic acids and vectors, and/or recombinant production of the polypeptides.

Suitable host cells may be eukaryotic or prokaryotic. They include micro-organisms, which may be bacteria, such as *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the host cells may be derived from a multicellular organism, e.g. they may be fungal cells, insect cells, algal cells, plant cells, or an animal cell. A mammalian cell may be particularly appropriate, such as a human cell, e.g. HEK293 or HEK293T. For the purposes of cloning and/or optimised expression it is preferred that the host cell is capable of replicating the nucleic acid or vector of the invention.

For the human cell line HEK293 (and HEK293T), the plasmid vector pSecTag and its derivatives are particularly suitable.

The nucleic acid or expression vector of the invention may be introduced into the host cell by any appropriate method including electroporation, calcium chloride transfection and lipofectins.

When producing the precursor peptide by means of transformed cells, it is convenient, although far from essential, that the expression product is secreted into the culture medium.

As described above, an expression vector of the invention may be a viral vector, i.e. a virion comprising a nucleic acid encoding a polypeptide of the invention and capable of directing expression thereof in a target cell.

Any suitable type of viral vector may be employed. These include adenovirus, adeno-associated virus (AAV), retrovirus (especially lentivirus), alphavirus and herpesvirus vectors. Adenovirus and lentivirus may be particularly preferred for gene delivery in vivo as they have the capacity to achieve expression of the gene(s) delivered in cells which are not actively dividing.

The viral vector typically comprises viral structural proteins and a nucleic acid payload which comprises the desired expression construct in a form functional to express the gene in the target cell or tissue. Thus the gene is typically operably linked to a promoter and other appropriate transcriptional regulatory signals.

In adenoviral vectors, the nucleic acid payload is typically a double stranded DNA (dsDNA) molecule. In retroviral vectors, it is typically single stranded RNA.

The nucleic acid payload typically contains further elements required for it to be packaged into the gene delivery vehicle and appropriately processed in the target cell or tissue.

For adenoviral vectors, these may include adenoviral inverted terminal repeat (ITR) sequences and an appropriate packaging signal.

For retroviral vectors, these include characteristic terminal sequences (so-called "R-U5" and "U3-R" sequences) and a packaging signal. The terminal sequences enable the generation of direct repeat sequences ("long terminal repeats" or "LTRs") at either end of the provirus which results from reverse transcription, which then facilitate integration of the provirus into the host cell genome and direct subsequent expression.

The nucleic acid payload may also contain a selectable marker, i.e. a gene encoding a product which allows ready detection of transduced cells. Examples include genes for fluorescent proteins (e.g. GFP), enzymes which produce a visible reaction product (e.g. beta-galactosidase, luciferase) and antibiotic resistance genes.

The viral vector is typically not replication-competent. That is to say, the nucleic acid payload does not contain all of the viral genes (and other genetic elements) necessary for viral replication. The viral vector will nevertheless contain all of the structural proteins and enzyme activities required for introduction of the payload into the host cell and for appropriate processing of the payload such that the encoded miR-29, mimic or precursor can be expressed. Where these are not encoded by the nucleic acid payload, they will typically be supplied by a packaging cell line. The skilled person will be well aware of suitable cell lines which can be used to generate appropriate viral delivery vehicles.

Thus, for an adenoviral vector, the nucleic acid payload typically lacks one or more functional adenoviral genes from the E1, E2, E3 or E4 regions. These genes may be deleted or otherwise inactivated, e.g. by insertion of a transcription unit comprising the heterologous gene or a selective marker.

In some embodiments, the nucleic acid contains no functional viral genes. Thus, for an adenoviral vector, the only viral components present may be the ITRs and packaging signal.

Nucleic acids having no functional viral genes may be preferred, as they reduce the risk of a host immune response developing against the transduced target cell or tissue as a result of viral protein synthesis.

Methods of Treatment

The inventors have shown that polypeptides of the invention are able to signal through the TGF-β pathway and, like TGF-β itself, induce potently suppressive Treg and abate inflammation in vivo. Accordingly, these TGM polypeptides provide a novel therapeutic for treating or preventing inflammatory diseases and disorders. Further, the TGM polypeptides of the invention may be used to dampen or prevent immune responses where undesirable, e.g. following introduction of non-host tissue into a subject via transplantation.

The inventors have shown that the TGM polypeptides of the invention can be used to block inflammatory or allergy-inducing pathways.

Accordingly, the invention provides a method of treating or preventing an inflammatory disease in a mammalian subject, preferably a human subject comprising administering an immunosuppressive agent of the invention.

The invention further provides a method of culturing cells obtained from a subject with the polypeptides of the invention to expand Tregs. Said cells may then be returned via administration to said subject in order to treat an inflammatory disease or disorder.

The invention provides an immunosuppressive agent comprising a TGM polypeptide of the invention, a nucleic acid sequence encoding a TGM polypeptide of the invention, or an expression vector comprising said nucleic acid sequence.

The invention further provides an immunosuppressive agent for use in a method of treating inflammatory disorders or diseases in a subject.

The inflammatory diseases or disorders may be selected from the group consisting of allergic and hypersensitivity diseases such as hay fever, food allergies, atopic dermatitis, asthma, anaphylaxis, allergic rhinitis, urticarial, eczema, Celiac disease; and/or immune-mediated inflammatory diseases such as Ankylosing spondylitis, Vasculitis, Arthritis, Hepatitis, Chronic inflammatory demyelinating polyneuropathy, Rheumatoid arthritis, Colitis (Crohn's disease, and/or ulcerative colitis), Erythema, Rheumatism, inflammatory bowel disease, Pelvic inflammatory disease, Thyroiditis, myopathy, myositis, Behcet's disease, psoriasis, psoriatic arthritis, multiple sclerosis, type 1 diabetes, and/or allografts reactivity leading to rejection of skin or organ transplants, or graft-versus-host disease following bone marrow transplantation.

Pharmaceutical Compositions

The polypeptides, nucleic acids, vectors, host cells, virions, etc. described herein can be formulated in pharmaceutical compositions, e.g. for use in treating conditions such as those set out above.

The pharmaceutical compositions for use in accordance with the invention may be formulated in ways well known in the art using one or more physiologically acceptable carriers comprising excipients and auxiliaries which facilitate processing of the active compounds into preparations which can be used pharmaceutically. Examples of pharmaceutically acceptable carriers are those available in the art and include stearic acid, lactose, starch, gelatin, pectin, mannitol, sorbitol, Tween80, water, saline, glycerol and ethanol, mineral acid salts such as hydrochlorides, hydrobromides, calcium and sodium salts of phosphoric and sulfuric acids; and the salts of organic acids such as acetates, propionates, malonates, benzoates. Additionally, auxiliary substances, such as wetting or emulsifying agents, pH buffering substances, lubricants, binding agents, adhesives and/or polymers may be included. The precise nature of the carrier or other material may depend on the intended route of administration.

Administration may be by any appropriate route, e.g. oral, intravenous, cutaneous or subcutaneous, nasal, intramuscular or intraperitoneal. For treatment of an allergic or inflammatory disorder, direct injection into the affected tissue may be appropriate. For the treatment of asthma, it may be preferable for the immunosuppressive agents to be inhaled. For skin disorders, the agents may be applied topically.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Administration is preferably in a "prophylactically effective amount" or a "therapeutically effective amount" (as the case may be), this being sufficient to show benefit to the individual. In the context of the present invention, a "therapeutically effective amount" may be an amount sufficient to prevent, dampen or alleviate the symptoms of an inflammatory disorder in a subject.

Methods of determining the most effective means and dosages of administration are well known to those of skill in the art and will vary with mode of administration of the immunosuppressive agents of the invention and the subject being treated. The invention includes a dosage form of the pharmaceutical composition wherein the immunosuppressive agent is in an amounts sufficient to inhibit or suppress an undesirable inflammatory and/or immune response in a subject against a particular antigen. The dosage form may be prepared for single and multiple administrations as selected by the treating physician.

The "subject" is typically a mammal, including for example, mouse, rat, rabbit, pig, a non-human primate or a human. In preferred embodiment, the subject is a human subject.

Examples of the techniques and protocols mentioned above can be found in Remington's Pharmaceutical Sciences, 20th Edition, 2000, pub. Lippincott, Williams & Wilkins.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

FIG. 1

Figure 2:
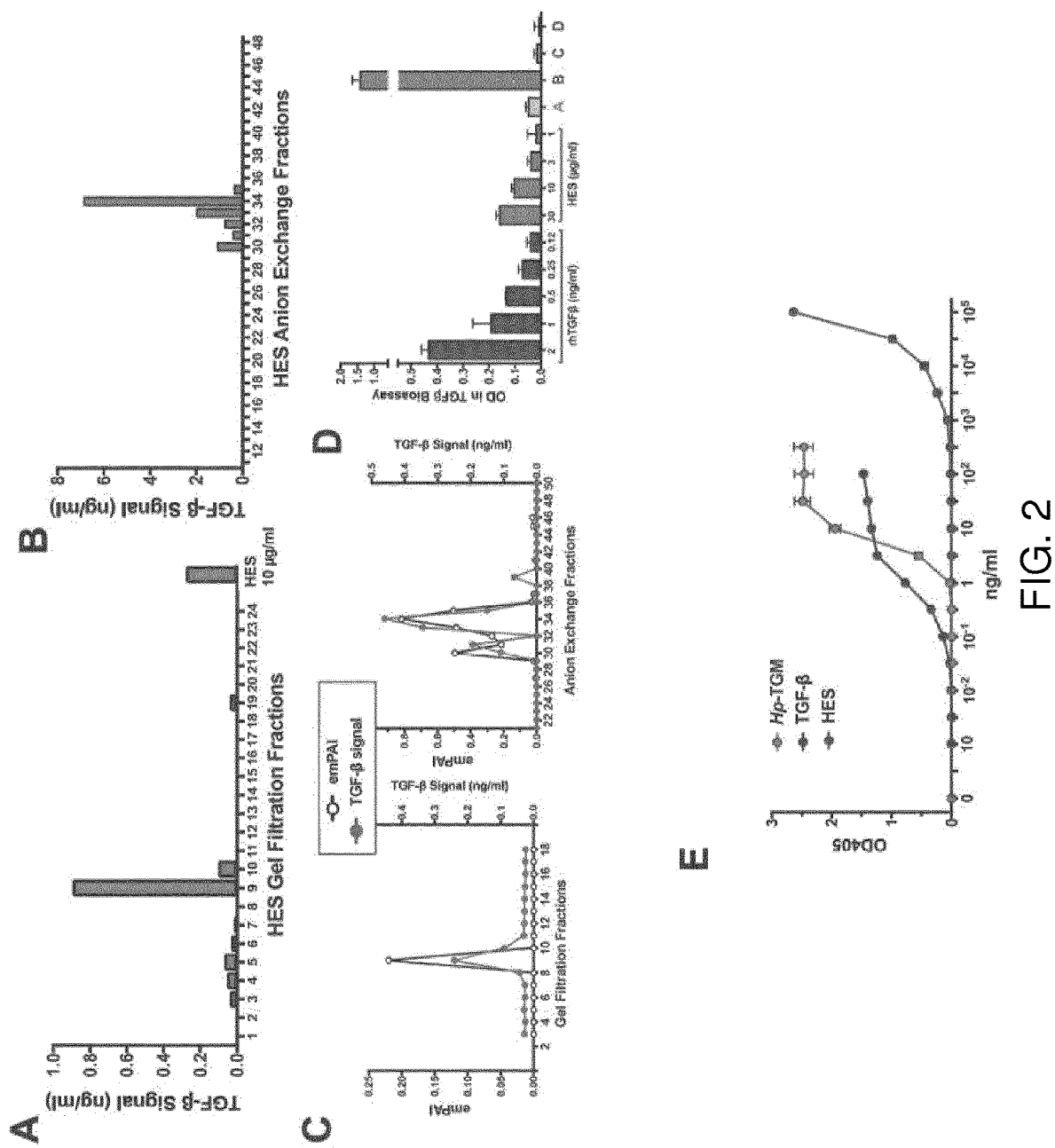

A. The deduced amino acid sequence of TGM (SEQ ID NO: 20) (*H. polygyrus* TGF-β Mimic). The predicted signal peptide (amino acids 1-18) is indicated in red; cysteine residues are shown in yellow and 5 potential N-glycosylation sites (NxS/T) in green. Peptides identified by mass spectrometry (263-243) are underlined.

B. Alignment of five similar domains (TGM-19-95(SEQ ID NO: 2), TGM-69-176(SEQ ID NO: 3), TGM-177-262 (SEQ ID NO: 4), TGM-263-343 (SEQ ID NO: 5), and TGM-344-422(SEQ ID NO: 6)) within TGM encompassing the entire amino acid sequence apart from the predicted signal peptide (aa 1-18), with conserved cysteine (white on red) and other residues indicatedtogether with a Complement Control Protein (CCP) module from the nematode *Ascaris suum* (domain 12 of ASU_08405, aa 954-1018) (SEQ ID NO: 48), and an archetypal CCP domain, human Factor H module 1 (X07523, aa 20-83) (SEQ ID NO: 49). Other conserved residues are shown in red and potential N-glycosylation sites outlined in green. Amino acid positions for each domain of TGM are indicated on the left. Note the presence of a 15-aa insertion near the N-terminal of each domain of TGM which is not typical of the CCP family. Positions of disulphide bonds in Factor H are shown below the alignment by linked cysteine residues CI-CIV.

C. Exon-intron structure of TGM in the *H. polygyrus* genome; domains are coloured corresponding to symbols in panel B; positions of cysteine residues indicated in black circles. Numerals denote amino acid residue numbers for each domain.

FIG. 2

A. Fractionation of HES by gel filtration FPLC. 1 mg of HES was separated on a Superdex 200 10/300 GL column and 1 ml fractions collected for assay with MFB-F11 reporter cells; responses were calibrated with recombinant human TGF-β1.

B. As A, fractionation by ion exchange FPLC on a Mono Q™ 5/50 G column.

C. Abundance of a candidate protein, Hp_103161_IG00349_L1408, calculated by the exponentially-modified Protein Abundance Index (emPAI) in each fraction, compared to the activation of TGFβ-responsive cells by the same fraction.

D. TGF-β bioassay results of four candidate recombinant clones designated A-D; clone B corresponds to candidate Hp_103161_IG00349_L1408 shown in panel C.

E. MFB-F11 TGF-β-responsive bioassay for activity following 24 hours of culture at 37° C., comparing TGM to hTGF-β1 and the complex HES mixture by protein concentration. MFB-F11 cells are transfected with a Smad-responsive plasmid construct in which TGF-β binding leads, through Smad phosphorylation and nuclear translocation, to expression of alkaline phosphatase, which is measured following the addition of p-nitrophenyl phosphate. Data shown are representative of >3 independent experiments.

FIG. 3.

A-C. A range of concentrations of recombinant human TGF-β, TGM or HES were cultured with MFBF11 TGF-β bioassay cells (A), or sorted CD4+ mouse (B) or human (C) cells. TGF-βR signaling was assessed by secreted alkaline phosphatase levels (A), or Foxp3+ cells within the CD4+ population by flow cytometry (B,C).

D,E. Abolition of signalling by inhibitors of the TGF-β receptor kinases. Activity shown from MFB-F11 bioassay after 24 hours of culture of TGF-β and TGM at 37° C. with: (D) the TβRI inhibitor, SB431542 or DMSO control and (E) the TβRII inhibitor, ITD-1 (10 μM).

F. Western blots (Smad2 and phospho-Smad2): cell lysates from C57BL/6 splenocytes following culture at 37° C. for 18 hours. Culture conditions in duplicate: media (DMEM+2.5% FCS), media supplemented with 20 ng/ml hTGF-β1 and media supplemented with 20 ng/ml Hp-TGM.

G. Densitometric analysis of bands with Image Studio (version 5, Li-Cor), presented as ratio of phospho-Smad2 normalised to Smad2 for each sample.

H. Activity shown from MFB-F11 bioassay after 24 hours of culture at 37° C. with hTGF-β1 or TGM incubated with anti-TGF-β monoclonal antibody or MOPC31C IgG control.

FIG. 4

Mass spectrometric profiles of candidate proteins. Protein abundance profiles for all candidate proteins found in both gel-filtration (upper panels) and ion exchange (lower panels) fractions with peak TGF-β activity, except for Hp_103161_IG00349_L1408 shown in FIG. 2 C.

FIG. 5

Expression of recombinant TGM.

A. Secreted purified recombinant TGM from transfected HEK293T cells analysed by SDS-PAGE electrophoresis and Coomassie Blue staining.

B. Western blot analysis with anti-penta-His antibody

FIG. 6

TGM induces de novo Foxp3 expression in murine and human CD4+ T cells and induces greater Foxp3 expression than hTGF-β at high concentrations.

A, B. CD4+CD25-GFP-CD62L$^{hi}$ murine naive T cells were stimulated with plate-bound anti-CD3/CD28 for 4 days in culture with 100 U/ml IL-2 and variable concentrations of TGM or hTGF-β1, before flow cytometric analysis of CD4, CD25 and Foxp3 expression; 2 technical replicates per concentration; representative of 4 independent experiments. A: percentage of CD25$^+$Foxp3$^+$ cells among total CD4$^+$ cells; B, Mean fluorescence intensity (MFI) of Foxp3 among Foxp3$^+$ cells.

C-E. Foxp3 induction in the same conditions as A, in the presence of SB431542 inhibitor (C) or pan-vertebrate anti-TGF-β (D, E); 2 technical replicates per concentration; representative of 3 independent experiments.

F-H. Human peripheral blood mononuclear cells were separated from red blood cells over a Ficoll gradient and CD4$^+$ T cells isolated by MACS positive selection. Isolated cells were cultured at 37° C. for 96 hours with a 1:1 ratio of CD3/CD28 Dynabeads® and variable concentrations of hTGF-β1 or TGM. Induction of Tregs from human peripheral blood monuclear cells (or just PBMCs if the terms has been used before) F: Representative flow cytometry plots (CD4+ population shown) MACS CD4+ positive selected PBMCs stimulated with Hp-TGM, hTGF-β or Il-2 respectively; G: percentage of CD25+Foxp3+ cells among total CD4$^+$ cells; H, MFI of Foxp3 among Foxp3$^+$ cells; 2 technical replicates per concentration; representative of 2 independent experiments.

FIG. 7

TGM drives immune regulation in vitro and in vivo.

A. Murine Foxp3$^+$ Treg are functionally suppressive in vitro. Foxp3$^+$ Treg were generated in vitro (as in FIG. 3 A) with 38.2 ng/ml TGM or 10 ng/ml hTGF-β. After four days of culture, CD4$^+$CD25$^+$GFP$^+$ cells were isolated by FACS. A single cell suspension was then freshly prepared from Foxp3-GFP mice to provide naive CD4$^+$CD25$^-$GFP$^-$ responder cells. Treg were cultured with responder cells, irradiated APCs and soluble CD3 for 5 days and proliferation was assessed by thymidine incorporation. The percentage suppression (in relation to responder cells with APC, CD3 and no Treg) of TGM- and TGF-β-generated iTreg are shown for varying ratios of Tregs:Teffector cells; 3 technical replicates per concentration; representative of 2 independent experiments.

B. TGM prolongs survival of fully-allogeneic skin grafts. Kaplan-Meier curve of full-thickness skin graft survival: allograft only (BALB/c to C57BL/6 skin graft, n=6), allograft+HES or TGM (BALB/c to C57BL/6 skin graft immediately preceded by implantation of intraperitoneal osmotic minipumps eluting 79.2 ng/day of TGM, n=6) and syngeneic grafts (C57BL/6 to C57BL/6 skin graft controls, n=3). Mantel-Cox comparison of allograft vs. allograft+Hp-TGM survival curves: p=0.0136.

C, D Histological analyses of graft tissue sites 7 days following transplantation of syngeneic or fully allogeneic BALB/c to C57BL/6 skin grafts; C, representative images of tissues sections; D, scoring of tissue inflammation performed in blinded fashion on 3 sections per graft; syngeneic control graft (n=7), allograft+control protein minipump (n=14), allograft+HES minipump (n=13), allograft+TGM minipump (n=12); data comprised of two independent experiments. HES vs untreated allogeneic control p=0.0493; TGMv untreated control p=0.0397, by unpaired t test.

E-I. Treg and Th17 phenotypes within CD4+ T cell populations 21 days after transplantation, E. Draining lymph node staining for Foxp3 [syngeneic control grafts (n=3), allograft+control protein (n=6), allograft+TGM minipump (n=6); comparison of groups with two-tailed, unpaired t test: t=0.0042]

F. Foxp3 expression among CD4$^+$ cells in the spleen of syngeneic or fully allogeneic skin graft recipients with or without administration of TGM, 21 days following transplantation [syngeneic control grafts (n=3), allograft+control protein (n=6), allograft+TGM minipump (n=6); comparison of groups with two-tailed, unpaired t test: p=0.0025].

G. Spleen cell staining for RORγt [syngeneic control grafts (n=3), allograft+control protein (n=7), allograft+TGM minipump (n=6); comparison of groups with two-tailed, unpaired t test: t=0.0112].

H Tbet expression in draining lymph node of syngeneic or fully allogeneic skin graft recipients with or without administration of TGM, 21 days following transplantation [syngeneic control grafts (n=3), allograft+control protein (n=6), allograft+TGM minipump (n=6); comparison of groups with two-tailed, unpaired t test: p<0.0001].

I. As H, at 7 days post-transplantation [syngeneic control grafts (n=3), allograft+control protein (n=6), allograft+TGM minipump (n=6); comparison of groups with two-tailed, unpaired t test: p<0.0001].

FIG. 8

Protective effects of TGM in the T cell transfer mouse model of colitis. A. Experimental outline and summary of time points for insertion of osmotic minipumps (d-1), transfer of T cells (d0) and analysis of intestinal inflammation (d60). B. Summary of inflammatory response in intestinal tissue, assessed on 15-point histopathological scale measuring crypt architecture, ulceration, crypt abscesses, goblet cell loss, mucosal inflammatory infiltration and submucosal inflammatory infiltration. C. Example histopathological staining with haematoxylin and eosin (H&E) in sections of intestinal tissue from mice receiving ovalbumin (OVA) or TGM.

FIG. 9

Domain structure of TGM variants -TGM, TGM-a and TGM-d have been verified as active.

FIG. 10

Alignment of TGM Sequences which are active (TGM (SEQ ID NO: 20), TGM-a (SEQ ID NO: 23) and TGM-d (SEQ ID NO: 32)) or inactive (TGM-b (SEQ ID NO: 26)).

FIG. 11

TGM truncation constructs, made to express protein containing 1-4 of the 5 domains as indicated. Truncated nucleotide sequences corresponding to the indicated domains were constructed in pSecTag plasmids and used to transfect HEK cells; supernatant from transfected cells was analysed by SDS-PAGE and Western Blot (Lower Right Hand panel), showing that all truncated proteins were expressed although levels of expression of Domain 1 and Domain 5 were relatively low (position on the Western Blot indicated by asterisks). Numerals on the left of the Western Blot denote mol.wt in kDa.

FIG. 12

Analysis of activity in truncation constructs.

DETAILED DESCRIPTION

The inventors have taken a fractionation approach to identify immunomodulatory proteins contained within HES, in order to develop these as potential drugs for use in human inflammatory disease. They fractionated HES by size (by gel filtration chromatography) and by charge (using anion exchange chromatography) to yield 20-30 individual fractions, each of which contained a small pool of molecules. These fractions were then assessed for TGF-β signalling ability using the MFB-F11 TGF-β bioassay described by Tessuer in 2006[25]. (see FIG. 2).

Relative abundances of proteins present in all size and charge fractions were assessed by LC-MS/MS mass spectrometry, referenced to an in-house generated transcriptome and proteome of *H. polygyrus* and HES.

Using cross-referencing of immunomodulatory activity to relative abundances by both methods of fractionation, the inventors were able to identify a small number (<10) of candidate proteins. The genes encoding these were codon optimised and cloned for expression in HEK293 mammalian cells. Recombinant proteins were tested for TGF-β signalling, using the MFBF11 assay described above. This technique resulted in identification of TGM (TGF-β mimic) which stimulates a stronger signal in said assay than mammalian TGF-β itself (FIG. 2 E).

Figure 3:
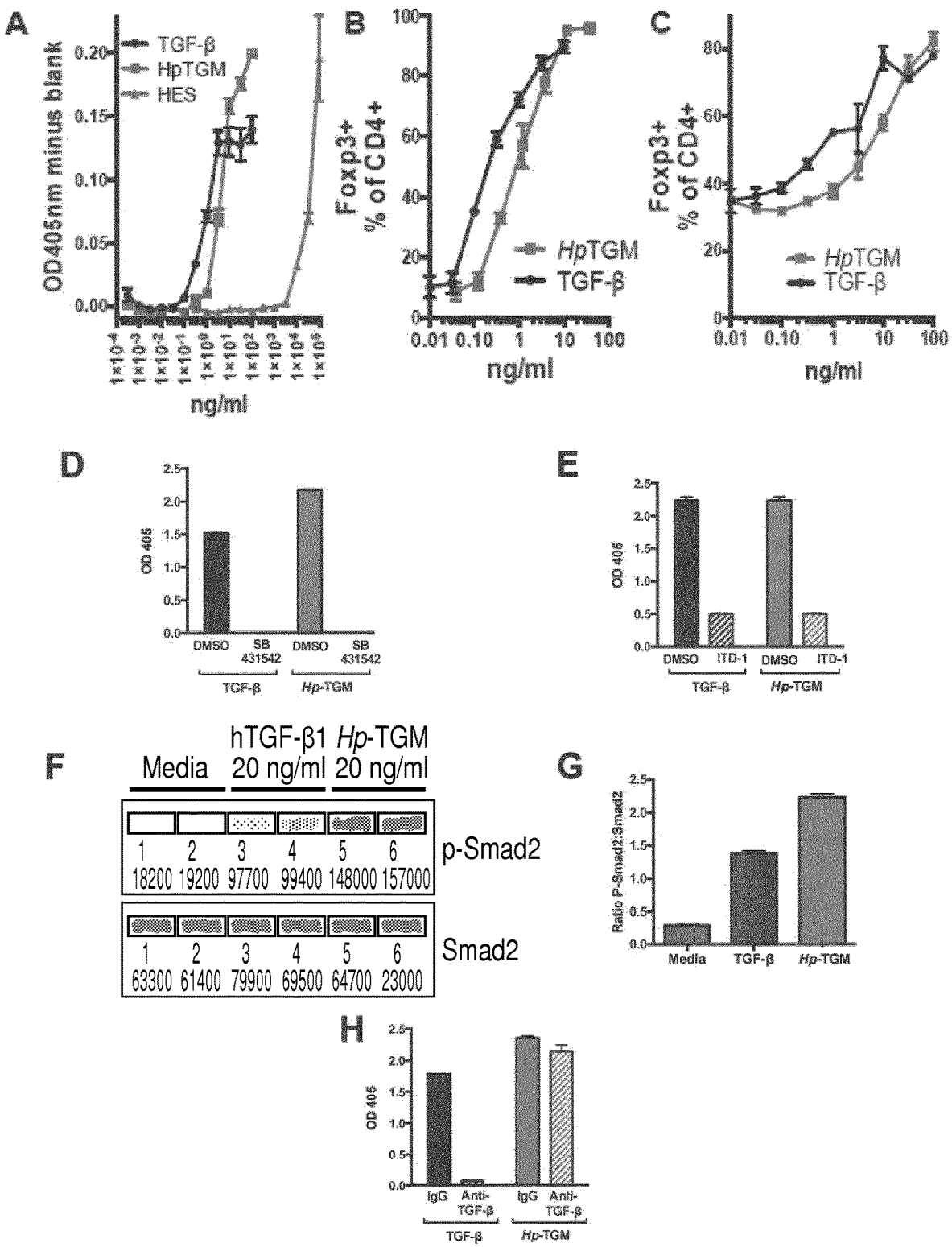

TGM can signal through the mammalian TGF-β receptor at concentrations close to that of recombinant active human TGF-β (FIG. 3 A). Furthermore, it shares the ability of mammalian TGF-β to induce CD4+Foxp3+ Tregs in vitro, in both murine (FIG. 3 B) and human (FIG. 3 C) assays. Thus it can translate directly for use in humans. TGM and recombinant mammalian TGF-β signalling are both ablated on administration of TGF-βR inhibitors such as SB431542 (FIG. 3 D) and ITD-1 (FIG. 3 E), and both cause Smad-2 phosphorylation with a strong signal transduced by TGM (FIG. 3 F, G). However, anti-TGF-β blocking monoclonal antibody 1 D11 fully blocks the effects of rhTGF-β, but not those of TGM.

Despite having very similar action to mammalian TGF-β, TGM has no sequence similarity with TGF-β, and has no known homologues in any other organism. The sequence of TGM predicts a 46.9 kDa protein, with 22 cysteine residues, and 5 predicted N-glycosylation sites. The high proportion of cysteine residues may indicate multiple disulphide bonds, which makes the protein particularly stable. Experimental data supports this: TGM heated to 37° C. for 28 days lost no detectable activity. *H. polygyrus* contains a family of TGM homologues, which the inventors have tested for TGF-β signalling ability. Comparison of sequence similarity with TGF-β signalling will identify minimal motifs required for binding, and lead to the provision of peptide mimetics for development as stable, non-immunogenic, tissue-penetrative drugs.

Materials and Methods

Animals. Inbred female C57BL/6J OlaHsd, BALB/c OlaHsd, and Foxp3-GFP reporter mice[26] were used for experiments, aged 6-12 weeks old and bred in-house or purchased from Harlan Laboratories. All animal experiments were performed under UK Home Office license and supervised by the Veterinary Services at the Universities of Edinburgh and Glasgow.

Fractionation of HES and Mass Spectrometric Analysis of HES Fractions.

Figure 4:
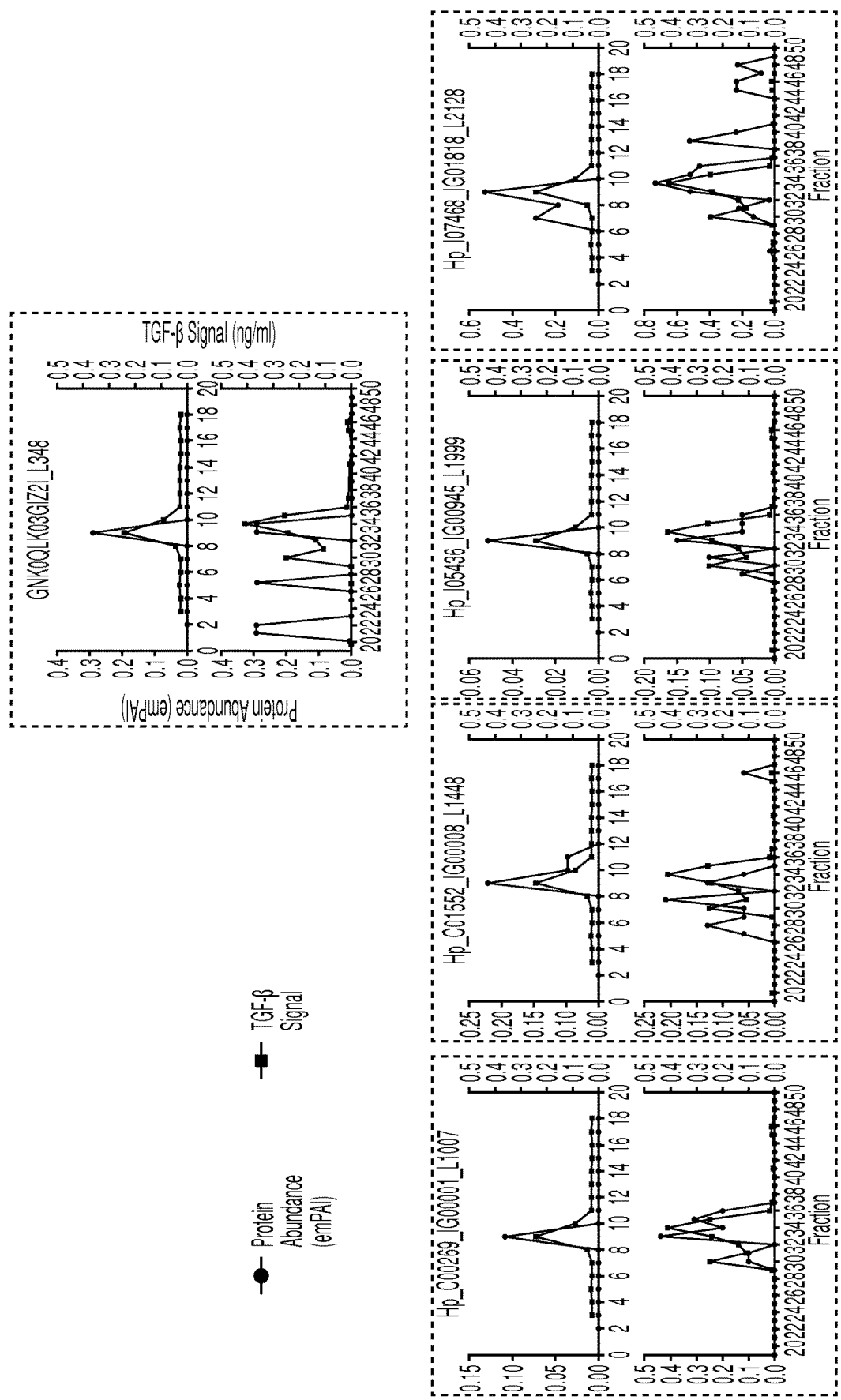
Figure 4:
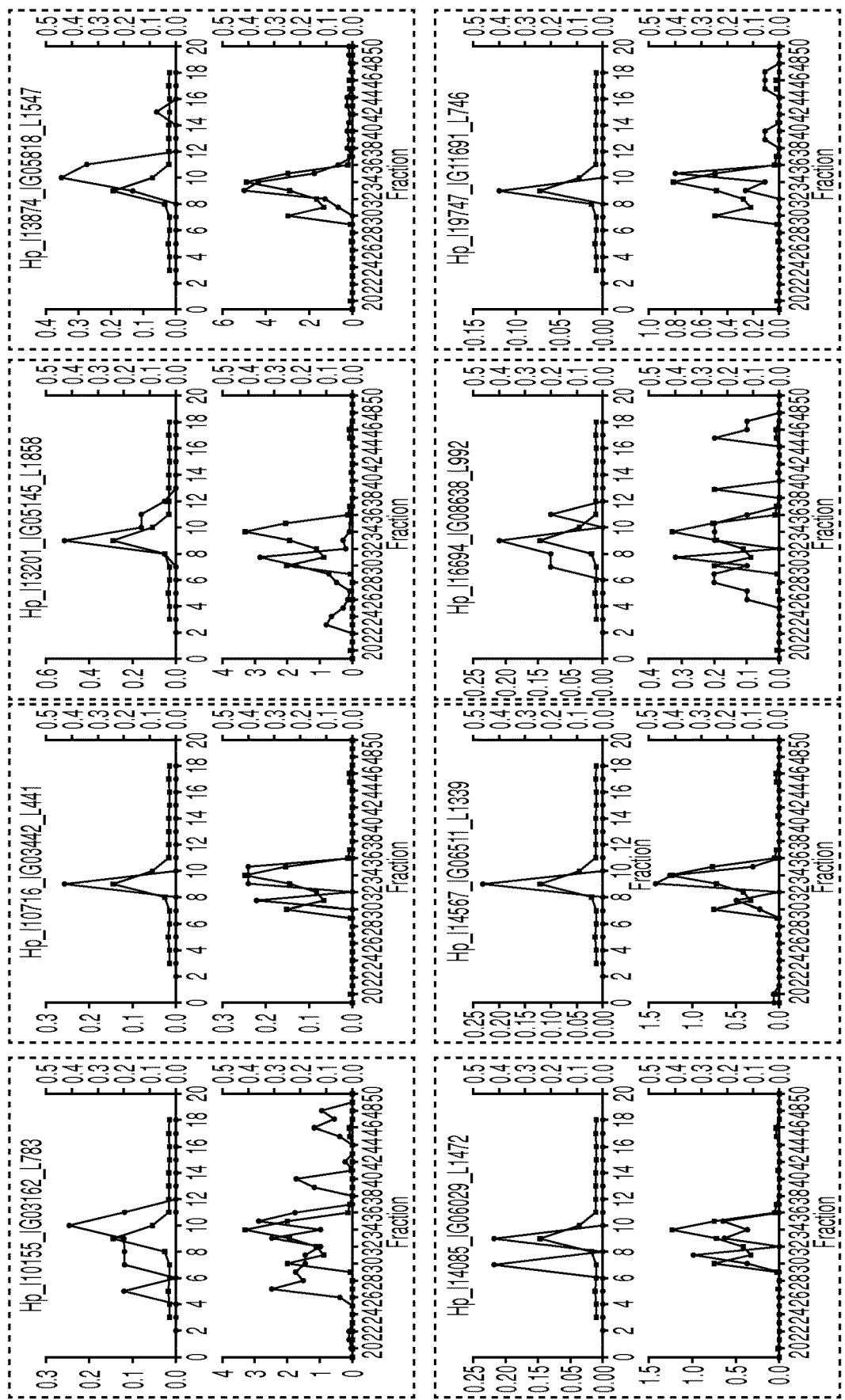
Figure 4:
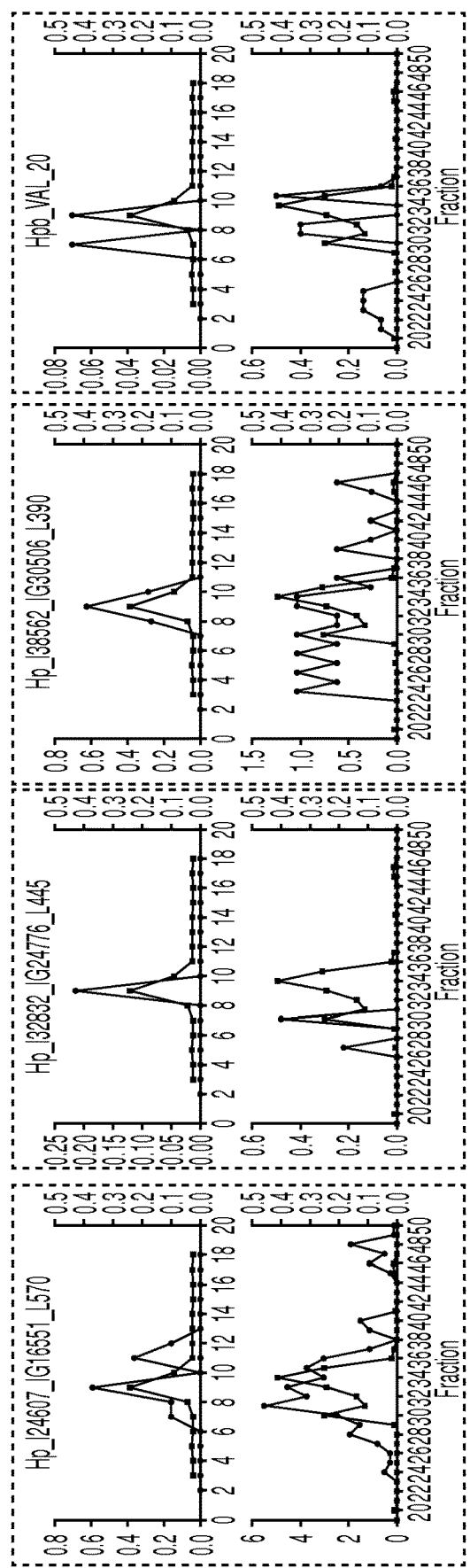

Heligmosomoides polygyrus Excretory Secretory (HES) products were prepared as described elsewhere[21]. HES was separated into 1 ml fractions using an ÄKTApurifier™ (GE Healthcare) using either the Superdex 200 10/300 GL column (GE Healthcare) for gel filtration fractionation or the Mono Q™ 5/50 GL (GE Healthcare) for anion exchange fractionation. The protein concentration of fractions was measured by Pierce BCA Protein assay kit (Thermo Scientific) with 5 μg of each fraction being trypsin digested, analysed using an Orbitrap mass spectrometer and then compared to an in house *H. polygyrus* transcriptomics database using Mascot. The significance threshold for consideration of proteins was p=0.05. Proteins with a score below 20 were not considered. Scripts written in Python 2.7 were used to analyse the mass spectrometry results shown in FIG. 2 C and FIG. 4.

Figure 5:
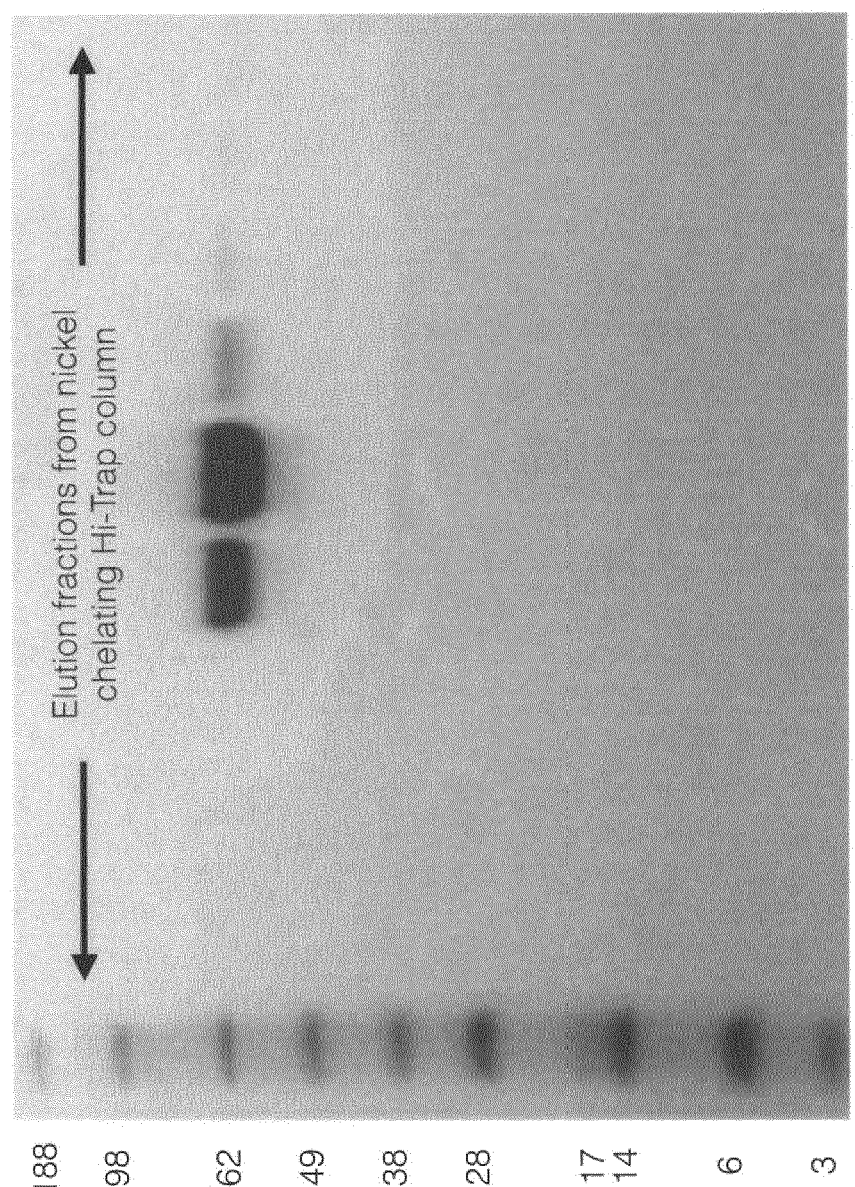

Recombinant TGM. Recombinant TGM was synthesised as a mammalian codon optimised insert (GeneArt) and cloned into the mammalian expression vector pSECTag2a (Invitrogen). The construct was transfected into HEK293T cells using the calcium chloride transfection method (Promega) and recombinant TGM was purified from culture supernatant by Ni-chelating chromatography (FIG. 5).

Antibodies and Inhibitors. The mouse monoclonal pan-isoform specific TGF-β IgG antibody, 1 D1127, was purchased (BioXCell), as were the inhibitors SB431542 (Tocris Bioscience) and ITD-1 (Tocris Bioscience). The mouse IgG1 myeloma MOPC 31C from ATCC (ECACC-90110707) was used as an isotype control. Smad2/3 antibody (Cell Signaling Technology) and phosphoSmad2 antibody (Cell Signaling Technology) was used as the primary antibody for Western blots, followed by Goat anti rabbit IgG-HRP secondary (BioRad) according to manufacturer's protocols. Recombinant TGM was detected by Western blot using an anti penta-His-HRP conjugate (Qiagen).

TGF-β Bioassay. The TGF-β bioassay (MFB-F11) developed by Tesseur et al.[25] was used with embryonic fibroblasts from TGF-β1$^{-/-}$ mice stably transfected with a TGF-β-responsive reporter plasmid containing a secreted embryonic alkaline phosphatase reporter gene (SBE-SEAP). MFB-F11 cells were grown in DMEM with 10% FCS, 100 U/ml penicillin, 100 μg/ml streptomycin, 2 mM L-glutamine and supplemented with 15 μg/ml Hygromycin B (Invitrogen), for 3 days. Cells were tested and found to be *mycoplasma*-free. Confluent cells were detached with trypsin, and resuspended in DMEM with 2.5% FCS, 100 U/ml penicillin, 100 μg/ml streptomycin and 2 mM L-glutamine at a concentration of $4 \times 10^5$ cells/ml. In 50 μl, $4 \times 10^4$ cells were added to each well of a 96-well round-bottomed plate. Serial dilutions of test substances HES (in-house), TGM (in-house), and recombinant human TGF-β1 (R&D Systems) were then added to each well in a volume of 50 μl and incubated for 24 hours at 37° C. Subsequently, 20 μl of supernatant was aspirated from each well, added to an ELISA plate (NUNC) with 180 μl of reconstituted Sigma Fast™ p-nitrophenyl phosphate substrate and incubated at RT in the dark for up to 4 hours. Plates were read on at 405 nm on an Emax precision microplate reader (Molecular Devices).

Cellular Immunology Assays. Single cell suspensions were made from murine spleen and lymph node specimens by maceration through 70 μm filters (BD) into complete RPMI 1640 (cRPMI) medium containing HEPES (Gibco), supplemented with 2 mM L-glutamine, 100 U/ml penicillin and 100 μg/ml streptomycin (Gibco), 10% heat-inactivated foetal calf serum (FCS) (Gibco), and 50 nM 2-mercaptoethanol (Gibco). Contaminating red blood cells were removed by resuspending the cells from one spleen in 2 ml of red blood cell lysis buffer (Sigma) and incubating at RT for 2 minutes. Cells were then washed with cRPMI and counted on a haemocytometer by trypan blue exclusion. For human lymphocytes, fresh peripheral blood was obtained by venepuncture of healthy volunteers under a protocol approved by the University of Edinburgh research ethics committee. Blood was collected into heparinised tubes (BD)

and immediately diluted 1:1 with PBS, centrifuged over Ficoll-Paque (GE Healthcare) at 400 g for 40 minutes at RT with no brake, and PBMCs recovered from the interface before three further washes in cRPMI at 200 g for 10 minutes (RT). Finally, cells were counted on a haemocytometer in preparation for culture.

Flow Cytometric Analysis and Cell Sorting. For viability staining, LIVE/DEAD® fixable blue (Life Technologies) was diluted to 1:1000 in PBS; 200 µl was added to each sample of cells, which were then incubated in the dark for 20 min at 4° C. (protected from light) and washed twice in FACS buffer. To prevent non-specific antigen binding, cells were incubated with 50 µl of polyclonal IgG (diluted 1:50 in FACS buffer) for 10 minutes at 4° C. and then washed twice in FACS buffer. All samples were acquired on a BD Biosciences LSR II or LSR Fortessa flow cytometer and analysed using FlowJo software (Tree Star).

The following FACS antibodies were diluted to an appropriate final concentration in FACS buffer (or permeabilisation buffer (eBioscience) for intracellular antibodies): Anti-CD3-FITC (17A2, Biolegend); anti-CD4-AF700 and -BV650 (RM4-5, Biolegend); anti-CD8-PerCP (53-6.7, Biolegend); anti-CD25-APC (PC61-5, eBioscience); anti-Foxp3-ef450, (FJK-16s, eBioscience), anti-ROR-gamma(t)-PE (AFKJS-9, eBioscience); anti-Tbet-PerCP-Cyanine (eBio4BIO, eBioscience) to a total volume of 50 µl diluted antibody per $5 \times 10^6$ cells. Single stain controls were individually added to one drop of UltraComp eBeads (eBioscience). Samples were incubated for 20 min at 4° C., washed twice in FACS buffer and then resuspended in 200 µl FACS buffer for acquisition of surface marker data directly or further processed for intracellular staining.

Transcription Factor Staining. For analysis of transcription factors, cells were resuspended in 400 µl fixation/permeabilisation buffer (eBioscience) and incubated at 4° C. for between 1 and 18 hours. Following incubation, cells were resuspended and washed twice in 1 ml permeabilisation buffer (eBioscience). 50 µl of antibody or isotype control (diluted in permeabilisation buffer) was added to each sample. Cells were resuspended by gentle vortex and incubated at room temperature for 30 minutes. Finally, cells were washed in 2 ml of FACS buffer and resuspended in 200 µl FACS buffer for acquisition.

CD4+ T Cell Enrichment by Magnetic Sorting. Cells were resuspended in MACS buffer at a volume of 45 µl per $10^7$ cells, together with 5 µl of microbeads (L3T4, Miltenyi Biotech), and incubated at 4° C. for 20 minutes. Cells were then washed three times in MACS buffer, centrifuging at 200 g for 5 minutes, and resuspended in MACS buffer at a volume of 50 µl per $10^7$ cells. CD4+ cells were then isolated by performing a positive selection using an AutoMACS (Miltenyi Biotech) automated magnetic column as per the manufacturer's instructions. The positive fraction of cells was then resuspended in MACS buffer and counted.

Fluorescence-Activated Cell Sorting. CD4+ cells (freshly isolated or from culture) were enriched by magnetic sorting as above and then incubated with antibodies for surface markers as described above, but with the omission of a viability stain. Following staining, cells were resuspended in MACS buffer at a concentration of $5 \times 10^8$ cells per ml. Sorting was performed on a BD FACSAria with a gating strategy of: lymphocytes (by forward and side scatter), single cells and then stained populations, e.g. $CD4^+CD25^-Foxp3^-CD62L^{hi}$. Cells were sorted into 2 ml of FCS (Gibco) and a sample from each tube was re-acquired on the FACSAria to assess the purity of each sort.

Foxp3+ Treg Induction Assay. A single cell suspension was prepared from the spleen and peripheral lymph nodes of Foxp3-GFP transgenic mice. CD4+CD25− GFP-CD62Lhi cells were then isolated by MACS followed by FACS sorting (see previous sections). Sorted cells were washed twice in complete RPMI and then resuspended in complete RPMI at a concentration of $5 \times 10^5$ cells per ml. CD3/CD28-coated 24 well plates (Costar) were prepared by adding 250 µl per well of CD3 and CD28 (eBioscience), both at 2 µg/ml in PBS, incubating for 2 hours at 37° C. and then washing 3 times in PBS. $5 \times 10^5$ cells were then added to each well in 1 ml of complete RPMI. Each well was made up to final volume of 2 ml complete RPMI, containing variable concentrations of treatment conditions (eg. TGF-β) and IL-2 (produced in-house) at a final concentration of 100 U/ml. Cells were removed after 96 hours for flow cytometric analysis.

Treg Suppression Assays. Tregs induced as above were washed in MACS buffer and the $CD4^+CD25^+GFP^+$ Treg population was isolated by FACS sorting. Responder cells $(CD4^+CD25^-GFP^-CD62L^{hi})$ were also isolated from a fresh Foxp3-GFP transgenic mouse. $10^4$ responder cells were added to each well of a 96 well round-bottomed plate together with $10^5$ irradiated APCs, 2 µg/ml soluble CD3 stimulation and a variable concentration of Treg. Proliferation was assessed after 72 hours by thymidine incorporation.

Continuous Infusion via Osmotic Minipump. Alzet minipumps (Charles River UK) of 100 µl capacity were selected according to the duration of infusion required for individual experiments (model 1007D—7 days; model—1002-14 days; model 1004—28 days). Minipumps were filled with the substance for infusion (HES, TGM or PBS control) and primed overnight by incubation in PBS at 37° C.

Under general anaesthesia, abdominal fur was removed by shaving and the skin was prepared with chlorhexidine solution. The peritoneal cavity was accessed through an upper midline incision and the minipump was placed in the right paracolic gutter. Closure was in two layers with 5-0 undyed Vicryl® (Ethicon UK).

Skin Transplantation. Full-thickness skin transplantation was performed using a modified technique of that originally described by Billingham, Brent and Medawar[28]. Tail skin from donor mice was prepared immediately post-mortem, making a circumferential incision around the base of the tail and then extending the incision distally along the ventral midline. The tail skin was then stripped, placed into cold PBS and fashioned into three 1×1 cm squares.

Recipient animals were placed under general anesthesia prior to shaving the right flank and preparing skin with chlorhexidine solution. The graft bed was prepared by dissecting skin from the right flank, taking care to preserve underlying subcutaneous adipose tissue (for microvascular blood supply to the graft). Optimally, the skin defect created was slightly larger than the size of the graft (1 mm at each edge), so that the graft remained taught and the risk of seroma formation was minimised. Following placement of the graft onto the graft bed, it was secured in place with methylated flexible collodion (William Ransom & Son Ltd), applied sparingly along the wound edges. The grafts were covered with an iodine-impregnated non-adherent dressing (Inadine®, Johnson and Johnson Medical) and then secured in place with tape. Dressings were removed seven days after skin grafting under a brief general anaesthetic; any animals that managed to remove wound dressings before day 7 were excluded (prospectively) from the experiment as technical failures. Allografts were monitored on a daily basis following the removal of dressings and rejection was defined as more than 90% necrosis by surface area, or when the graft had completely left the recipient. Assessment of graft necrosis was performed in a blinded fashion—after surgery, graft recipients were placed into numbered cages; grafts were monitored according to cage number and were then matched to experimental groups for analysis at the end of each experiment.

Separately, skin grafts were harvested 7 days after transplantation and specimens were fixed in 10% buffered formalin solution overnight, then stored in 100% ethanol. Specimens were embedded in paraffin and then cut in 4 μm transverse sections. Haematoxylin and eosin (H&E) staining was then performed under automated protocol with a Gemini varistainer (Thermo Scientific), according to the manufacturer's instructions. Histological scoring of rejection was performed in a blinded fashion by a consultant histopathologist. Scoring was performed on three histological sections of each skin graft according to features of vasculitis, folliculitis, dermal inflammation and epidermal degeneration, as described by Zdichavsky et al[29]. Images were captured using a Leica DFC290 compound microscope and Leica Application Suite software.

T cell transfer model of colitis. Foxp3-negative CD4-positive T cells from normal naive Foxp3-GFP C57BL/6 mice were purified by fluorescence cell sorting, and transferred i.v. into naive RAG-1-deficient mice on the C57BL/6 background. Each mouse received 500,000 cells. Groups of recipient mice were implanted with osmotic minipumps (see above) releasing 50 ng per day of Ovalbumin (control protein) or TGM. Minipumps were impanted the day before T cell transfer and continuously released protein for 28 days. At day 60, mice were euthanused, intestinal tissues recovered and stained with haematoxylin and eosin (H&E), and analysed by microscopic evaluation of sections on slides. Colitic inflammation was assessed by a combined histology severity score, comprising a score of 0-3 based on each of the following six parameters: crypt architecture, ulceration, crypt abscesses, goblet cell loss, mucosal inflammatory infiltration and submucosal inflammatory infiltration.

Statistical Analyses. All statistical analyses were performed using Prism 6.0 (Graphpad Software Inc.). For comparisons of two groups, Student's two-tailed t test was used, assuming unequal variance. When three or more groups were analysed, a one-way ANOVA test was used with Tukey's multiple comparison test. Graft survival curves were compared by Kaplan-Meier analysis; the statistical significance of difference in survival between experimental groups was determined by a log rank chi-square test. P values of <0.05 were considered to be significant; the following symbols were used to indicate significance levels: * denoting p<0.05,  denoting p<0.01, * denoting p<0.001 and **** denoting p<0.0001. Sample sizes were chosen empirically on the basis of the lab's previous experience in the calculation of experimental variability (sample sizes for each experiment were not pre-determined by individual power calculations).

Results

To identify TGF-β-like activity, the inventors screened *H. polygyrus* excretory-secretory products (HES) for their ability to activate the MFB-F11 fibroblast cell line in which an alkaline phosphatase reporter is activated by the Smad pathway upon receptor ligation[25]. HES proteins were independently fractionated by gel filtration and anion exchange Fast Protein Liquid Chromatography (FPLC), and each fraction assayed for activity on the reporter cell line (FIG. 2 A, B). All fractions were then subject to mass spectrometric analysis for matching to a transcriptomic sequence database as previously described[21]. Eighteen candidate proteins were present in peak fractions from both gel filtration and anion exchange with differing degrees of abundance (Table 2); the inventors selected candidates to clone and express for which abundance (measured by exponential mass protein abundance index, emPAI) most closely matched biological activity in each fraction, as in the example shown in FIG. 2 C, and in FIG. 4.

TABLE 2

Abundance of 18 candidate proteins, including TGM Hp_I03161_IG00349_L1408, in FPLC fractions

| Protein | Gel Filtration Fraction 9 | | Anion Exchange Fraction 34 | |
|---|---|---|---|---|
| | emPAI | Rank (of 139) | emPAI | Rank (of 300) |
| GNK0QLK03GIZ2I_L348 | 0.29 | 138 | 0.29 | 293 |
| Hp_C00269_IG00001_L1007 | 0.10 | 87 | 0.20 | 213 |
| Hp_C01552_IG00008_L1448 | 0.21 | 29 | 0.06 | 202 |
| Hp_I03161_IG00349_L1408 | 0.22 | 35 | 0.92 | 26 |
| Hp_I05436_IG00945_L1999 | 0.05 | 130 | 0.05 | 246 |
| Hp_I07468_IG01818_L2128 | 0.53 | 13 | 0.74 | 30 |
| Hp_I10155_IG03162_L783 | 0.12 | 61 | 0.97 | 39 |
| Hp_I10716_IG03442_L441 | 0.24 | 100 | 0.24 | 197 |
| Hp_I13201_IG05145_L1858 | 0.49 | 11 | 0.11 | 140 |
| Hp_I13874_IG05818_L1547 | 0.13 | 77 | 4.33 | 4 |
| Hp_I14085_IG06029_L1472 | 0.21 | 47 | 0.37 | 25 |
| Hp_I14567_IG06511_L1339 | 0.23 | 44 | 1.25 | 26 |
| Hp_I16694_IG08638_L992 | 0.20 | 81 | 0.20 | 169 |
| Hp_I19747_IG11691_L746 | 0.12 | 136 | 0.12 | 284 |
| Hp_I24607_IG16551_L570 | 0.60 | 49 | 3.09 | 20 |
| Hp_I32832_IG24776_L445 | 0.22 | 66 | 0 | — |
| Hp_I38562_IG30506_L390 | 0.62 | 117 | 1.05 | 157 |
| Hpb-VAL-20 | 0.07 | 110 | 0 | — |

For each candidate, mammalian codon-optimised sequences were synthesized and cloned into the plasmid vector pSecTag2a for transfection of human embryonic kidney HEK293 cells and expression as recombinant proteins with hexa-histidine C-terminal tags. The supernatants of transfected cell cultures were collected and applied directly to the MFB-F11 assay. One transfectant (Hp_I03161_IG00349_L1408, the candidate shown in FIG. 2 C), showed a high level of stimulatory activity, far exceeding that of total HES; this clone is depicted as clone B in FIG. 2 D. From this clone, recombinant 49-kDa protein was expressed and purified by nickel chelating chromatography through affinity for the hexa-histidine tag. Following confirmation that the purified recombinant protein displayed TGF-β-like activity (see below), it was named *H. polygyrus* TGF-β Mimic (TGM).

The amino acid sequence of active TGM comprises 422 residues, of which the first 18 are predicted to form a classical signal peptide (FIG. 1 A), with the remainder forming a mature 404-aa protein containing 22 cysteine residues (yellow on black) and 5 potential N-glycosylation sites (green). The protein has no sequence similarity to the TGF-β family in which the mature active moiety is a disulphide-linked homodimer of two ~110-aa C-terminal polypeptides with 6-9 cysteine residues. However, the mature protein of TGM contains 5 homologous but non-identical ~80-aa domains each with distant similarity to the Complement Control Protein (CCP, or Sushi) family (FIG. 1 B). Moreover, the mature protein is encoded in an 11-exon gene in the parasite genome, corresponding to the signal peptide (Exon 1) and 5 pairs of exons whose boundaries exactly match those of the CCP domains (FIG. 1 C).

The inventors next tested the ability of purified recombinant TGM protein (FIG. 5) to activate MFB-F11 cells in vitro, in comparison to hTGF-β1 and HES; all three induced reporter cell production of alkaline phosphatase in a dose-dependent manner (FIG. 2 E). Notably, the primary TGM product proved to be active without the need for proteolytic processing to a mature form (as is the case for mammalian TGF-β). The response of MFB-F11 cells to increasing concentrations of TGM reached a maximum signal significantly greater than attained by even the highest concentrations of hTGF-β1 ($OD_{405}$ at 100 ng/ml, TGM=2.46±0.16 and hTGF-β1=1.48±0.02, p=0.02).

The MFB-F11 response to HES also exceeded the highest level of the TGF-β-induced signal, but required several log-fold higher concentrations to achieve the same signal as TGM (FIG. 2 E). This indicated that TGM represents less than 0.1% of the total protein present in HES, consistent with its low abundance ranking, from the mass spectrometric analysis even in the fractions that show peak TGF-β activity (Table 2).

The inventors then established if TGM signalling could be inhibited by antibody to mammalian TGF-β, as could be expected if the parasite molecule interacts with or activates the host molecule in tissue culture medium. MFB-F11 cells were first co-cultured with TGM or hTGF-β1 and 100 μg/ml pan-vertebrate anti-TGF-β antibody (clone 1 D11) or MOPC murine IgG control. Anti-TGF-β antibody considerably inhibited the MFB-F11 signal generated from hTGF-β1, but had no impact on TGM (FIG. 3 H).

To establish if TGM transduces canonical signaling following TGF-β receptor ligation, the MFB-F11 cells were stimulated in the presence or absence of inhibitors of receptor kinase activity. The inventors first tested the kinase inhibitor SB431542 which blocks phosphorylation by TβRI, as well as other TGF-β family type I receptors Alk5 and Alk7[30]. SB431542 has previously been found to block the TGF-β-like activity of unfractionated HES, and to render mice more resistant to *H. polygyrus* infection[9]. Both TGM and hTGF-β1 signals were completely ablated in the presence of SB431542 (FIG. 3 D). The inventors repeated this assay with 'Inducer of Type II TGF-β Receptor Degradation-1' (ITD-1)[31], which also completely ablated the MFB-F11 signal generated by TGM and hTGF-β1 (FIG. 3 E), indicating that both ligands signal through the same combination of type I and II receptors on mammalian cells.

Interestingly, in MFB-F11 cell assays, TGM generally induced a significantly higher signal than hTGF-β1. Further evidence that Hp-TGM can drive an enhanced TGF-β pathway signal was found when stimulating splenocytes from C57BL/6 mice.

Following overnight incubation with 20 ng/ml hTGF-β1 or 20 ng/ml Hp-TGM, cells were harvested and assayed for Smad2 phosphorylation by Western blotting. As shown in FIG. 3 F, G, Smad2 phosphorylation is seen at a higher level following stimulation with Hp-TGM.

Figure 6:
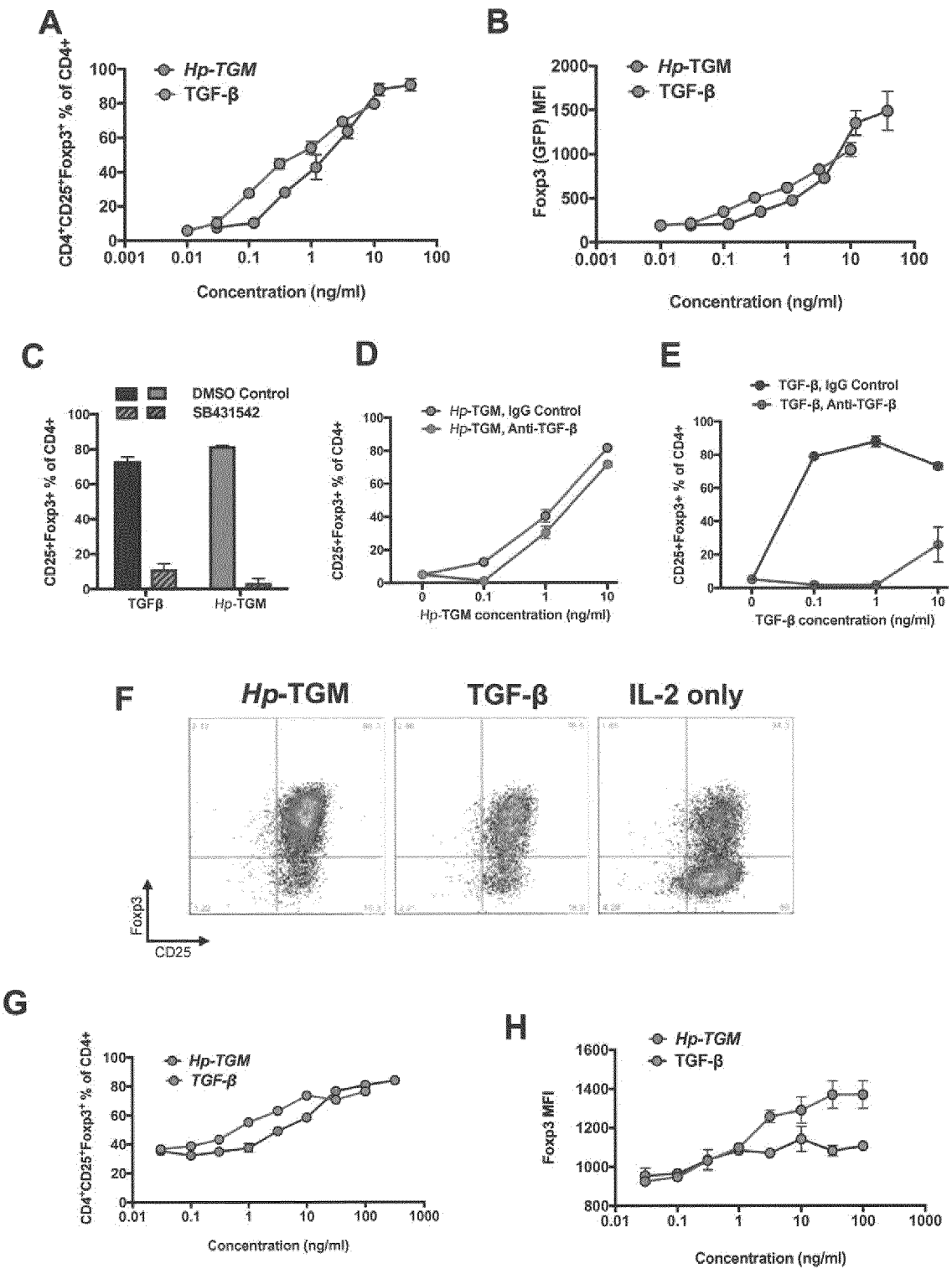

*H. polygyrus* and HES have previously been shown to induce Foxp3+ Treg in vitro and in vivo[8, 4, 24]. The inventors therefore next ascertained if TGM could induce Foxp3+ Treg differentiation in vitro and if the evidence of enhanced intracellular signalling would be reflected in the level of Foxp3 expression within the induced Treg population. CD4+ CD25−GFP−CD62L$^{hi}$ cells were isolated from Foxp3-GFP reporter mice[30] by MACS and FACS sorting, then cultured for 96 hours in Treg polarising conditions with hTGF-β1 or TGM. TGM was found to effectively induce Foxp3+ Treg differentiation: at the highest concentration tested (38.1 ng/ml, 0.78 nM) Hp-TGM induced Treg conversion in 90.65% (±3.55%) of all CD4+ cells, compared to 79.65% (±2.55%) induced by a similar molar concentration (10 ng/ml, or 0.78 nM monomeric hTGF-β1) of the human cytokine (FIG. 6A). Further, the mean fluorescence intensity of Foxp3 expression induced by high concentrations of TGM was found to be greater than that of the equivalent concentration of hTGF-β1 (FIG. 6 B). TGM-mediated induction of Foxp3 was completely abolished by the TGF-βRI kinase inhibitor SB431542 (FIG. 6 C), but not by pan-vertebrate anti-TGF-β antibody (FIG. 6 D), while the presence of either reagent blocked the effect of the mammalian ligand (FIG. 6 C, E).

The inventors then tested whether it could drive expression of Foxp3 in human CD4+ T cells purified from peripheral blood cultured with anti-CD3/CD28 Dynabeads and variable concentrations of TGM or hTGF-β1 for 96 hrs before assessment of CD25 and Foxp3 expression. As shown in FIG. 6 F, G the proportion of CD4+CD25+Foxp3+ Treg increased with TGM in a concentration-dependent fashion, to a maximum of 84% (±2.5%). The proportion of Treg of all CD4+ cells was similar for TGM and hTGF-β1 at most concentrations; however, at higher concentrations, the mean fluorescence intensity (MFI) of Foxp3 expression was significantly greater in Treg exposed to TGM compared to hTGF-β1 (FIG. 6 H).

Figure 7:
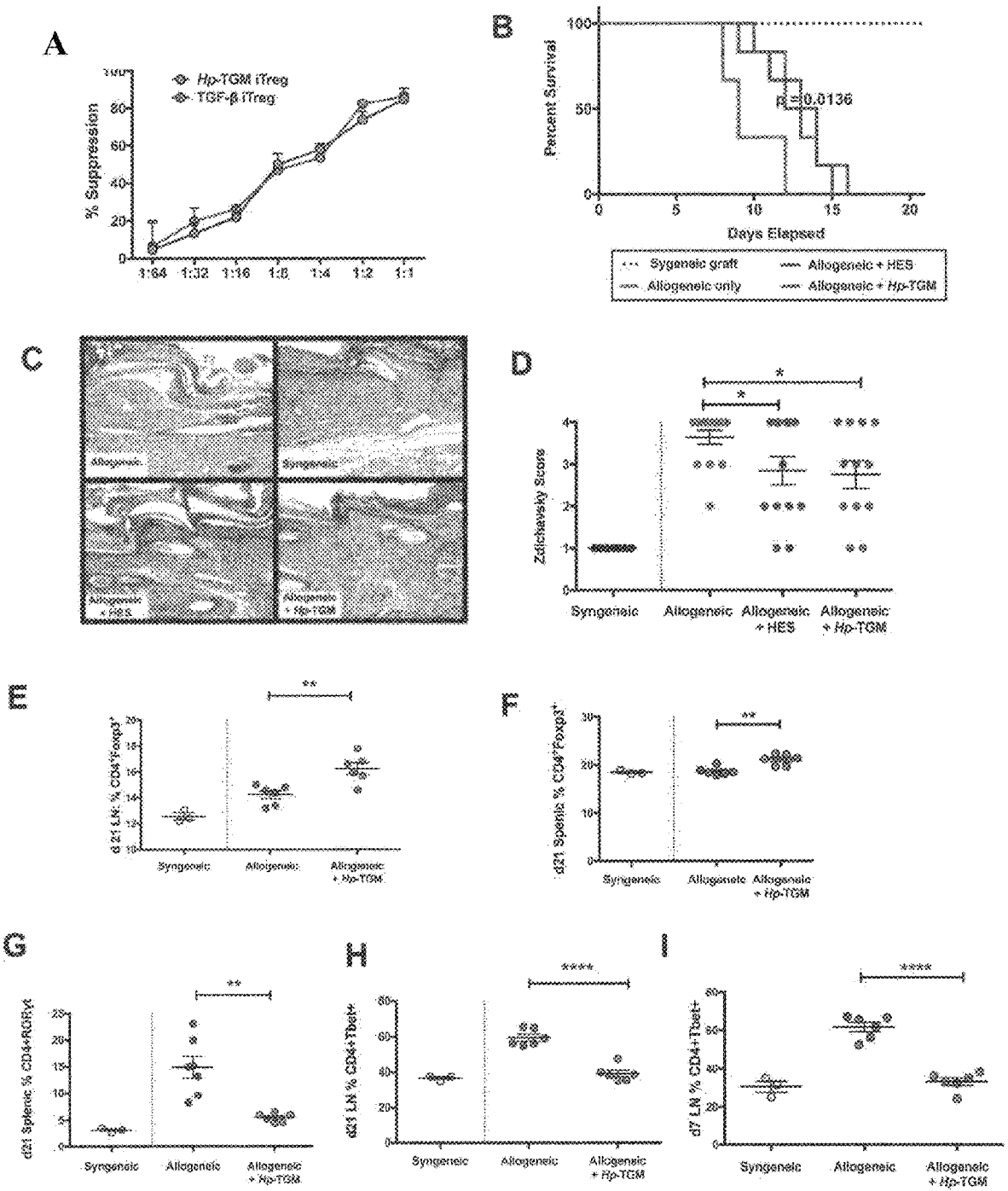

To further establish if TGM can induce immune suppressive function in naïve T cells, murine Treg generated from sorted CD4+CD25-GFP-CD62L$^{hi}$ cells incubated with hTGF-β1 and TGM were added to CD4+CD25-GFP-CD62L$^{hi}$ responder cells together with soluble anti-CD3 and irradiated APC. Assessment of responder cell proliferation by thymidine incorporation demonstrated that TGM-generated Treg are functionally suppressive in vitro with suppressive capacity equivalent to TGF-β-generated Tregs (FIG. 7 A).

To test the efficacy of TGM in an in vivo model of immunopathology, the inventors examined its effects in a model of allograft rejection, as helminth parasites and their products have been previously described to prolong the life of tissue transplants[32]. The inventors chose the fully-allogeneic skin transplant model, from BALB/c donor mice to C57BL/6 recipients, a system in which median rejection occurs in approximately 9 days, mediated by Th1 and Th17 inflammatory responses. This represents a robust and intense allogeneic reaction[33] but one which is known to be downmodulated by adoptive transfer of Treg populations[34]. TGM or HES were administered to mice through osmotic mini-pumps inserted intraperitoneally to continuously release parasite products in a manner akin to live infection. Both TGM and HES conferred a significant extension of allograft life, with median survival extended by ~5 days relative to untreated controls (FIG. 7 B).

In parallel experiments, inflammation at the graft site was assessed 7 days post-transplant in animals treated with HES or TGM, in comparison to controls. As shown in FIG. 7 C, both treatments reduced histological features of rejection such as dermal inflammation and epidermal degeneration. Sections were evaluated blindly using the Zdichavsky scoring system[29], revealing significantly attenuated rejection reactions in recipients of both HES and TGM (FIG. 7 D).

In allograft recipients exposed to TGM, a significant increase in Foxp3+ expression was observed in the allograft draining lymph node (FIG. 7 E) and spleen (FIG. 7 F) at day 21. Moreover, the expression of T cell RORγt, indicative of Th17 expansion induced by the allograft, was reduced in recipients of TGM to the level observed in syngeneic graft recipients (FIG. 7 G), as was expansion of Tbet+ Th1 cells (FIG. 7 H). In separate experiments, when lymphoid tissues were sampled 7 days following allografting, similar reductions of inflammatory cell phenotypes were observed, including diminished T-bet expression among total CD4+ T cells (FIG. 7 I).

Mammalian TGF-β is a multi-faceted molecule with effects beyond the regulatory T cell circuit, which can contraindicate its therapeutic use as an immunosuppressant or anti-inflammatory agent. Within the T cell compartment, TGF-β is associated with Th17 differentiation when IL-6 is present in vitro[35, 36], or when TGF-β is over-expressed in Freund's complete adjuvant-immunized mice[35]; the suppression of ROR-γt expression by TGM in allogeneic skin graft recipients suggests that the parasite ligand does not potentiate Th17 responses in vivo.

The inventors also demonstrated the protective effects of TGM in a mouse model of colitis. In this model, T cells depleted of the Foxp3-positive regulatory T cell population are transferred into lymphocyte-deficient RAG-1−/− mice; in the absence of regulatory T cells the transferred population become reactive to the intestinal microbiota and recipient mice develop intestinal inflammation known as colitis. TGM was administered through an osmotic minipump implanted subcutaneously on the day prior to T cell transfer, which released 50 ng per day of protein for 28 days. Control mice were implanted with minipumps containing the same quantity of ovalbumin (OVA). As shown in FIG. 8, TGM fully protected mice from colitis with little evidence of intestinal inflammation and very low scores on the histopathological assessment of crypt architecture, ulceration, crypt abscesses, goblet cell loss, mucosal inflammatory infiltration and submucosal inflammatory infiltration.

Identification of the Functional Domains of TGM from Heligmosomoides polygyrus. Mammalian codon-optimised TGM was synthesized by GENEart and inserted into a holding vector as described in the main manuscript. Amplification and cloning of truncated versions of TGM was then performed by PCR amplification using full length codon-optimised TGM as template DNA and domain-specific primers with restriction sites (AscI/ApaI) and cap sequence placed (gcgcgc) at either end (Table 3).

TABLE 3

| Primer | Sequence |
|---|---|
| coTGM_domain1F | gcgcgcGGCGCGCCgatgatagcggctgcatg |
| coTGM_domain2F | gcgcgcGGCGCGCCagatgcagcccctgccc |
| coTGM_domain3F | gcgcgcGGCGCGCCggctgtcctcccctgcctg |
| coTGM_domain4F | gcgcgcGGCGCGCCcggtgcaagcctctggaag |
| coTGM_domain5F | gcgcgcGGCGCGCCagaggctgcagcagcgacg |
| coTGM_domain1R | gcgcgcGGGCCCtctgtcgtcgcattcctgcac |
| coTGM_domain2R | gcgcgcGGGCCCgctggcaggacaggtag |
| coTGM_domain3R | gcgcgcGGGCCCggggtcggggcacttgcc |
| coTGM_domain4R | gcgcgcGGGCCCggcgttgatgcattccatcag |
| coTGM_domain5R | gcgcgcGGGCCCcagggtccggatgcc |

PCR reactions to amplify truncated TGM constructs used proofreading Taq polymerase Phusion Hi Fidelity Taq polymerase (NEB) with the following conditions:

Initial denaturation: 98° C. for 30s
35 cycles of:
Denaturing: 98° C. for 30s
Annealing: 55-65° C. for 30s
Extension: 72° C. for 30-90s (depending on truncation size)
Final extension of 72° C. for 10 mins
12° C. hold.

PCR reactions were electrophoresed through a 1.2% agarose gel and a single band of each predicted size of insert was gel extracted and cloned into pSECTag2A (Invitrogen) for transfection and expression in HEK293T cells, as described in the main manuscript.

The activity of raw expression supernatants were tested for TGF-β activity using the reporter cell line MFB-F11 as described above.

The full coding sequence of TGM was analyzed and found to be encoded by 11 exons in the parasite genome (FIG. 1 C); exon 1 corresponded to a conventional signal sequence, and all other exons except exon 8 were noted to contain 2 cysteine residues; exon 8 contained 4. A pattern was noted in which pairs of exons (2+3, 4+5, 6+7, 8+9, 10+11) showed similarly spaced cysteines, indicating that each two-exon unit represented a module or domain of 76-86 amino acids that had repeated over evolution to produce a 5-domain protein (FIG. 1 B). Further visual inspection revealed a distant resemblance to the ~60-aa CCP domain (Pfam00084) which was insufficient to be detected by automated algorithms in standard search packages.

Figure 9:
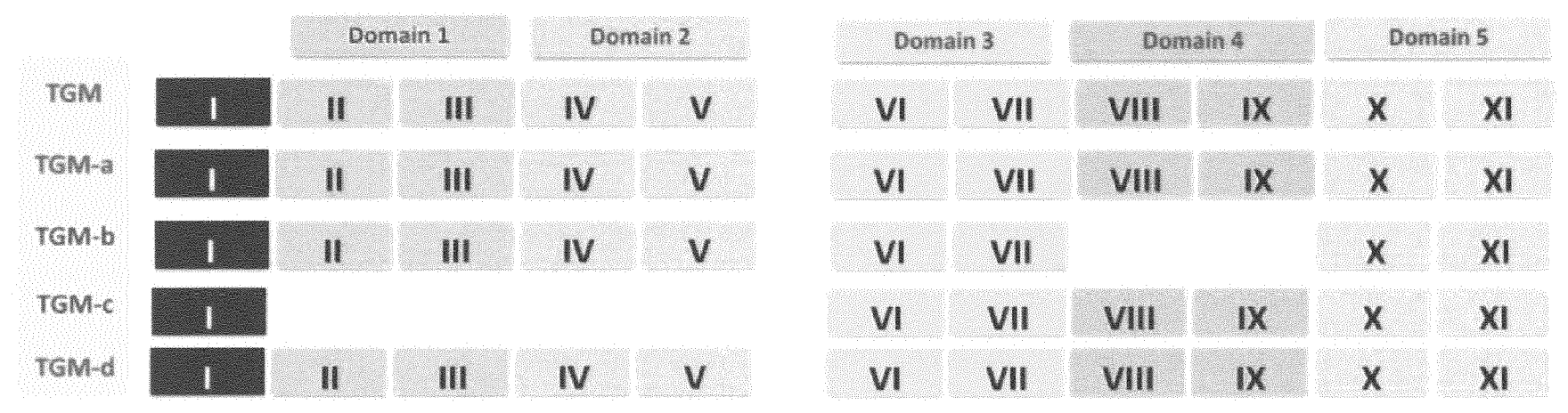

Further support for a 5-domain model was obtained by searching the in-house transcriptome database for related sequences. Two variants, termed TGM-b and TGM-c, were identified which were missing amino acids 263-343 (the entirety of exons 8+9, domain 4), and amino acids 19-176 (exons 2-5, domains 1+2) (FIG. 9). These discoveries indicated that the putative domains were discrete subunits which could be added or subtracted from the protein without compromising structure or solubility of the protein.

Notably TGM-b and TGM-c did not show biological activity. TGM-c is highly divergent (~50% amino acid difference) while TGMb also had significant amino acid divergence from TGM itself (FIG. 10).

Figure 11:
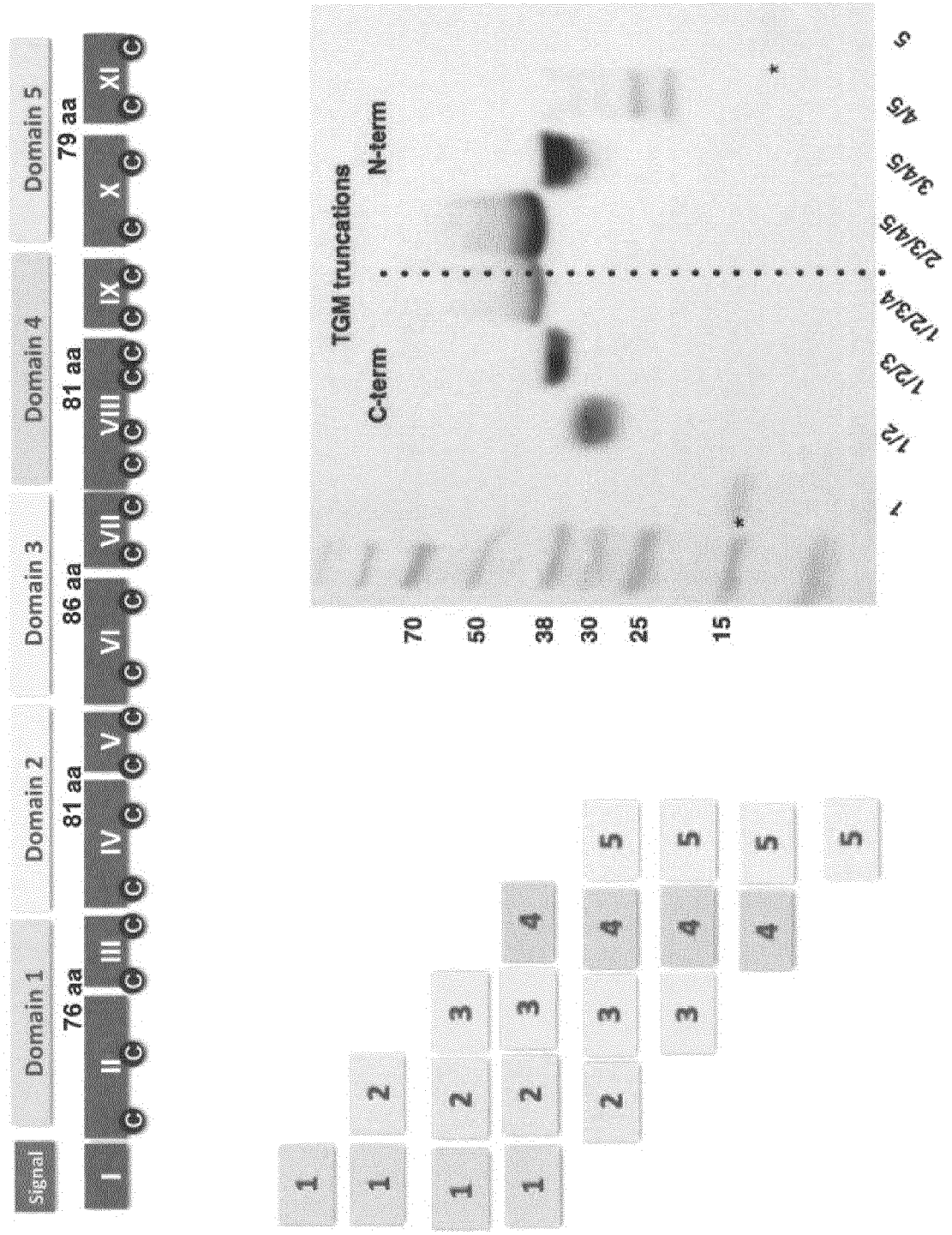
Figure 12:
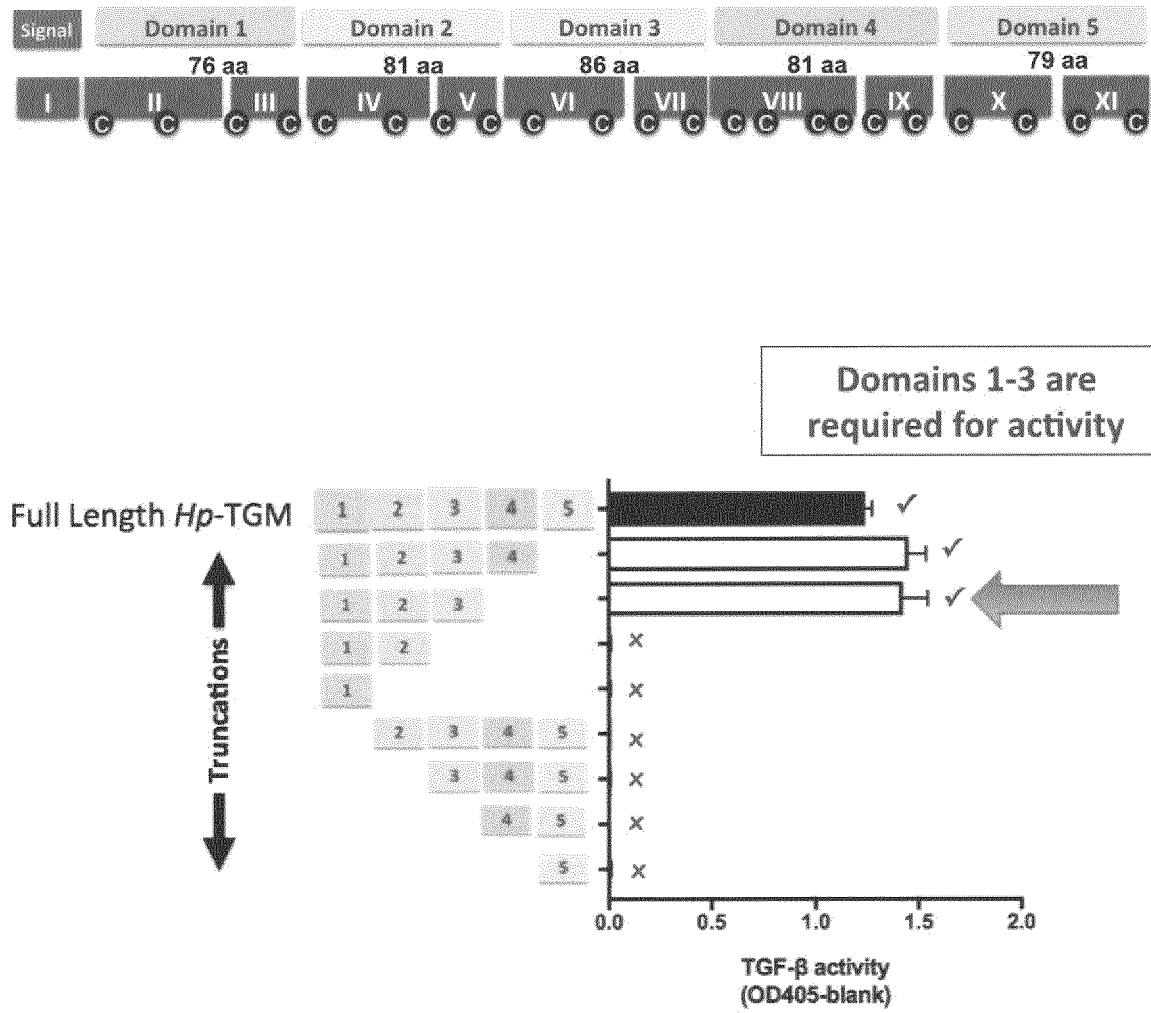

On the strength of these observations, the 5-domain model was tested by expressing a range of truncation constructs as shown in FIG. 11. Each truncated protein was constructed by PCR amplification from the full length coding region DNA, using specific primers, and plasmids containing verified sequence used to transform HEK293T cells for expression. Proteins were purified from HEK293T culture supernatants, and used to test activity in the MFB-F11 reporter cell assay. As shown in FIG. 12, the minimal effective structure was found to be Domains 1-3, with Domains 4 and 5 found not to be necessary, and the absence of either domain 1 or 3 abolishing biological activity.

DISCUSSION

Helminth parasites are known to exploit the immunoregulatory power of the TGF-β pathway, driving the production of this cytokine by host cells, and promoting longer-term establishment of the parasite in mammalian tissues. Many pathogens, particularly viruses, imitate host cytokines, or even express cytokine genes originally captured from the genome of their host[37]. However, no previous example has been reported of a completely unrelated structural product elaborated by parasites that so closely mimics the activity of a crucial host cytokine. Furthermore, the imitation of TGF-β is itself striking, as this mediator is the single most immune suppressive and pro-tolerogenic product of the host immune system involved in a suite of critical immunoregulatory pathways[38]. The ability of TGF-β to induce and expand suppressive Treg cells is arguably the most prominent immunological function of TGF-β[12, 39, 40], while Treg have been shown to be essential for the survival of several helminth parasites in vivo[4, 5] including H. polygyrus[10].

As metazoa, helminth organisms also encode endogenous members of the TGF-β ligand and receptor families, which in some settings can interact with cognate partners of vertebrate origin[41-44]. Further, the inventors had reported that immunomodulatory Treg were induced by H. polygyrus secreted products acting through the TGF-β pathway[9]. The present invention now identifies the molecular agent responsible, and shows that rather than belonging to the classical TGF-β family, the parasite molecule represents an unexpected and novel structure. This finding emphasizes the remarkable immunomodulatory strategy of H. polygyrus, which has convergently evolved a unique structure able to signal through the TGF-β pathway and, like TGF-β itself, induce potently suppressive Treg and abate inflammation in vivo.

Despite signalling through the TGF-β receptors, TβRI and TβRII, and driving Smad phosphorylation, TGM is structurally distinct from the TGF-β molecule. TGM shares no sequence homology with TGF-β, is almost twice the size of a TGF-β homodimer (49 kDa vs. 24 kDa), and is not recognised by pan-vertebrate anti-TGF-β antibodies. Furthermore, TGM is constitutively active, in contrast to the TGF-β ligands which are processed from a longer pre-protein to a mature ~110-amino acid growth factor domain by proteolytic cleavage at a conserved furin site (RRXR)[45].

TGM is a member of the CCP superfamily defined by a 60-80 amino acid (aa) domain with 4 cysteines and key characteristic residues including a conserved tryptophan. In most eukaryotic species, including nematodes, the protein family has expanded and radiated with extensive diversity of structure and function. Interestingly, searching the genomes of the human hookworms Necator americanus[46] and Ancylostoma duodenale reveals 12-18 members of this gene superfamily, each with low levels of sequence similarity to TGM. It remains to be determined if one or more of these homologues may share the cytokine-like activity of TGM.

A notable finding has been that TGM stimulates greater expression of Foxp3 compared to that achieved with TGF-β in both murine and human CD4+ T cells. Intensity of Foxp3 expression by Treg has previously been shown to directly correlate with suppressive ability[47] while high concentrations of TGF-β favour Treg over Th17 differentiation[48]. It may be that TGM is able to deliver a stronger signal through the canonical TGF-β receptor cascade, or it may be inured to inhibitory pathways that naturally counteract signals from the mammalian ligand such as the pseudoreceptor BAMBI[49].

Within the inducible Treg compartment, expression of Foxp3 and consequent regulatory function is in some settings reversible[50, 51]. As it is possible that TGM drives a more stable and longer-lasting Treg phenotype, and/or one less influenced by inflammatory cytokines such as IL-6, it means new therapies such as autologous transfusion following ex vivo expansion of Treg[52] may be much enhanced in terms of both efficacy and safety.

The ability of TGM to delay allograft rejection, and to inhibit all three major subsets of effector CD4+ T cells in vivo, indicates the important therapeutic application of this new molecule. Recombinant TGM offers several advantages including scalable production, a definable mechanism of action and the opportunity for modification to reduce immunogenicity and optimise pharmacokinetic characteristics for pharmacological use. Furthermore, combinations of TGM with currently available immunomodulatory agents will enrich future therapeutic strategies in which the directed manipulation of the different T cell subsets will offer resolution of inflammatory conditions of diverse aetiologies.

TABLE 1

| TGM | |
|---|---|
| Assembly | Hp_I03161_IG00349_L1408 |
| Nucleotide sequence | ACAACCGCATTTATTTCATTCCGCGCTCAGAAAATATCCTTCATAGTGTGCGAATTCCGTCCTTTGTG CACCGATGTACAGTTTTAGTTCCGGGTTCATGCCATTCGCCGTTAGAGCACTCCAGCCGCACCGTTTT ACCTCCACATTCTGCAATCACTTTTGAGCCGGTTGCGTAGAACCTGGCGAAGTCGTCCTTATAACTAT CACTGCCTTCTCCTTTCCTAACAATAACCTTTTCGAAACCAAGTTTATCAAACAAGTCGTCTGAGCTA CAACCTCTTGCGTTAATGCATTCCATAAGCGCAGTAAAATTCCACGTGGCGCCAATGCATTCTCCGA AAATCGGCCCTCCAGTGGAACATGTATACGGCCACTTGCTGCAAACCTTTTTGACGCAGGTGTGTTC AGGGTACTTTCCACTCTTGCCTACTTTCGCGGGTGGGCCTTTCTTTTTGTCTGTCTCGTTGGTCATGGT GAAGTATTCGTAGTGAACAGACTCGTTAGCTTCCAGTGGCTTGCATCTAGGATCTGGGCACTTTCCG ATATTCTTATAGTACTCCCAGTGACTTTCTCCAGTGGTACCACTTTTGTAGCAAATGGCGACAAATTC CCCTGGATCAGCTTCTTGGCTGAGTGCCCTACAACGCCTTCTTGCATGCGTCGGTGAAGGGTAATTT CCAGAACTGTCTTAGTTACTACTGGTCCGACGGTATGTCGGTCGCCAGCGTATCCGTAGTATTCGT AGAAGACAATTCCATCGTCTGGCAGCGGTGGGCAACCACTGGCTGGGCATGTTGGTGTGCTGGAAA ATTGCCACTCAGCATTGTAGCACATACCGATAATATGACCTTGAACATTGCTGTCTGTAGGAAAGTTT TTGCAGATTCTTTTAATGTATGTTAGTTCAGGATATTTTCCAGAGGCATCTGGATGGACCGTTATATTA AAAATGATTCCTGGATTTACAGTGGCTTTAAGATACTCGAAGCTGACAGTATCGTTAGTCGGCAACG GCGAGCACCTACGATCATCGCATTCTTGTACTCCTTCATAGTAGTACCATTGTGATGCAAGGCAGAT GCCAACGAACCAACCTGTCGTGTCTTCTCCATGCAATCCTTTACAGAACCGTTTAACATGTGTATAAT CAGGATACATTCCAGAATTGTCGATTTGCGCAGGAATTTCTATGTTCTTAGGACCTTTTGCAACGTAT TTGTAGGTGGCAGCTTCATCAGAAAACGGCATGCAGCCGCTGTCATCTGTAGCTGCAACCTCGAGT AGGCCAATCACTACTGTCAGCAGCATTTCAATGTTTTACTAGGAGCAGTTCCATAGGACTTGGCTGA TACAACTCCTGACGGAAGAACTGACCGAAAATCACTCACGCTAACGATAAAGGACCCC |
| Nucleotide ORF | ATGCTGCTGACAGTAGTGATTGGCCTACTCGAGGTTGCAGCTACAGATGACAGCGGCTGCATGCCG TTTTCTGATGAAGCTGCCACCTACAAATACGTTGCAAAAGGTCCTAAGAACATAGAAATTCCTGCGC AAATCGACAATTCTGGAATGTATCCTGATTATACACATGTTAAACGGTTCTGTAAAGGATTGCATGG AGAAGACACGACAGGTTGGTTCGTTGGCATCTGCCTTGCATCACAATGGTACTACTATGAAGGAGT |

TABLE 1-continued

|  |  |
|---|---|
|  | ACAAGAATGCGATGATCGTAGGTGCTCGCCGTTGCCGACTAACGATACTGTCAGCTTCGAGTATCTT<br>AAAGCCACTGTAAATCCAGGAATCATTTTTAATATAACGGTCCATCCAGATGCCTCTGGAAAATATC<br>CTGAACTAACATACATTAAAAGAATCTGCAAAAACTTTCCTACAGACAGCAATGTTCAAGGTCATAT<br>TATCGGTATGTGCTACAATGCTGAGTGGCAATTTTCCAGCACACCAACATGCCCAGCCAGTGGTTGC<br>CCACCGCTGCCAGACGATGGAATTGTCTTCTACGAATACTACGGATACGCTGGCGACCGACATACC<br>GTCGGACCAGTAGTAACTAAGGACAGTTCTGGAAATTACCCTTCACCGACGCATGCAAGAAGGCGT<br>TGTAGGGCACTCAGCCAAGAAGCTGATCCAGGGGAATTTGTCGCCATTTGCTACAAAAGTGGTACC<br>ACTGGAGAAAGTCACTGGGAGTACTATAAGAATATCGGAAAGTGCCCAGATCCTAGATGCAAGCCA<br>CTGAAGCTAACGAGTCTGTTCACTACGAATACTTCACCATGACCAACGAGACAGACAAAAAGAAA<br>GGCCCACCCGCGAAAGTAGGCAAGAGTGGAAAGTACCCTGAACACACCTGCGTCAAAAAGGTTTG<br>CAGCAAGTGGCCGTATACATGTTCCACTGGAGGGCCGATTTTCGGAGAATGCATTGGCGCCACGTG<br>GAATTTTACTGCGCTTATGGAATGCATTAACGCAAGAGGTTGTAGCTCAGACGACTTGTTTGATAAA<br>CTTGGTTTCGAAAAGGTTATTGTTAGGAAAGGAGAAGGCAGTGATAGTTATAAGGACGACTTCGCC<br>AGGTTCTACGCAACCGGCTCAAAAGTGATTGCAGAATGTGGAGGTAAACGGTGCGGCTGGAGTG<br>CTCTAACGGCGAATGGCATGAACCCGGAACTAAAACTGTACATCGGTGCACAAAGGACGGAATTCG<br>CACACTATGA |
| Amino acid<br>Sequence | MLLTVVIGLLEVAATDDSGCMPFSDEAATYKYVAKGPKNIEIPAQIDNSGMYPDYTHVKRFCKGLHGEDT<br>TGWFVGICLASQWYYYEGVQECDDRRCSPLPTNDTVSFEYLKATVNPGIIFNITVHPDASGKYPELTYIKRI<br>CKNFPTDSNVQGHIIGMCYNAEWQFSSTPTCPASGCPPLPDDGIVFYEYYGYAGDRHTVGPVVTKDSSG<br>NYPSPTHARRRCRALSQEADPGEFVAICYKSGTTGESHWEYYKNIGKCPDPRCKPLEANESVHYEYFTMT<br>NETDKKKGPPAKVGKSGKYPEHTCVKKVCSKWPYTCSTGGPIFGECIGATWNFTALMECINARGCSSDD<br>LFDKLGFEKVIVRKGEGSDSYKDDFARFYATGSKVIAECGGKTVRLECSNGEWHEPGTKTVHRCTKDGIRT<br>L* |

TGM-a

|  |  |
|---|---|
| Assembly | Hp_I03162_IG00349_L1408 |
| Nucleotide<br>sequence | ACAACCACATTTATTTCATTCCAAGATAAGAGAATATCCTTCATAGTGCCTAATTCCTTCGCTTGTGC<br>ACCGATGCACAGTTCTTGTTTCCGAATCATGCCATTCGCCGTTAGAGCACTCCAGTCGCACCGTTTTA<br>CCTTTACATTCTGCATTCACTTTCGAACCGGTTGTGTAGAACCTGACGTAGTCGTCTTTATAACTATCG<br>CTGCCTTCTCCTTCCCTAACCATAACTATTTCAAAGCCCAATTTATTAAACAAGTCGCCTCCGTCACA<br>ACCCCTTGCGTTTAAGCATTCGTCAAGTGCAGTAAAATTCCACTGGCCGTCAAGGCATTCTCCGAAA<br>ATCGGCCCTTTAACCGAACATGTATACGGTGACTTGTCGCAAATTTTCTGACACACGTGTGTTGAG<br>AGTATTTTCCACCCTTATCTACTTGCGCGGGCGTGCCTTCCTTTTTGCCTGTCTCGTTGGCCATGGTGA<br>AGTATTCGTAGCGAACAGACTCGTCAGCTTTCAGTGGCTTGCATCTAGGATCTGGGCAATTCTTTATA<br>TACTTATAGTACTGCCAGTGACTTTCTCCAGTGGTACAACTTTTGTAGCAAATGGCGACAAATTCCCC<br>TGTATCAGCTTTTTGGCTGAGTGCCCTACAACGCCTTCTTGCATGCGTCGGTGAAGGGTAATTTCCAG<br>AACTGTCCTTAGTTACTACTGGTCCGACGGTATGTCGGTCGCCAGCGTATCCGTAGTATTCGTAGAA<br>GACAATTCCATCGTCTGGCAGCGGTGGGCAACCACTGGCTGGGCATGTTGGGTGTGCTGGAAAATT<br>GCCACTCAGCATTGTAGCACATACCGATAATATGACCTTGAACATTGCTGTCTGTAGGAAAGTTTTTG<br>CAGATTCTTTTAATGTATGTTAGTTCAGGATATTTTCCAGAGGCATCTGGATGGACCGTTATATTAAA<br>AATGATTCCTGGATTTACAGTGGCTTTAAGATACTCGAAGCTGACAGTATCGTTAGTCGGCAACGGC<br>GAGCACCTACGATCATCGCATTCTTGTACTCCTTCATAGTAGTACCATTGTGATGCAAGGCAGATGC<br>CAACGAACCAACCTGTCGTGTCTTCTCCATGCAATCCTTTACAGAACCGTTTAACATGTGTATAATCA<br>GGATACATTCCAGAATTGTCGATTTGCGCAGGAATTTCTATGTTCTTAGGACCTTTTGCAACGTATTT<br>GTAGGTGGCAGCTTCATCAGAAAACGGCATGCAGCCGCTGTCATCTGTAGCTGCAACCTCGAGTAG<br>GCCAATCACTACTGTCAGCAGCATTTCAATGTTTTACTAGGAGCAGTTCCATAGGACTTGGCTGATA<br>CAACTCCTGACGGAAGAACTGACCGAAAATCACTCACGCTAACGATAAAGGACCCC |
| Nucleotide<br>sequence<br>ORF | ATGCTGCTGACAGTAGTGATTGGCCTACTCGAGGTTGCAGCTACAGATGACAGCGGCTGCATGCCG<br>TTTTCTGATGAAGCTGCCACCTACAAATACGTTGCAAAAGGTCCTAAGAACATAGAAATTCCTGCGC<br>AAATCGACAATTCTGGAATGTATCCTGATTATACACATGTTAAACGGTTCTGTAAAGGATTGCATGG<br>AGAAGACACGACAGGTTGGTTCGTTGGCATCTGCCTTGCATCACAATGGTACTACTATGAAGGAGT<br>ACAAGAATGCGATGATCGTAGGTGCTCGCCGTTGCCGACTAACGATACTGTCAGCTTCGAGTATCTT<br>AAAGCCACTGTAAATCCAGGAATCATTTTTAATATAACGGTCCATCCAGATGCCTCTGGAAAATATC<br>CTGAACTAACATACATTAAAAGAATCTGCAAAAACTTTCCTACAGACAGCAATGTTCAAGGTCATAT<br>TATCGGTATGTGCTACAATGCTGAGTGGCAATTTTCCAGCACACCAACATGCCCAGCCAGTGGTTG<br>CCCACCGCTGCCAGACGATGGAATTGTCTTCTACGAATACTACGGATACGCTGGCGACCGACATAC<br>CGTCGGACCAGTAGTAACTAAGGACAGTTCTGGAAATTACCCTTCACCGACGCATGCAAGAAGGCG<br>TTGTAGGGCACTCAGCCAAAAGCTGATACAGGGGAATTTGTCGCCATTTGCTACAAAAGTTGTACC<br>ACTGGAGAAAGTCACTGGCAGTACTATAAGTATATAAAGAATTGCCCAGATCCTAGATGCAAGCCA<br>CTGAAAGCTGACGAGTCTGTTCGCTACGAATACTTCACCATGGCCAACGAGACAGGCAAAAAGGAA<br>GGCACGCCCGCGAAGTAGATAAGGGTGGAAAATACTCTCAACACACGTGTGTCAGAAAATTTTGC<br>GACAAGTCACCGTATACATGTTCGGTTAAAGGGCCGATTTTCGGAGAATGCCTTGACGGCCAGTGG<br>AATTTTACTGCACTTGACGAATGCTTAAACGCAAGGGGTTGTGACGGAGGCGACTTGTTTAATAAAT<br>TGGGCTTTGAAATAGTTATGGTTAGGGAAGGAGAAGGCAGCGATAGTTATAAAGACGACTACGTCA<br>GGTTCTACACAACCGGTTCGAAAGTGAATGCAGAATGTAAAGGTAAAACGGTGCGACTGGAGTGCT<br>CTAACGGCGAATGGCATGATTCGGAAACAAGAACTGTGCATCGGTGCACAAGCGAAGGAATTAGG<br>CACTATGAAGGATATTCTCTTATCTTGGAATGA |

TABLE 1-continued

| | |
|---|---|
| Amino acid sequence | MLLTVVIGLLEVAATDDSGCMPFSDEAATYKYVAKGPKNIEIPAQIDNSGMYPDYTHVKRFCKGLHGEDT
TGWFVGICLASQWYYYEGVQECDDRRCSPLPTNDTVSFEYLKATVNPGIIFNITVHPDASGKYPELTYIKRI
CKNFPTDSNVQGHIIGMCYNAEWQFSSTPTCPASGCPPLPDDGIVFYEYYGYAGDRHTVGPVVTKDSSG
NYPSPTHARRRCRALSQKADTGEFVAICYKSCTTGESHWQYYKYIKNCPDPRCKPLKADESVRYEYFTMA
NETGKKEGTPAQVDKGGKYSQHTCVRKFCDKSPYTCSVKGPIFGECLDGQWNFTALDECLNARGCDGG
DLFNKLGFEIVMVREGEGSDSYKDDYVRFYTTGSKVNAECKGKTVRLECSNGEWHDSETRTVHRCTSEGI
RHYEGYSLILE* |
| Comments | identical N-terminal domains (1-228), 49 changes 229-422, 8 additional aa |

TGM-b

| | |
|---|---|
| Assembly | Hp_I03163_IG00349_L1163 |
| Nucleotide Sequence | AACCACATTTATTTCACTCCAAGATGAGAAAATATTCTTCATGGTGCGCGAAGTCCTTCCTTTGTGCA
CCGGTGCACAGTTTTAGTTCCGGGATCATGCCATTCACCGTTAGAGCACTCCAGCCGCACCGTGTTA
CCTTTACATTCGGCATTCACTTTCGAACCGGTTGCGTAGAACCGGGCAAAGTCGTCCTTATAACTATC
ACTGCCTTCTTCTTCTCTAACCATAACTCCTTCAAAGCCCAGTTTATCAAACAAGTCGTCACTGTTACA
ACCCCTAGGATCTGGGCACTTCCTTATATGACTGTAGTAATCCCAATGACTTTCGCCAGTGGTACCA
CATCTGTAGCAAATGCCAACAAATTCCCCTGGATCAGCTTTTTGGCTGAGTGCCCTACAACGCCTTCT
TGCATGCGTCGGTGAAGGGTAATTTCCAGAACTGTCCTTAGTTACTGCTGGTCCGACGGTATGTCGA
TCGCCAGCGTATCCGTAGTATTCGTGGAAGACGATTCCATCGTCTGGCAGCGGTGGGCAACCAATT
GAAGGGCTTGTTGGTGTGCTGGAAAACCGCCATTCAGCATTGTAGCACATGCCGATAATATGACCTT
GAACTTTGCTGTCAGTAGGAAAATTTTTGCAGATTCTTTTAATGTATGTTAGTTCAGGATATTTTCCAG
TGGCATCTGGATGGACCGTTATATTAAAAATGATTCCTGGATTTACAGTGGCTTTAAGATACTCGAA
GGTGACAGTATCGTCCGTCGACAACGGCAAGCACCCACGACCTCCGCATTCTTGTACTCCTTGATAG
TAGACCCATTCTGATCCAGGGCCTATGCCAACGAACCAACCTGTCGTGTCTTCTCCATGCAATCCTTT
ACAAAACCGTTTAACATGTGTATAATCAGGATACATTCCAGAATTGTCGATTTGCGCAGGAATTTCTA
TGTTCTTAGGACCTTTTGCAACGTATTTGTAGGTGGCAGCTTCATCAGAAAACGGCATGCAGCCGCT
GTCATCTGTAGCTGCAACCTCGAGTAGGCCAATCACTACTGTCAGCAGCATTTCAATGTTTTACTAG
GAGCAGTTCCATAGGACTTGGCTGATACAACTCCTGACGGAAGAACTGACCGAAAATCACTCACGC
TAACGATAAAGGACCCC |
| Nucleotide Sequence ORF | ATGCTGCTGACAGTAGTGATTGGCCTACTCGAGGTTGCAGCTACAGATGACAGCGGCTGCATGCCG
TTTTCTGATGAAGCTGCCACCTACAAATACGTTGCAAAAGGTCCTAAGAACATAGAAATTCCTGCGC
AAATCGACAATTCTGGAATGTATCCTGATTATACACATGTTAAACGGTTTTGTAAAGGATTGCATGGA
GAAGACACGGACAGGTTGGTTCGTTGGCATAGGCCCTGGATCAGAATGGGTCTACTATCAAGGAGTA
CAAGAATGCGGAGGTCGTGGGTGCTTGCCGTTGTCGACGGACGATACTGTCACCTTCGAGTATCTTA
AAGCCACTGTAAATCCAGGAATCATTTTTAATATAACGGTCCATCCAGATGCCACTGGAAAATATCC
TGAACTAACATACATTAAAAGAATCTGCAAAAATTTTCCTACTGACAGCAAAGTTCAAGGTCATATT
ATCGGCATGTGCTACAATGCTAATGGCGGTTTTCCAGCACACCAACAAGCCCTTCAATTGGTTGCC
CACCGCTGCCAGACGATGGAATCGTCTTCCACGAATACTACGGATACGCTGGCGATCGACATACCG
TCGGACCAGCAGTAACTAAGGACAGTTCTGGAAATTACCCTTCACCGACGCATGCAAGAAGGCGTT
GTAGGGCACTCAGCCAAAAGCTGATCCAGGGGAATTTGTTGGCATTTGCTACAGATGTGGTACCA
CTGGCGAAAGTCATTGGGATTACTACAGTCATATAAGGAAGTGCCCAGATCCTAGGGGTTGTAACA
GTGACGACTTGTTTGATAAACTGGGCTTTGAAGGAGTTATGGTTAGAGAAGAAGAAGGCAGTGATA
GTTATAAGGACGACTTTGCCCGGTTCTACGCAACCGGTTCGAAAGTGAATGCCGAATGTAAAGGTA
ACACGGTGCGGCTGGAGTGCTCTAACGGTGAATGGCATGATCCCGGAACTAAAACTGTGCACCGGT
GCACAAAGGAAGGACTTCGCGCACCATGA |
| Amino acid Sequence | MLLTVVIGLLEVAATDDSGCMPFSDEAATYKYVAKGPKNIEIPAQIDNSGMYPDYTHVKRFCKGLHGEDT
TGWFVGIGPGSEWVYYQGVQECGGRGCLPLSTDDTVTFEYLKATVNPGIIFNITVHPDATGKYPELTYIKRI
CKNFPTDSKVQGHIIGMCYNAEWRFSSTPTSPSIGCPPLPDDGIVFHEYYGYAGDRHTVGPAVTKDSSG
NYPSPTHARRRCRALSQKADPGEFVGICYRCGTTGESHWDYYSHIRKCPDPRGCNSDDLFDKLGFEGV
MVREEEGSDSYKDDFARFYATGSKVNAECKGNTVRLECSNGEWHDPGTKTVHRCTKEGLRAP* |
| Comments | 21 changes in N terminus (21/228 = 90.8% identity). Missing Cys-79. Missing exons 8 and 9 (aa 263-343); between 343-422, 13 aa changes (85.6% identity) |

TGM-c

| | |
|---|---|
| Assembly | Hp_I18045_IG09989_L856 |
| Nucleotide Sequence | TGGTTTAATTACCCAAGTTTTGAGGGGATCATTGCGGAACTCGACGCTCCACCAAGATGCTATCATT
ATTCATTGCCATCGGATTGCTTGAGGCTGCTGGATCAAGTTGTCCACCGTGGGCGATGCAGCAATT
AAGGACAGTCTCGAAAATTATCCTCCGAATACGCATGCAAGAAGACATTGCAAAGCACTCAGCAAA
AAAGCTGACCCAGGAGAATTTGTCGCCATTTGCTACCAAAGAAGAGGCACTAGTGAAAGTCAATGG
CAGTATTATCCTAGAATAGCATCATGTCCAGACCCTAGGTGCAAGCCTCTCGAAAAAACGATTCTG
TTAGCTATGAATATTTCACAAAACCCACTAAAGGACTGAAGATGGGTTCAATCACAAAGCCGGACA
AAAGTGGAAAGTACCCTGAAGAAACTTTTGTTAAGGAGTATTGCAATGACCTTCCAAGGAACAGCC
TAGCGCAAGGAAAAACCTACGCAGAGTGCTTGGATTCAGAGTGGAAGCTTAAAAATTTGCCAGACT
GTCGATTCGCAGCAGGATGTGACGAAGAATATCTGCTTGAGAAGTTAATGTTCGTTGATATTTCGTA
CTGGGGAAAAGATGCAGCGAAATTTCCGATGACAAAACATATAGGTATTATCGGCCCGGTTCGAA
AGTTACTGCGAAGTGCAAAGGTAAATCTGTGAAGTTAACATGTGTTGACGGCGGCTACTGGGTTAC
AGTGGACGGCAGAAAGGCGCTCTGCACATGAGCGGTCCTCACAGTTGAAGTGCAATAAATATTTT
CGCTACCAGATGATGAAACTGTCTGGTACGAATACTACGGATACGTTGACGGTCGACATA |

TABLE 1-continued

| | |
|---|---|
| Nucleotide Sequence ORF | ATGCTATCATTATTCATTGCCATCGGATTGCTTGAGGCTGCTGGATCAAGTTGTCCACCGCTACCAGA<br>TGATGAAACTGTCTGGTACGAATACTACGGATACGTTGACGGTCGACATACCGTGGGCGATGCAGC<br>AATTAAGGACAGTCTCGAAAATTATCCTCCGAATACGCATGCAAGAAGACATTGCAAAGCACTCAG<br>CAAAAAAGCTGACCCAGGAGAATTTGTCGCCATTTGCTACCAAAGAAGAGGCACTAGTGAAAGTCA<br>ATGGCAGTATTATCCTAGAATAGCATCATGTCCAGACCCTAGGTGCAAGCCTCTCGAAAAAAACGAT<br>TCTGTTAGCTATGAATATTTCACAAAACCCACTAAAGGACTGAAGATGGGTTCAATCACAAAGCCGG<br>ACAAAAGTGGAAAGTACCCTGAAGAAACTTTTGTTAGAAGGTATTGCAATGACCTTCCAAGGAACA<br>GCCTAGCGCAAGGAAAAACCTACGCAGAGTGCTTGGATTCAGAGTGGAAGCTTAAAAATTTGCCAG<br>ACTGTCGATTCGCAGCAGGATGTGACGAAGAATATCTGCTTGAGAAGTTAATGTTCGTTGATATTTC<br>GTACTGGGGAAAAGATGCAGCGAAATTTTCCGATGACAAAACATATAGGTATTATCGGCCCGGTTC<br>GAAAGTTACTGCGAAGTGCAAAGGTAAATCTGTGAAGTTAACATGTTGACGGCGGCTACTGGGT<br>TACAGTGGACGGCAGAAAGGCGCTCTGCACATGA |
| Amino acid Sequence | MLSLFIAIGLLEAAGSSCPPLPDDETVWYEYYGYVDGRHTVGDAAIKDSLENYPPNTHARRHCKALSKKA<br>DPGEFVAICYQRRGTSESQWQYYPRIASCPDPRCKPLEKNDSVSYEYFTKPTKGLKMGSITKPDKSGKYPE<br>ETFVRRYCNDLPRNSLAQGKTYAECLDSEWKLKNLPDCRFAAGCDEEYLLEKLMFVDISYWGKDAAKFS<br>DDKTYRYYRPGSKVTAKCKGKSVKLTCVDGGYWVTVDGRKALCT |
| Comments | Missing exons 2, 3, 4 and 5. Only 254 aa, over which shows 117 (46.0%) identity |

TGM-d

| | |
|---|---|
| Assembly | Hp_I03160_IG00349_L1402 |
| Nucleotide Sequence | AACCACATTTATTTCACTCCAAGATGAGAAAATATTCTTCATGGTGCGCGAAGTCCTTCCTTTGTGCA<br>CGATGCACAGTTTTAGCTCCCAAATCATGCCATTCGCCGTTAGAGCACTCCAGCCGCGCCGTTTCAC<br>CTCGACATTGTGCACTGACTTTAGAACCGGTTGCGTAGAACAAGACGTAGGCGTCCCTATAACTATC<br>ACTGAATTCTCCTTCCCTAACCATTATTTCTTTGAAGCCCAGCTCAAACAAGTCGTTTTCGTCACAAC<br>CTCTTGCGTTAATGCATTCCATAAGCGCAGTAAAATTCCACGTGGCGCCAATGCATTCTCCGAAAAT<br>CGGCCCTCCAGCGGAACATGTATACGGCCACTTGCTGCAAACCTTTTTGACGCAGGTGTGTTCAGG<br>GTACTTTCCACTCTTGCCTACTTTCGCGGGTGGGCCTTTCTTTTTGTCTGTCTCGTTGGTCATGGTGAA<br>GTATTCGTAGTAACAGACTCGTTAGCTTCCAGTGGCTTGCATCTAGGATCTGGGCACTTTCCGATAT<br>TCTTTATAGTACTCCCAGTGACTTTCTCCAGTGGTACCACTTTTGTAGCAAATGGCGACAAATTCCCCT<br>GGATCAGCTTCTTGGCTGAGTGCCCTACAACGCCTTCTTGCATGCGTCGGTGAAGGGTAATTTCCAG<br>AACTGTCCTTAGTTACTACTGGTCCGACGGTATGTCGGTCGCCAGCGTATCCGTAGTATTCGTAGAA<br>GACAATTCCATCGTCTGGCAGCGGTGGGCAACCACTGGCTGGGCATGTTGGTGTGCTGGAAAATTG<br>CCACTCAGCATTGTAGCACATACCGATAATATGACCTTGAACATTGCTGTCTGTAGGAAAGTTTTTGC<br>AGATTCTTTTAATGTATGTTAGTTCAGGATATTTTCCAGAGGCATCTGGATGGACCGTTATATTAAAA<br>ATGATTCCTGGATTTACAGTGGCTTTAAGATACTGCAAGCTGACATATCGTTAGTCGGCAACGGCG<br>AGCACCTACGATCATCGCATTCTTGTACTCCTTCATAGTAGTACCATTGTGATGCAAGGCAGATGCC<br>AACGAACCAACCTGTCGTGTCTTCTCCATGCAATCCTTTACAGAACCGTTTAACATGTGTATAATCAG<br>GATACATTCCAGAATTGTCGATTTGCGCAGGAATTTCTATGTTCTTAGGACCTTTTGCAACGTATTTGT<br>AGGTGGCAGCTTCATCAGAAAACGGCATGCAGCCGCTGTCATCTGTAGCTGCAACCTCGAGTAGGC<br>CAATCACTACTGTCAGCAGCATTTCAATGTTTTACTAGGAGCAGTTCCATAGGACTTGGCTGATACA<br>ACTCCTGACGAAGAACTGACCGAAAATCACTCACGCTAACGATAAAGGACCCC |
| Nucleotide Sequence ORF | ATGCTGCTGACAGTAGTGATTGGCCTACTCGAGGTTGCAGCTACAGATGACAGCGGCTGCATGCCG<br>TTTTCTGATGAAGCTGCCACCTACAAATACGTTGCAAAAGGTCCTAAGAACATAGAAATTCCTGCGC<br>AAATCGACAATTCTGGAATGTATCCTGATTATACACATGTTCACGGTTCTGTAAAGGATTGCATGG<br>AGAAGACACGACAGGTTGGTTCGTTGGCATCTGCCTTGCATCACAATGGTACTACTATGAAGGAGT<br>ACAAGAATGCGATGATCGTAGGTGCTCGCCGTTGCCGACTAACGATACTGTCAGCTTCGAGTATCTT<br>AAAGCCACTGTAAATCCAGGAATCATTTTTAATATAACGGTCCATCCAGATGCCTCTGGAAAATATC<br>CTGAACTAACATACATTAAAAGAATCTGCAAAAACTTTCCTACAGACAGCAATGTTCAAGGTCATAT<br>TATCGGTATGTGCTACAATGCTGAGTGGCAATTTTCCAGCACACCAACATGCCCAGCCAGTGGTTGC<br>CCACCGCTGCCAGACGATGGAATTGTCTTCTACGAATACTGCTGGCGACCGACATACC<br>GTCGGACCAGTAGTAACTAAGGACAGTTCTGGAAATTACCCTTCACCGACGCATGCAAGAAGGCGT<br>TGTAGGGCACTCAGCCAAGAAGCTGATCCAGGGGAATTTGTCGCCATTTGCTACAAAAGTGGTACC<br>ACTGGAGAAAGTCACTGGGAGTACTATAAGAATATCGGAAAGTGCCCAGATCCTAGATGCAAGCCA<br>CTGGAAGCTAACGAGTCTGTTCACTACGAATACTTCACCATGACCAACGAGACAGACAAAAAGAAA<br>GGCCCACCCGCGAAAGTAGGCAAGAGTGGAAAGTACCCTGAACACACCTGCGTCAAAAAGGTTTG<br>CAGCAAGTGGCCGTATACATGTTCCGCTGGAGGGCCGATTTTCGGAGAATGCATTGGCGCCACGTG<br>GAATTTTACTGCGCTTATGGAATGCATTAACGCAAGAGGTTGTGACGAAAACGACTTGTTTGAGCTG<br>GGCTTCAAAGAAATAATGGTTAGGGAAGGAGAATTCAGTGATAGTTATAGGGACGCCTACGTCTTG<br>TTCTACGCAACCGGTTCTAAAGTCAGTGCACAATGTCGAGGTGAAACGGCGCGGCTGGAGTGCTCT<br>AACGGCGAATGGCATGATTTGGGAGCTAAAACTGTGCATCGTGCACAAAGGAAGGACTTCGCGCA<br>CCATGAAGAATATTTTCTCATCTTGGAGTGA |
| Amino acid Sequence | MLLTVVIGLLEVAATDDSGCMPFSDEAATYKYVAKGPKNIEIPAQIDNSGMYPDYTHVKRFCKGLHGEDT<br>TGWFVGICLASQWYYYEGVQECDDRRCSPLPTNDTVSFEYLKATVNPGIIFNITVHPDASGKYPELTYIKRI<br>CKNFPTDSNVQGHIIGMCYNAEWQFSSTPTCPASGCPPLPDDGIVFYEYYGYAGDRHTVGPVVTKDSSG<br>NYPSPTHARRRCRALSQEADPGEFVAICYKSGTTGESHWEYYKNIGKCPDPRCKPLEANESVHYEYFTMT<br>NETDKKKGPPAKVGKSGKYPEHTCVKKVCSKWPYTCSAGGPIFGECIGATWNFTALMECINARGCDEND<br>LFELGFKEIMVREGEFSDSYRDAYVLFYATGSKVSAQCRGETARLECSNGEWHDLGAKTVHRAQRKDFA<br>HHEEYFLILE* |
| Comments | identical 1-318; 34 changes 319-422 (67.3% identity), 8 additional aa |

TABLE 1-continued

TGM-e

| | |
|---|---|
| Nucleotide Sequence | ACAACCACATTTATTTCATTCCAAGCTGATGAAATATCCTTCATAGTGCGCGGATTCCTTCC<br>TTTGTGCACCGATGCACAGTTTTAGTTCCGGGATCATGCCATTCACCGTCAGAGCACTCCAGCTGCA<br>CCGTTTTACCTTTACATTCCGCATTCACTTTCGAACCGGTTGCGTAGAACCTGACGAAGTCGTCCTTA<br>TAACTATCACTGCCTTCTTCTTCTAACCATAACTCCTTCAAAGCCCAGTTTATCAAACAAGTCGTCA<br>CTGTTGCAACCCCTTGCGTTTAAGCATTCGTCAAGTGCAGTAAAATTCCACTGGCCGTCAAGGCATT<br>CTCCGAAAATCGGCCCTTTAACCGAACATGTATACGGTGACTTGTCGCAAAATTTTCTGACACACGT<br>GTGTTGAGGGTACTTTCCACCCTTGTCTACTTCCGCGGGCGTGCCTTCCTTTCTGCCCGTCTCGTTGG<br>TCATGGTGAAGTATTCGTAGTGAACAGACACGTTAGTTTCCAGTGGCTTGCATCTAGGATCTGGGCA<br>TTTCCTTATATGACTGTAGTAATCCCAATGACTTTCGCCAGTCGTACCGCTTTTGTAGCAAATGCCAA<br>CAAATTCTCCTGGATCAGCTTTTTGGCTGAGTGCCCTACAACGCCTTCTTGCATGCGTTTGTGGAGGG<br>TAATTTCCAGAACTGTCCTTAGATACTGCTCGTCCGACGGTATGTCGATTGCCAGCGTATCCGTAGTA<br>TTCGTAGAAGACAATTCCATCATCTGGTAGCGGTGGGCAACCACTGGGTGGGCATGTTGGTGTGCT<br>AGAAAACCGCCATTCAGCATTGTAGCACATGCCGATAATATGGCCTTGAACTTTGCTGTCAGCAGGA<br>AAATTTTTGCAGATTCTTTTAATGTATGTTAGTTCAGGATATTTTCCAGAAGCATCTGGATGAACCGTT<br>ATATTAAAATTGATTCCTGCATTTACTGTGGCTTTAAGATACTCGTAGGTGACAGTATCGTTCGTCGG<br>CAACGGCGAGCACCTACGGTCTTGGCATTCTTGTACTCCTTGATAGTAGACCCATTCTGATCCAAGG<br>CAAATGCCGACGTACCTACCTGTCTTTTCTTCTCCATGCAATCCTTTACAAAACCGTTTAACATGTGTA<br>TGATCAGGATACGCTCCAGAGCTGTCATTTTGTGCAGGAGTTTCGTCGTTTCTAGAACGTTCTGTTAA<br>ATATTTTATAGGAGGCGGTTTCATCAGAAAATGGCATACAGCCGTCGGCGTCTGTAGCTGCAACCTCG<br>AGTAGGCCAATTAATACAATCAGCAGCATTTCATCACGCTAACGATAAAGGGCCGTTCC |
| Nucleotide Sequence ORF | ATGCTGCTGATTGTATTAATTGGCCTACTCGAGGTTGCAGCTACAGACGCCAGCGGCTGTATGCCAT<br>TTTCTGATGAAACCGCCTCCTATAAATATTTAACAGAACGTTCTAGAAACGACGAAACTCCTGCACA<br>AAATGACAGCTCTGGAGCGTATCCTGATCATACACATGTTAAACGGTTTTGTAAAGGATTGCATGGA<br>GAAGAAAAGACAGGTAGGTACGTCGGCATTTGCCTTGGATCAGAATGGGTCTACTATCAAGGAGTA<br>CAAGAATGCCAAGACCGTAGGTGCTCGCCGTTGCCGACGAACGATACTGTCACCTACGAGTATCTT<br>AAAGCCACAGTAAATGCAGGAATCAATTTTAATATAACGGTTCATCCAGATGCTTCTGGAAAATATC<br>CTGAACTAACATACATTAAAGAATCTGCAAAAATTTTCCTGCTGACAGCAAAGTTCAAGGCCATAT<br>TATCGGCATGTGCTACAATGCTGAATGGCGGTTTTCTAGCACACCAACATGCCCACCCAGTGGTTGC<br>CCACCGCTACCAGATGATGGAATTGTCTTCTACGAATACTACGGATCACGCTGGCAATCGACATACCG<br>TCGGACGAGCAGTATCTAAGGACAGTTCTGGAAATTACCCTCCACAAACGCATGCAAGAAGGCGTT<br>GTAGGGCACTCAGCCAAAAAGCTGATCCAGGAGAATTTGTTGGCATTTGCTACAAAAGCGGTACGA<br>CTGGCGAAAGTCATTGGGATTACTACAGTCATATAAGGAAATGCCCAGATCCTAGATGCAAGCCAC<br>TGGAAACTAACGTGTCTGTTCACTACGAATACTTCACCATGACCAACGAGACGGGCAGAAAGGAAG<br>GCACGCCCGCGGAAGTAGACAAGGGTGGAAAGTACCCTCAACACACGTGTGTCAGAAAATTTTGC<br>GACAAGTCACCGTATACATGTTCGGTTAAAGGGCCGATTTTCGGAGAATGCCTTGACGGCCAGTGG<br>AATTTTACTGCACTTGACGAATGCTTAAACGCAAGGGGTTGCAACAGTGACGACTTGTTGATAAAC<br>TGGGCTTTGAAGGAGTTATGGTTAGAGAAGAAGAAGGCAGTGATAGTTATAAGGACGACTTCGTCA<br>GGTTCTACGCAACCGGTTCGAAAGTGAATGCGGAATGTAAAGGTAAAACGGTGCAGCTGGAGTGCT<br>CTGACGGTGAATGGCATGATCCCGGAACTAAAACTGTGCATCGGTGCACAAAGGAAGGAATCCGC<br>GCACTATGA |
| Amino acid Sequence | MLLIVLIGLLEVAATDASGCMPFSDETASYKYLTERSRNDETPAQNDSSGAYPDHTHVKRFCKGLHGEEK<br>TGRYVGICLGSEWVYYQGVQECQDRRCSPLPTNDTVTYEYLKATVNAGINFNITVHPDASGKYPELTYIK<br>RICKNFPADSKVQGHIIGMCYNAEWRFSSTPTCPPSGCPPLPDDGIVFYEYYGYAGNRHTVGRAVSKDSS<br>GNYPPQTHARRRCRALSQKADPGEFVGICYKSGTTGESHWDYYSHIRKCPDPRCKPLETNVSVHYEYFT<br>MTNETGRKEGTPAEVDKGGKYPQHTCVRKFCDKSPYTCSVKGPIFGECLDGQWNFTALDECLNARGCN<br>SDDLFDKLGFEGVMVREEEGSDSYKDDFVRFYATGSKVNAECKGKTVQLECSDGEWHDPGTKTVHRCT<br>KEGIRAL |
| Notes | 78 changes throughout, same length (81.5% identity) |

TGM-f

| | |
|---|---|
| Assembly | Hp_I03144_IG00345_L1870 |
| Nucleotide Sequence | TTTTGTCCAAAGAATCGTTTATTCAACTGTGGCAAACACTGAGTTTATTCGTCATAGGTGACTCCGCT<br>ATCAGTGCATCGTATTTTAGCGAATTTTCTCTCATTCTCGGCATGACGACGTCCTTGCCATCCACCTTC<br>AAAGCATTCAAGATCTGCCGGGTTACCTTTGCAAAGTGCTTGTATTTTCGAACCAGGTCCGTAAAAT<br>GTAGAAACAGTATCAGGTTTCTTGTATACTGCCACCGCAAGACGTGTATCGACTATAGTTGAGGTGA<br>ATTTCAGATCCAAATAAACCTCGTTTATATTGCAGCTCCCCTGTGGTGGACATGGCCATGTGTTGCG<br>GTGCACCCATCCGTTCGCGCCGCATTTGGAGATATCCCCTTGAGCCCTGCTGTTTACGTCTAGTTTCT<br>TGCAAATCCTCCGAGCATACGAGCCCACAGCGAATTTCCCACTCCAGTCTAGTACGGCAATATTTGC<br>GAAATCGTTACTTGTTTGCTCACTTTTAAAGTACTTGTATTCCACGGTGTCGTTCTCGGCCAACGGTA<br>AGCATCCAAGAATAGGACATTGTAGCACCGTCGCTTCATTCTCCTTCACCCATTCGCCTTTGCTGCAT<br>CTTCCAGCGATTTCTCCTAAGTTTTTGTTATCGCCAGTTGCCTTCTTACAAAACATCTTTGCAGACGTG<br>CGTTCGGGGTATTTTCCAGACCGTGGCTTTACAGTGGAGGTGCTTAGTGTATAGTAGCCTGTGCGTG<br>ATATATTGGATACTCATATCTTACGGTGTCGTTGTCCGTAAGAGGGGCGCATTCACGCCCAGGGCA<br>TTCCGGTATGATTTGGTACTTTTCTGGCTTCCATTGGCGATTGCTGCATTGTGCAATAATTGTCCCTGT<br>TTTTTTCGCCTATTCTAGTCGGTATCTTACAGATGACTATCGCAAACGTGCCGTCAGGGTATTCTCCGC<br>TCTGCGGTGTCGCTTCCTTTGCGACGACAGTTTGGTCAGGAGACATTGTGTATTGGAGATACTTATAC<br>GTAAGGTACTGTTGGCTTTATATGTTATGGTAACAGCCAGGACTGGGCACTGTCTGTTTTATATTATGA<br>GTACACCCACCGACTTTCACCAGTATCACTTCTTTCGTGGCAAATGGCGACAAGTTCCCCCTTGATCA<br>ACCTTTACGCTCCGTGCTTGGCAATGCCTCTTGCATGCGTCTGTGGAGGGTAATTTCCAGAACTGTC<br>CTTAGTTACTGCTTGTCCGACGACATCTCGACTCCCAGCGTATTCATAGTATTCGTGCCGGAATTTGT<br>CATTGTCTTGTATCGGTGGGCAACCATAGGGTGGGCATACTGGTGCGCTGGAGAACCTCCATTCAG<br>CATTGTAGCACATGCCGACAATAACACCTCGAACTTTGCTGTTTGCAGGAAAATTTTTGCATATTCTT |

TABLE 1-continued

| | |
|---|---|
| | CTTATGTATGTTAGTTCAGGATATTTTCCGCTGTCATCTGGATTGGCACTTGTATCATAACTGATTCTC<br>GAAGAATTTAGAGTAGCTTTACGATACTCGTAGCTGACAGTATCGCTCTCAGACAACGGCGAGCATC<br>TACGGTCTCGGCATTCTTGTACTCCCATATAATAGACCCATTCCGATCGATGGCACAGGCCGATGAA<br>CTCACCTGTCTTATCTTCTCCATGCAATCCTTTACAAAACCGTTTCACGTGCGTATACTCAGGATACAT<br>TCCAGAACTGTCCTTTCGCGCAGGTGTTTCCTCTTTATTAGAAGTTTGTGCAAAATATTGGTAGGTGT<br>CAGTTTCTTCAGATAATGGCATGCAGCTGTTGTCGCCTGCAGCCGAAGCCTCGAGAAGGCCAATTAC<br>TACAATCAGCAGCATTTCACTCAAACTTGGGTAATTAAACC |
| Nucleotide<br>Sequence<br>ORF | ATGCTGCTGATTGTAGTAATTGGCCTTCTCGAGGCTTCGGCTGCAGGCGACAACAGCTGCATGCCAT<br>TATCTGAAGAAACTGACACCTACCAATATTTTGCACAAACTTCTAATAAAGAGGAAACACCTGCGCG<br>AAAGGACAGTTCTGGAATGTATCCTGAGTATACGCACGTGAAACGGTTTTGTAAAGGATTGCATGG<br>AGAAGATAAGACAGGTGAGTTCATCGGCCTGTGCCATCGATCGGAATGGGTCTATTATATGGGAGT<br>ACAAGAATGCCGAGACCGTAGATGCTCGCCGTTGTCTGAGAGCGATACTGTCAGCTACGAGTATCG<br>TAAAGCTACTCTAAATTCTTCGAGAATCAGTTATGATACAAGTGCCAATCCAGATGACAGCGGAAAA<br>TATCCTGAACTAACATACATAAGGAAGAATATGCAAAAATTTTCCTGCAAACAGCAAAGTTCGAGGTG<br>TTATTGTCGGCATGTGCTACAATGCTGAATGGAGGTTCTCCAGCGCACCAGTATGCCCACCCTATGG<br>TTGCCCACCGATACAAGACAATGACAAATTCCGGCACGAATACTATGAATACGCTGGGAGTCGAGA<br>TGTCGTCGGACAAGCAGTAACTAAGGACAGTTCTGGAAATTACCCTCCACAGACGCATGCAAGAAG<br>GCATTGCCAAGCACGGAGCGTAAAGGTTGATCAAGGGGAACTTGTCGCCATTTGCCACGAAAGAA<br>GTGATACTGGTGAAAGTCGGTGGGTGTACTATCATAATATAAAACAGTGCCCAGTTCCTGGCTGTAC<br>CATAACATATAAAGCCAACAGTACCGTTACGTATAAGTATCTCCAAATACAATGTCTCCTGACCAA<br>ACTGTCGTCGCAAAGGAAGCGACACCGCAGAGCGGAGAATACCCTGACGGCACGTTTGCCGATAGT<br>CATCTGTAAGATACCGACTAGAATAGGCGAAAAACAGGGACAATTATTGCACAATGCAGCAATCG<br>CCAATGGAAGCCAGAAAAGTACCAAATCATACCGGAATGCCCTGGGCGTGAATGCGCCCCTCTTAC<br>GGACAACGACACCGTAAGATATGAGTATCTCAATATATCACGCACAGGCTACTATACACTAAGCAC<br>CTCCACTGTAAAGCCACGGTCTGGAAAATACCCCGAACGCACGTCTGCAAAGATGTTTTGTAAGAA<br>GGCAACTGGCGATAACAAAAACTTAGGAGAAATCGCTGGAAGATGCAGCAAAGGCGAATGGGTGA<br>AGGAGAATGAAGCGACGGTGCTACAATGTCCTATTCTTGGATGCTTACCGTTGGCCGAGAACGACA<br>CCGTGGAATACAAGTACTTTAAAAGTGAGCAAACAAGTAACGATTTCGCAAATATTGCCGTACTAGA<br>CTGGAGTGGGAAATTCGCTGTGGGCTCGTATGCTCGGAGGATTTGCAAGAAACTAGACGTAAACAG<br>CAGGGCTCAAGGGGATATCTCCAAATGCGGCGCGAACGGATGGGTGCACCGCAACACATGGCCAT<br>GTCCACCACAGGGGAGCTGCAATATAAACGAGGTTTATTTGGATCTGAAATTCACCTCAACTATAGT<br>CGATACACGTCTTGCGGTGGCAGTATACAAGAAACCTGATACTGTTTCTACATTTTACGGACCTGGTT<br>CGAAAATACAAGCACTTTGCAAAGGTAACCCGGCAGATCTTGAATGCTTTGAAGGTGGATGGCAAG<br>GACGTCGTCATGCCGAGAATGAGAGAAAATTCGCTAAAATACGATGCACTGATAGCGGAGTCACCT<br>ATGACGAATAA |
| Amino Acid<br>Sequence | MLLIVVIGLLEASAAGDNSCMPLSEETDTYQYFAQTSNKEETPARKDSSGMYPEYTHVKRFCKGLHGEDK<br>TGEFIGLCHRSEWVYYMGVQECRDRRCSPLSESDTVSYEYRKATLNSSRISYDTSANPDDSGKYPELTYIR<br>RICKNFPANSKVRGVIVGMCYNAEWRFSSAPVCPPYGCPPIQDNDKFRHEYYEYAGSRDVVGQAVTKD<br>SSGNYPPQTHARRHCQARSVKVDQGELVAICHERSDTGESRWVYYHNIKQCPVPGCTITYKANSTVTYK<br>YLQYTMSPDQTVVAKEATPQSGEYPDGTFAIVICKIPTRIGEKTGTIIAQCSNRQWKPEKYQIIPECPGREC<br>APLTDNDTVRYEYLNISRTGYYTLSTSTVKPRSGKYPERTSAKMFCKKATGDNKNLGEIAGRCSKGEWVK<br>ENEATVLQCPILGCLPLAENDTVEYKYFKSEQTSNDFANIAVLDWSGKFAVGSYARRICKKLDVNSRAQG<br>DISKCGANGWVHRNTWPCPPQGSCNINEVYLDLKFTSTIVDTRLAVAVYKKPDTVSTFYGPGSKIQALCK<br>GNPADLECFEGGWQGRRHAENERKFAKIRCTDSGVTYDE |
| Comments | Larval, not adult, parasite product. Matches TGM 1-196 (72 changes, 63.3% identity<br>incl. 9/9 Cys) and 197-422 (only 63 identities, 27.9% identical, incl 11/13 Cys) with<br>175-aa insertion (incl. 6 cysteines) |
| | TGM-g |
| Assembly | Hp_I03145_IG00345_L1870 |
| Nucleotide<br>Sequence | TTTTGTCCAAAGAATCGTTTATTCAACTGTGGCAAACACTGAGTTTATTCGTCATAGGTGACTCCGCT<br>ATCAGTGCATCGTATTTTAGCGAATTTTCTCTCATTCTCGGCATGACGACGTCCTTGCCATCCACCTTC<br>AAAGCATTCAAGATCTGCCGGGTTACCTTTGCAAAGTGCTTGTATTTTCGAACCAGGTCCGTAATAT<br>GGTGAAACAGTACCAGGTTTCTGGTATACTGCCACCGCAAGACTTGTATGGACTATAGTTGAGGTGA<br>ATTTCTGATCCAGAAAAACATCGCTTATATCGCAACTCCCGCGTGGGGGGCATGGCCATGTGTTGCT<br>GTGCTCCCATCCGTTCTCCCCGCATTTGGAGATATCCCCTTGAGCCTCGCTTTTTCGTCCAGTTCCTT<br>GCAAATCCTCCAAGCATACGAGCCCACAGCGAACTTTCCACTCCAATCTAGTGGGGCAATATTTTCG<br>TGCGCGATATTTGGATGTTCACTTTTGAAGTACTTGTATTCCACGGTGTCGTTCTCGTGCAACGGTAG<br>GCATCCAAGAATAGGACATTGTAGCACCGTCGCTTCATTCTCCTTCACCCATTCGCCTTTGCTGCATC<br>TTCCAGCGATTTCCCCTAAGTTTTTGTTATCGTCAGTTGCCTTCTTACAAAACATCTTTGCAGACGTGC<br>CTTCGGGGTATTTTCCAGACCGTGGCTTTACCTTGGAGGTGCTTAGTGTATAGTAGCCTGTGCGTGAT<br>ATATTGAGATACTCATATCTTACGGTGTCGTTGTCCGTAAGAGGGGCGCATTCACGCCTCAGGCATT<br>CCGGTACGATTTGGTACTTTTCCGGCTTCCATTTGCGATTGCTGCATTGTGCAAAATTGTCCCTGTTT<br>TTTCGCCTATTCTAGTCGGTATCTTACAGATGACTATCGCAAACGTGCCGTCAGGGTATTCTCCGCCC<br>TGCGGTGTCGCTTCCTTTGCGACGACAGTTTGGTCAGGAGATATTGTGTATTGGAGATACTTATACGT<br>AACGGTACTGTTGTCTTCATATGCTGTGGTACAGCCATGATCTGGGCATTGTTTTATATTAAGATAGT<br>ACACCCACCGACTTTCACCAGTACTATCTCTTCGAGGCAAATGGCGACAAATTCCCCTTGACCATC<br>CTTTCCGCTCCCTGCGCTGCAACGCCTTCTTGCATGCGTCTGGAGGGTAATTTCCAGAACTGTCCT<br>TAGTTGCTGCTGGTCCGAGTTTTTCTCGACTCCCAGCGTATTTATAGTATTCGTGCCGGAAATTGTCA<br>TTGTCTTGTATCGGTGGGCAACCGTAGGGTGGGTGTCCTGGGAAAACCTCCAATCCAGCAT<br>TGTAGCACATGCCGACAATGAGACCTCGAATTTTGCTGTCTACAGAAAAATTTTTGCAGGTTCTTCTA<br>ATGTATGTTAGTTCAGGATATTTTCCGCTGCTATCTGGATTGGCATTTGTATCATAACTGATTCTCGAA<br>GAATTTAGAGTAGCTTTACGATACTCGTAGCTGACAGTATCGCTCTCAGACAACGGCGAGCATCTAC<br>GGTCTCGGCATTCTTTTACTCCCATATAATAGACCCATTCTGATCGATGGCACAGGCCGATGAACTC<br>ACCTGTCTTATCTTCTCCATGCAATCCTTTACAAAACCGTTTCACGTGCGTATACTCAGGATACATTCC |

TABLE 1-continued

|  |  |
|---|---|
|  | AGAACTGTCCTTTCGCGCAGGTGTTTCCTCTTTATTAGAAGTTTGTGCAAAATATTGGTAGGTGTCAG<br>TTTCTTCAGATAATGGCATGCAGCTGTTGTCGCCTGCAGCCGAAGCCTCGAGAAGGCCAATTACTAC<br>AATCAGCAGCATTTCACTCAAACTTGGGTAATTAAACC |
| Nucleotide<br>Sequence<br>ORF | ATGCTGCTGATTGTAGTAATTGGCCTTCTCGAGGCTTCGGCTGCAGGCGACAACAGCTGCATGCCAT<br>TATCTGAAGAAACTGACACCTACCAATATTTTGCACAAACTTCTAATAAAGAGGAAACACCTGCGCG<br>AAAGGACAGTTCTGGAATGTATCCTGAGTATACGCACGTGAAACGGTTTTGTAAAGGATTGCATGG<br>AGAAGATAAGACAGGTGAGTTCATCGGCCTGTGCCATCGATCAGAATGGGTCTATTATATGGGAGT<br>AAAAGAATGCCGAGACCGTAGATGCTCGCCGTTGTCTGAGAGCGATACTGTCAGCTACGAGTATCG<br>TAAAGCTACTCTAAATTCTTCGAGAATCAGTTATGATACAAATGCCAATCCAGATAGCAGCGGAAAA<br>TATCCTGAACTAACATACATTAGAAGAACCTGCAAAAATTTTTCTGTAGACAGCAAAATTCGAGGTC<br>TCATTGTCGGCATGTGCTACAATGCTGAGTGGAGGTTTTCCAGCACACCAGAATGCCCACCCTACGG<br>TTGCCCACCGATACAAGACAATGACAATTTCCGGCACGAATACTATAAATACGCTGGGAGTCGAGA<br>AAAACTCGGACCAGCAGCAACTAAGGACAGTTCTGGAAATTACCCTCCACAGACGCATGCAAGAA<br>GGCGTTGCAGCGCAGGGAGCGGAAAGGATGGTCAAGGGGAATTTGTCGCCATTTGCCTCGAAAGA<br>GATAGTACTGGTGAAAGTCGGTGGGTGCTACTATCTTAATATAAAACAATGCCCAGATCCTGGCTGTA<br>CCACAGCATATGAAGACAACAGTACCGTTACGTATAAGTATCTCCAATACACAATATCTCCTGACCA<br>AACTGTCGTCGCAAAGGAAGCGACACCGCAGGGCGGAGAATACCCTGACGGCACGTTTGCGATAG<br>TCATCTGTAAGATACCGACTAGAATAGGCGAAAAAACAGGGACAATTTTTGCACAATGCAGCAATC<br>GCAAATGGAAGCCGGAAAAGTACCAAATCGTACCGGAATGCCCTGGGCGTGAATGCGCCCCTCTTA<br>CGGACAACGACACCGTAAGATATGAGTATCTCAATATATCACGGCACGAACCGGCTACTATACACTAAGCA<br>CCTCCAAGGTAAAGCCACGGTCTGGAAAATACCCCGAAGGCACGTCTGCAAAGATGTTTTGTAAGA<br>AGGCAACTGACGATAACAAAAACTTAGGGGAAATCGCTGGAAGATGCAGCAAAGGCGAATGGGTG<br>AAGGAGAATGAAGCGACGGTGCTACAATGTCCTATTCTTGGATGCCTACCGTTGCACGAGAACGAC<br>ACCGTGGAATACAAGTACTTCAAAAGTGAACATCCAAATATCGCGCACGAAAATATTGCCCCACTA<br>GATTGGAGTGGAAAGTTCGCTGTGGGCTCGTATGCTTGGAGGATTTGCAAGGAACTGGACGAAAAA<br>AGCGAGGCTCAAGGGGATATCTCCAAATGCGGGGAGAACGGATGGGAGCACAGCAACACATGGC<br>CATGCCCCCCACGCGGGAGTTGCGATATAAGCGATGTTTTTCTGGATCAGAAATTCACCTCAACTAT<br>AGTCCATACAAGTCTTGCGGTGGCAGTATACCAGAAACCTGGTACTGTTTCACCATATTACGGACCT<br>GGTTCGAAAATACAAGCACTTTGCAAAGGTAACCCGGCAGATCTTGAATGCTTTGAAGGTGGATGG<br>CAAGGACGTCGTCATGCCAGAATGAGAGAAAATTCGCTAAAATACGATGCACTGATAGCGGAGTC<br>ACCTATGACGAATAA |
| Amino Acid<br>Sequence | MLLIVVIGLLEASAAGDNSCMPLSEETDTYQYFAQTSNKEETPARKDSSGMYPEYTHVKRFCKGLHGEDK<br>TGEFIGLCHRSEWVYYMGVKECRDRRCSPLSESDTVSYEYRKATLNSSRISYDTNANPDSSGKYPELTYIRR<br>TCKNFSVDSKIRGLIVGMCYNAEWRFSSTPECPPYGCPPIQDNDNFRHEYYKAGSREKLGPAATKDSSG<br>NYPPQTHARRRCSAGSGKDGQGEFVAICLERDSTGESRWVYYLNIKQCPDPGCTTAYEDNSTVTYKYLQ<br>YTISPDQTVVAKEATPQGGEYPDGTFAIVICKIPTRIGEKTGTIFAQCSNRKWKPEKYQIVPECPGRECAPLT<br>DNDTVRYEYLNISRTGYYTLSTSKVKPRSGKYPEGTSAKMFCKKATDDNKNLGEIAGRCSKGEWVKENEA<br>TVLQCPILGCLPLHENDTVEYKYFKSEHPNIAHENIAPLDWSGKFAVGSYAWRICKELDEKSEAQGDISKC<br>GENGWEHSNTWPCPPRGSCDISDVFLDQKFTSTIVHTSLAVAVYQKPGTVSPYYGPGSKIQALCKGNPA<br>DLECFEGGWQGRRHAENERKFAKIRCTDSGVTYDE |
| Comments | Larval, not adult, parasite product. |

TGM-h

|  |  |
|---|---|
| Assembly | Hp_I18123_IG10067_L851 |
| Nucleotide<br>Sequence | TTTATATTCAAAATATTTATGCACTTCAGCTGTGAAGACTGTCTCATTCGCAAAGCGCTTTTCTGCCG<br>TCCGCTGTAACCCAATGGCCGCCGTCAGCACATGTTAACTTCACAGATTCACCTTTGCACTTCGCAG<br>TGACTCTCGAACCGGACGATAATGCCTGTATGTATTGTCTTCGGAAAATTTTGCTGGCTGATTTACC<br>CAGTATGAAATATCACTGAACATTAGCTTCTCAAGCAGATATTCTTCGTCACATCCTGCTGCGAATCG<br>ACAGTCTGGCAAATTTTTAAGCTTCCACTCTGAATCCAAGCACTCTGCGTAGGTCTCCGCTTGAGCTA<br>GACTATTCCTTGGAAGCTCATTGCAATACCTTCTAACTAGTGTTTGTTCGGGATACTTTCCGCTTCCGT<br>CCGGGTTTGTAAGTGTACCCATGCCCTTCCTTCAGCCGCTTTTGTGTAATATTCATAGCTCACAGAA<br>ACACTCTTTTTCAGAGGCTCGCACCGAGGGTCCGGGCATGCCGTTATATTACGATAGTACATCCATT<br>GACTTCCACGTCTTTTGGTAGCAAATGGCGACAAATACCCCTGGGTCAGCTTTTTTACTGAGAGCCTT<br>ACAATGCGCTCTTGCATGCGTCTGCGGAGGATAATTTCCAGAAGTGTCCTTAGTTGCTGCTTCCCCG<br>ACGGTGTGACGATTTTCAACGTATTCGTAATATTCGTACCACACAGTTTCATTGTCCGGAAGAGGTA<br>GGCAACTTGATCCAACAGCTTCAACCAGTCCGATAGCAACGAATAATAGGAGCATCTTGATGGAGC<br>GTCGATGAGCACAATGGTCTCAAACTTGGGTAATTAAACC |
| Nucleotide<br>Sequence<br>ORF | ATGCTCCTATTATTCGTTGCTATCGGACTGGTTGAAGCTGTTGGATCAAGTTGCCTACCTCTTCCGGA<br>CAATGAAACTGTGTGGTACGAATATTACGAATACGTTGAAATCGTCACACCGTCGGGGAAGCAGC<br>AACTAAGGACACTTCTGGAAATTATCCTCCGCAGACGCATGCAAGAGCGCATTGTAAGGCTCTCAG<br>TAAAAAAGCTGACCCAGGGGTATTTGTCGCCATTTGCTACCAAAGACGTGGAAGTCAATGGATGTA<br>CTATCGTAATATAACGGCATGCCCGGACCCTCGGTGCGAGCCTCTGAAAAAGAGTGTTTGCTGTGAG<br>CTATGAATATTACACAAAAGCGGCTGAAGGAAAGGGCATGGGTACACTTACAAACCCGGACGGAA<br>GCGGAAAGTATCCCGAACAAACACTAGTTAGAAGGTATTGCAATGAGCTTCCAAGGAATAGTCTAG<br>CTCAAGCGGAGACCTACGCAGAGTGCTTGGATTCAGAGTGGAAGCTTAAAAATTTGCCAGACTGTC<br>GATTCGCAGCAGGATGTGACGAAGAATATCTGCTTGAGAAGCTAATGTTCAGTGATATTTCATACTG<br>GGTAAATCAGCCAGCAAAATTTTCCGAAGACAATACATACAGGCATTATCGTCCCGGTTCGAGAGT<br>CACTGCGAAGTGCAAAGGTAATCTGTGAAGTTAACATGTGCTGACGGCGGCCATTGGGTTACAGC<br>GGACGGCAGAAAAGCGCTTTGCGAATGA |

TABLE 1-continued

| | |
|---|---|
| Amino acid Sequence | MLLLFVAIGLVEAVGSSCLPLPDNETVWYEYYEYVENRHTVGEAATKDTSGNYPPQTHARAHCKALSKKA DPGVFVAICYQRRGSQWMYYRNITACPDPRCEPLKKSVSVSYEYYTKAAEGKGMGTLTNPDGSGKYPEQ TLVRRYCNELPRNSLAQAETYAECLDSEWKLKNLPDCRFAAGCDEEYLLEKLMFSDISYWVNQPAKFSED NTYRHYRPGSRVTAKCKGESVKLTCADGGHWVTADGRKALCE |
| Comments | Larval, not adult, parasite product. |

TGM-i

| | |
|---|---|
| Assembly | Hp_I18218_IG10162_L844 |
| Nucleotide Sequence | GTTTAATTACCCAAGTTTGAGAACTAACGCATTTAAGTTAAATGTGGTTCTCCCTAATTGCAGTCGCA GTTTTCAACGTTGCAGGAGCAAGTGATGGTTGCCTGCCACTATCTGAGGAAACGGCCACTTATGAAT ATTATGCATACAGCGGGAGTCGGTATGTTGACGGTAACCCCACAGAAAAGGACAGTTCCGGAAGGT ATCCTCATGGCACACATGCCAAGCGATTTTGCAAAGGCTCAGATGAAGAGGCAGGGTTGTTCGTAG CCATATGCGTTAAATATAGATGGGTGTACTACAAGGACGTAAAGCCGTGTCCAGACTTTAGGTGTCA ACCGCTGACGCCAAATGAAACTATCAGCAATTACCAGTACCTCAAAGAAACCACCAATTCTGGAGG AGAAAGCTTTGAAGTCGTCCAACCGGATGCCGACGGAAAATATCCTGAGCTGACGTACATAAGGAG AACGTGCAATGAGTTTCCCACAGACAGAAAGCTACAAAGAGATATCGCCGGCCTTTGCTACAAAGC CGAATGGTTTCTACGAACCTGTCCGACTCCCGGAAATTGCTACGACGACGATATACGCACAAAGTT GAAGTACCAAGGATATTCATTTGACTATGAAACTGCCGAAGTGACTTACTCATTCGGTAATGACGGA GCGCATTATTTCATAGAGGGCTCTCAGGTCACAGGAATTTGTAACGGTTATCAAGTACCCCTATGGT GCCAGGATGGTGAATGGATCGGAGAGGTAAAGAACATTTCCTGCGATATGATGAACGCACAGTAG CATCGTACAGCCAGTGTCTGCGGGACACAATAAATATTTTATTTCTT |
| Nucleotide Sequence ORF | ATGTGGTTCTCCCTAATTGCAGTCGCAGTTTTCAACGTTGCAGGAGCAAGTGATGGTTGCCTGCCAC TATCTGAGGAAACGGCCACTTATGAATATTATGCATACAGCGGGAGTCGGTATGTTGACGGTAACC CCACAGAAAAGGACAGTTCCGGAAGGTATCCTCATGGCACACATGCCAAGCGATTTTGCAAAGGCT CAGATGAAGAGGCAGGGTTGTTCGTAGCCATATGCGTTAAATATAGATGGGTGTACTACAAGGACG TAAAGCCGTGTCCAGACTTTAGGTGTCAACCGCTGACGCCAAATGAAACTATCAGCAATTACCAGTA CCTCAAAGAAACCACCAATTCTGGAGGAGAAAGCTTTGAAGTCGTCCAACCGGATGCCGACGGAA AATATCCTGAGCTGACGTACATAAGGAGAACGTGCAATGAGTTTCCCACAGACAGAAAGCTACAAA GAGATATCGCCGGCCTTTGCTACAAAGCCGAATGGTTTCTACGAACCTGTCCGACTCCCGGAAATTG CTACGACGACGATATACGCACAAAGTTGAAGTACCAAGGATATTCATTTGACTATGAAACTGCCGA AGTGACTTACTCATTCGGTAATGACGGAGCGCATTATTTCATAGAGGGCTCTCAGGTCACAGGAATT TGTAACGGTTATCAAGTACCCCTATGGTGCCAGGATGGTGAATGGATCGGAGAGGTAAAGAACATT TCCTGCGATATGATGAACGCACAGTAG |
| Amino Acid Sequence | MWFSLIAVAVFNVAGASDGCLPLSEETATYEYYAYSGSRYVDGNPTEKDSSGRYPHGTHAKRFCKGSDE EAGLFVAICVKYRWVYYKDVKPCPDFRCQPLTPNETISNYQYLKETTNSGGESFEVVQPDADGKYPELTYI RRTCNEFPTDRKLQRDIAGLCYKAEWFLRTCPTPGNCYDDDIRTKLKYQGYSFDYETAEVTYSFGNDGAH YFIEGSQVTGICNGYQVPLWCQDGEWIGEVKNISCDMMNAQ |
| Comments | Larval, not adult, parasite product. |

REFERENCES

1. Maizels, R. M. & Yazdanbakhsh, M. Regulation of the immune response by helminth parasites: cellular and molecular mechanisms. *Nat. Rev. Immunol.* 3, 733-743 (2003).
2. Elliott, D. E., Summers, R. W. & Weinstock, J. V. Helminths as governors of immune-mediated inflammation. *Int J Parasitol* 37, 457-464 (2007).
3. McSorley, H. J. & Maizels, R. M. Helminth infections and host immune regulation. *Clin Micro Rev* 25, 585-608 (2012).
4. Taylor, M., et al. Removal of regulatory T cell activity reverses hyporesponsiveness and leads to filarial parasite clearance in vivo. *J. Immunol.* 174, 4924-4933 (2005).
5. Blankenhaus, B., et al. *Strongyloides ratti* infection induces expansion of Foxp3+ regulatory T cells that interfere with immune response and parasite clearance in BALB/c mice. *J Immunol* 186, 4295-4305 (2011).
6. Maizels, R. M. & Smith, K. A. Regulatory T cells in infection. *Adv mmuno*/112, 73-136 (2011).
7. Finney, C. A. M., Taylor, M. D., Wilson, M. S. & Maizels, R. M. Expansion and activation of CD4+CD25+ regulatory T cells in Heligmosomoides polygyrus infection. *Eur. J. Immunol.* 37, 1874-1886 (2007).
8. Rausch, S., et al. Functional analysis of effector and regulatory T cells in a parasitic nematode infection. *Infect. Immun.* 76, 1908-1919 (2008).
9. Grainger, J. R., et al. Helminth secretions induce de novo T cell Foxp3 expression and regulatory function through the TGF-β pathway. *J Exp Med* 207, 2331-2341 (2010).
10. Smith, K. A., et al. Low level regulatory T cell activity is essential for functional type-2 effector immunity to expel gastrointestinal helminths. *Mucosal Immunol* (2016).
11. Chen, W., et al. Conversion of peripheral CD4+CD25− naive T cells to CD4+CD25+ regulatory T cells by TGF-β induction of transcription factor Foxp3. *J Exp Med* 198, 1875-1886 (2003).
12. Peng, Y., Laouar, Y., Li, M. O., Green, E. A. & Flavell, R. A. TGF-β regulates in vivo expansion of Foxp3-expressing CD4+CD25+ regulatory T cells responsible for protection against diabetes. *Proc. Natl. Acad. Sci. USA* 101, 4572-4577 (2004).
13. Bilate, A. M. & Lafaille, J. J. Induced CD4+Foxp3+ regulatory T cells in immune tolerance. *Annu Rev Immunol* 30, 733-758 (2012).
14. Tran, D. Q. TGF-β: the sword, the wand, and the shield of FOXP3+ regulatory T cells. *J Mol Cell Biol* 4, 29-37 (2012).
15. Li, M. O. & Flavell, R. A. TGF-β: a master of all T cell trades. *Cell* 134, 392-404 (2008).
16. Sanford, L. P., et al. TGFbeta2 knockout mice have multiple developmental defects that are non-overlapping with other TGFbeta knockout phenotypes. *Development* 124, 2659-2670 (1997).

17. Proetzel, G., et al. Transforming growth factor-beta 3 is required for secondary palate fusion. *Nat Genet* 11, 409-414 (1995).
18. Patterson, G. I. & Padgett, R. W. TGF b-related pathways. Roles in *Caenorhabditis elegans* development. *Trend. Genet.* 16, 27-33 (2000).
19. McSorley, H. J., et al. daf-7-related TGF-β homologues from trichostrongyloid nematodes show contrasting life cycle expression patterns. Parasitology 137, 159-171 (2010).
20. Hinck, A. P., Mueller, T. D. & Springer, T. A. Structural biology and evolution of the TGF-β family. *Cold Spring Harbor* perspectives in biology in press (2016).
21. Hewitson, J. P., et al. Proteomic analysis of secretory products from the model gastrointestinal nematode Heligmosomoides polygyrus reveals dominance of Venom Allergen-Like (VAL) proteins. *J Proteomics* 74, 1573-1594 (2011).
22. Moreno, Y., et al. Proteomic analysis of excretory-secretory products of Heligmosomoides polygyrus assessed with next-generation sequencing transcriptomic information. *PLoS Negl Trop Dis* 5, e1370 (2011).
23. Wilson, M. S., et al. Suppression of allergic airway inflammation by helminth-induced regulatory T cells. *J. Exp. Med.* 202, 1199-1212 (2005).
24. Johnston, C. J. C., et al. Cultivation of Heligmosomoides polygyrus: an immunomodulatory nematode parasite and its secreted products. *Journal of Visualized Experiments* 98, e52412 (2015).
25. Tesseur, I., Zou, K., Berber, E., Zhang, H. & Wyss-Coray, T. Highly sensitive and specific bioassay for measuring bioactive TGF-β. *BMC Cell Biol* 7, 15 (2006).
26. Fontenot, J. D., et al. Regulatory T cell lineage specification by the forkhead transcription factor Foxp3. *Immunity* 22, 329-341 (2005).
27. Dasch, J. R., Pace, D. R., Waegell, W., Inenaga, D. & Ellingsworth, L. Monoclonal antibodies recognizing transforming growth factor-b. Bioactivity neutralization and transforming growth factor b2 affinity purification. *J. Immunol.* 142, 1536-1541 (1989).
28. Billingham, R. E., Brent, L. & Medawar, P. B. Acquired tolerance of skin homografts. *Annals of the New York Academy of Sciences* 59, 409-416 (1955).
29. Zdichavsky, M., et al. Scoring of skin rejection in a swine composite tissue allograft model. *J Surg Res* 85, 1-8 (1999).
30. Inman, G. J., et al. SB-431542 is a potent and specific inhibitor of transforming growth factor-β superfamily type I activin receptor-like kinase (ALK) receptors ALK4, ALK5, and ALK7. *Molecular pharmacology* 62, 65-74 (2002)
31. Willems, E., et al. Small molecule-mediated TGF-beta type II receptor degradation promotes cardiomyogenesis in embryonic stem cells. *Cell Stem Cell* 11, 242-252 (2012).
32. Johnston, C. J., McSorley, H. J., Anderton, S. M., Wigmore, S. J. & Maizels, R. M. Helminths and immunological tolerance. *Transplantation* 97, 127-132 (2013).
33 Chen, L., et al. TLR engagement prevents transplantation tolerance. *Am J Transplant* 6, 2282-2291 (2006).
34. Tang, J., et al. IL-25 promotes the function of CD4+ CD25+T regulatory cells and prolongs skin-graft survival in murine models. *Int Immunopharmacol* 28, 931-937 (2015).
35. Bettelli, E., et al. Reciprocal developmental pathways for the generation of pathogenic effector TH17 and regulatory T cells. *Nature* 441, 235-238 (2006).
36. Veldhoen, M., Hocking, R. J., Atkins, C. J., Locksley, R. M. & Stockinger, B. TGFβ in the context of an inflammatory cytokine milieu supports de novo differentiation of IL-17-producing T cells. *Immunity* 24, 179-189 (2006).
37. Alcami, A. Viral mimicry of cytokines, chemokines and their receptors. *Nat Rev Immunol* 3, 36-50 (2003).
38. Li, M. O., Wan, Y. Y., Sanjabi, S., Robertson, A. K. & Flavell, R. A. Transforming growth factor-β regulation of immune responses. *Annu. Rev. Immunol* 24, 99-146 (2006).
39. Marie, J. C., Letterio, J. J., Gavin, M. & Rudensky, A. Y. TGF-β1 maintains suppressor function and Foxp3 expression in $CD4^+CD25^+$ regulatory T cells. *J Exp Med* 201, 1061-1067 (2005).
40. Liu, Y., et al. A critical function for TGF-beta signaling in the development of natural CD4+CD25+Foxp3+ regulatory T cells. *Nat Immunol* 9, 632-640 (2008).
41. Estevez, M., et al. The daf-4 gene encodes a bone morphogenetic protein receptor controlling *C. elegans* dauer larva development. *Nature* 365, 644-649 (1993).
42. Gomez-Escobar, N., Gregory, W. F. & Maizels, R. M. Identification of Bm-tgh-2, a filarial nematode homolog of *C. elegans* daf-7 and human TGF-b, expressed in microfilarial and adult stages of *Brugia malayi. Infect. Immun.* 68, 6402-6410 (2000).
43. Beall, M. J. & Pearce, E. J. Human transforming growth factor-β activates a receptor serine/threonine kinase from the intravascular parasite *Schistosoma mansoni. J Biol Chem* 276, 31613-31619 (2001).
44. Zavala-Gongora, R., Kroner, A., Bernthaler, P., Knaus, P. & Brehm, K. A member of the transforming growth factor-b receptor family from *Echinococcus multilocularis* is activated by human bone morphogenetic protein 2. *Mol. Biochem. Parasitol.* 146, 265-271 (2006).
45. Robertson, I. B. & Rifkin, D. B. Unchaining the beast; insights from structural and evolutionary studies on TGF-beta secretion, sequestration, and activation. *Cytokine Growth Factor Rev* 24, 355-372 (2013).
46. Tang, Y. T., et al. Genome of the human hookworm *Necator americanus. Nat Genet* 46, 261-269 (2014).
47 Chauhan, S. K., Saban, D. R., Lee, H. K. & Dana, R. Levels of Foxp3 in regulatory T cells reflect their functional status in transplantation. *J Immunol* 182, 148-153 (2009).
48. Zhou, L., et al. TGF-b-induced Foxp3 inhibits TH17 cell differentiation by antagonizing RORgt function. *Nature* 453, 236-240 (2008).
49. Onichtchouk, D., et al. Silencing of TGF-beta signalling by the pseudoreceptor BAMBI. *Nature* 401, 480-485 (1999).
50. Yang, X. O., et al. Molecular antagonism and plasticity of regulatory and inflammatory T cell programs. *Immunity* 29, 44-56 (2008).
51. Sawant, D. V. & Vignali, D. A. Once a Treg, always a Treg? *Immunol Rev* 259, 173-191 (2014).
52 Marek-Trzonkowska, N., et al. Administration of CD4+ CD25highCD127− regulatory T cells preserves beta-cell function in type 1 diabetes in children. *Diabetes Care* 35, 1817-1820 (2012).

The invention claimed is:

1. An isolated, non-glycosylated polypeptide comprising an amino acid sequence having at least 95% sequence identity with amino acid sequences of each of domain 1, domain 2 and domain 3 of a TGM protein selected from the group consisting of

TGM (SEQ ID NO: 20);

TGM-a (SEQ ID NO: 23); and

TGM-d (SEQ ID NO: 32);

wherein said polypeptide has TGF-β receptor agonist activity, and each glycosylation site present in the sequence has been mutated, such that said mutated polypeptide is in non-glycosylated form.

2. A polypeptide according to claim 1, wherein the polypeptide comprises one or more conservative amino acid substitutions.

3. The-TGM polypeptide according to claim 1 having immunosuppressive activity in a pharmaceutically acceptable carrier.

4. A method of converting peripheral T cells into regulatory T cells (Treg cells) for use in treating inflammatory diseases, said method comprising contacting a sample of peripheral T cells with a polypeptide of claim 1, culturing said cells with said polypeptide in culture medium, and collecting converted Treg cells from said culture medium.

5. A method according to claim 4 wherein the peripheral T cells are obtained from an individual suffering from an inflammatory disorder or disease.

6. A method according to claim 5 further comprising administering said converted Treg cells to said individual suffering from an inflammatory disorder or disease.

7. A method according to claim 4 further comprising the step of preparing a pharmaceutical composition comprising said converted Treg cells.

* * * * *